United States Patent [19]

Sato et al.

[11] Patent Number: 5,506,239
[45] Date of Patent: Apr. 9, 1996

[54] CARBOSTYRIL DERIVATIVE AND PLATELETS AGGREGATION INHIBITORY AGENT

[75] Inventors: Seiji Sato; Hirotaka Yukawa, both of Tokushima; Yoshito Kihara, Naruto; Nobuyuki Koga, Tokushima; Masahiro Saitoh, Tokushima; Takao Nishi, Tokushima, all of Japan

[73] Assignee: Otsuka Pharmaceutical Co., Ltd., Japan

[21] Appl. No.: 39,301

[22] PCT Filed: Aug. 18, 1992

[86] PCT No.: PCT/JP92/01041

§ 371 Date: Apr. 22, 1993

§ 102(e) Date: Apr. 22, 1993

[87] PCT Pub. No.: WO93/04042

PCT Pub. Date: Mar. 4, 1993

[30] Foreign Application Priority Data

Aug. 23, 1991 [JP] Japan ..................... 3-211268

[51] Int. Cl.$^6$ ...................................... A61K 31/47
[52] U.S. Cl. .................... 514/312; 514/235.2; 514/253; 514/278; 546/157; 546/158; 546/16; 544/128; 544/363
[58] Field of Search ................... 546/157, 158, 546/16; 544/128, 63; 514/312, 235.2, 278, 253

[56] References Cited

U.S. PATENT DOCUMENTS

| | | | |
|---|---|---|---|
| 3,994,900 | 11/1976 | Krapcho et al. | 260/286 |
| 4,070,470 | 1/1978 | Nakagawa et al. | 424/258 |
| 4,216,220 | 8/1980 | Nakagawa et al. | 424/274 |
| 4,277,479 | 7/1981 | Nishi et al. | 424/258 |
| 4,298,739 | 11/1981 | Nishi et al. | 546/158 |
| 4,313,947 | 4/1982 | Nakagawa et al. | 424/248 |
| 4,329,374 | 5/1982 | Invernizzi et al. | 426/582 |
| 4,435,404 | 3/1984 | Nishi et al. | 424/258 |
| 5,008,274 | 4/1991 | Nishi et al. | 514/312 |
| 5,053,514 | 10/1991 | Fujioka et al. | 546/157 |

FOREIGN PATENT DOCUMENTS

| | | |
|---|---|---|
| 53-21176 | 2/1978 | Japan. |
| 54-5981 | 1/1979 | Japan. |
| 54-12385 | 1/1979 | Japan. |
| 54-115383A | 9/1979 | Japan. |
| 55-79370A | 6/1980 | Japan. |
| 56-122356A | 9/1981 | Japan. |
| 57-2274A | 1/1982 | Japan. |
| 57-14574A | 1/1982 | Japan. |
| 63-290821A | 11/1988 | Japan. |

*Primary Examiner*—José G. Dees
*Assistant Examiner*—Samuel Barts
*Attorney, Agent, or Firm*—Finnegan, Henderson, Farabow, Garrett & Dunner

[57] ABSTRACT

A carbostyril derivative or salt thereof of the formula

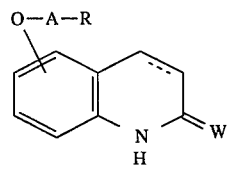

the carbon-to-carbon bond between the 3- and 4-positions of the carbostyril skeleton being a single bond or a double bond. The carbostyril derivatives are useful as a platelets aggregation inhibitory agent.

52 Claims, No Drawings

CARBOSTYRIL DERIVATIVE AND PLATELETS AGGREGATION INHIBITORY AGENT

FIELD OF THE INVENTION

The present invention relates to a carbostyril derivative and a platelets aggregation inhibitory agent containing said derivative as an active ingredient.

BACKGROUND ART

Compounds having structural formulas similar to that of the carbostyril derivative of the present invention are disclosed in the following prior art literature (patents).

The prior art by the present applicant

U.S. Pat. Nos. 4,070,470, 4,216,220, 4,313,947, 4,298,739, 4,277,479, 4,435,404, 5,008,274 and 5,053,514; EP-A-8910919; Japanese Patent Application Kokai (Laid-open) Nos. 50-82218, 50-106977, 50-142576, 50-151881, 54-30180, 54-30183, 54-30184, 55-79371, 57-9780, 57-14574, 57-93962, 57-159778, 58-59980, 56-8319, 57-80322, 52-108980 and 63-290821.

The prior art by other applicants

Japanese Patent Application Kokai (Laid-open) No. 56-16470 (U.S. Pat. No. 4329347); Japanese Patent Application Kokai (Laid-open) No. 56-36452; Japanese Patent Application Kokai (Laid-open) No. 59-31753 (EP-A-96006A); U.S. Pat. No. 3994900; BE-A-859415; and EP-A-71150 [Japanese Patent Application Kokai (Laid-open) No. 58-24559].

The structural formulas of the carbostyril compounds disclosed in the above prior art literature (patents) are similar to that of the carbostyril derivative of the present invention, but are different from the latter in the side chain structures. Although some of the carbostyril compounds disclosed in the prior art literature, similarly to the carbostyril derivative of the present invention, have a platelets aggregation inhibitory activity, the compounds of the prior art include also those showing different pharmacological activities such as antithrombotic activity, antihistaminic activity, antiarrhythmic activity, cardiotonicactivity, α- and β-adrenergic blocking activity and the like.

[DISCLOSURE OF THE INVENTION]

The carbostyril derivative of the present invention is represented by the following general formula (1).

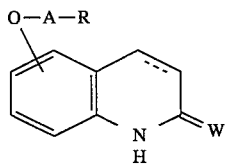

{wherein A represents a lower alkylene group.
R represents a group

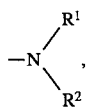

a group

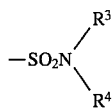

or a group

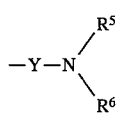

[wherein $R^1$ represents a group

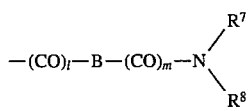

(wherein l and m independently represent 0 or 1. B represents a lower alkylene group. Each of $R^7$ and $R^8$, which may be the same or different, represents a hydrogen atom, a lower alkyl group which may have a hydroxyl group, or a lower alkanoyl group. Further, $R^7$ and $R^8$ may form a five- or six-membered saturated heterocyclic ring, together with the nitrogen atom to which they bond and further with or without a nitrogen, oxygen or sulfur atom which may be present between $R^7$ and $R^8$. Said heterocyclic ring may have 1–3 substituents selected from the group consisting of a hydroxyl group, a lower alkyl group which may have a lower alkoxy-lower alkoxy group or a hydroxyl group, a lower alkyl group-substituted or unsubstituted amino group, a lower alkoxy-lower alkoxy group, an oxo group and a lower alkyl group-substituted or unsubstituted aminocarbonyl group. Said heterocylic ring may also have a lower alkylenedioxy group as a substituent.); a lower alkoxycarbonyl group-substituted lower alkyl group; a carboxy group-substituted lower alkyl group; a lower alkyl group having, as a substituent, a lower alkyl group-substituted or unsubstituted aminocarbonyl group; a hydroxyl group-containing lower alkyl group; an imidazolyl-substituted lower alkyl group; a pyridyl-substituted lower alkyl group; a pyrrolidinyl-lower alkyl group which may have, as substituent(s) on the pyrrolidine ring, 1–3 groups selected from the group consisting of a lower alkyl group, a lower alkoxy-lower alkoxy group and a hydroxyl group; or a group —$SO_2$—D—$R^9$ (wherein D represents a lower alkylene group. $R^9$ represents a five- or six-membered saturated or unsaturated heterocylic ring residue having from 1–3 halogen atoms or nitrogen atoms. Said heterocyclic ring may have, as a substituent, a hydroxyl group, a lower alkoxy-lower alkoxy group, a lower alkoxycarbonyl group, or a lower alkyl group which may have a lower alkoxy-lower alkoxy group or a hydroxyl group.).

$R^2$ represents a hydrogen atom; a cycloalkyl-lower alkyl group; a cycloalkyl group; a phenyl group; a phenyl-lower alkyl group which may have, as substituent(s) on the phenyl ring, 1–3 groups selected from the group consisting of a halogen atom, a lower alkyl group, a cyano group, a carboxy group and a lower alkoxy group; a pyridyl-substituted lower alkyl group; a thienyl-substituted lower alkyl group; a cycloalkylcarbonyl group; a benzoyl group; a tetrahydropyranyl-substituted lower alkyl group; a phenyl-lower alkylsulfonyl group; a phenylsulfonyl group; or a cycloalkyl-lower alkylsulfonyl group.

$R^1$ and $R^2$ may form a pyrrolidinyl group together with the nitrogen atom to which they bond. Said pyrrolidinyl group has 1–2 substituents selected from the group consisting of a hydroxyl group, a lower alkoxy-lower alkoxy group, a lower alkyl group which may have a lower alkoxy-lower alkoxy group or a hydroxyl group, a lower alkoxycarbonyl group, a piperidinylcarbonyl group and a cycloalkyl-lower alkyl group-substituted or unsubstituted aminocarbonyl group.

$R^3$ represents a hydrogen atom; a lower alkyl group which may have a hydroxyl group; a carboxy-substituted lower alkyl group; a lower alkoxycarbonyl group-substituted lower alkyl group; a group

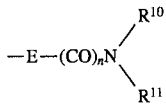

(wherein E represents a lower alkylene group which may have a hydroxyl group. n represents 0 or 1. Each of $R^{10}$ and $R^{11}$, which may be the same or different, represents a hydrogen atom; a lower alkyl group which may have a hydroxyl group; or a lower alkanoyl group. Further, $R^{10}$ and $R^{11}$ may form a five- or six-membered saturated heterocyclic ring, together with the nitrogen atom to which they bond and further with or without a nitrogen, oxygen or sulfur atom which may be present between $R^{10}$ and $R^{11}$. Said heterocyclic ring may have 1–3 substituents selected from the group consisting of a hydroxyl group; an oxo group; a lower alkoxy-lower alkoxy group; a lower alkyl group which may have a lower alkoxy-lower alkoxy group or a hydroxyl group; and a lower alkyl-substituted or unsubstituted amino group. Said heterocyclic ring may also have a lower alkylenedioxy group as a substituent.); or a pyrrolidinyl-lower alkyl group which may have, as substituent(s) on the pyrrolidine ring, 1–3 groups selected from the groupconsisting of a lower alkyl group, a lower alkoxy-lower alkoxy group and a hydroxyl group.

$R^4$ represents a hydrogen atom; a cycloalkyl group; a cycloalkyl-lower alkyl group; a phenyl-lower alkyl group which may have, as substituent(s) on the phenyl ring, 1–3 groups selected from the group consisting of a halogen atom, a lower alkyl group and a lower alkoxy group; a phenyl group; a thienyl-substituted lower alkyl group; a pyridyl-substituted lower alkyl group; an imidazolyl-substituted lower alkyl group; or a tetrahydropyranyl-substituted lower alkyl group.

Y represents a group

a group

or a group

Each of $R^5$ and $R^6$, which may be the same or different, represents a hydrogen atom; a lower alkyl group; a cycloalkyl group; a cycloalkyl-lower alkyl group; or a piperidinyl-lower alkyl group which may have, as a substituent on the piperidinyl ring, a lower alkoxy-lower alkoxy group or a hydroxyl group.].

W represents an oxygen atom or a sulfur atom.

The carbon-to-carbon bond between the 3- and 4-positions of the carbostyril skeleton represents a single bond or a double bond.}.

Of the carbostyril derivatives represented by the above general formula (1), the compounds represented by the following general formula (1A) are novel compounds not disclosed in any literature yet.

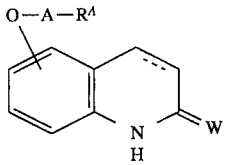

(1A)

{wherein A represents a lower alkylene group.
$R^A$ represents a group

a group

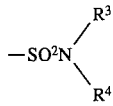

or a group

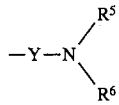

[wherein $R^1$ represents a group

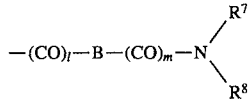

(wherein l and m independently represent 0 or 1. B represents a lower alkylene group. Each of $R^7$ and $R^8$, which may be the same or different, represents a hydrogen atom, a lower alkyl group which may have a hydroxyl group, or a lower alkanoyl group. Further, $R^7$ and $R^8$ may form a five- or six-membered saturated heterocyclic ring, together with the nitrogen atom to which they bond and further with or without a nitrogen, oxygen or sulfur atom which may be present between $R^7$ and $R^8$. Said heterocyclic ring may have 1–3 substituents selected from the group consisting of a hydroxyl group, a lower alkyl group which may have a lower alkoxy-lower alkoxy group or a hydroxyl group, a lower alkyl group-substituted or unsubstituted amino group, a lower alkoxy-lower alkoxy group, an oxo group and a lower alkyl group-substituted or unsubstituted aminocarbonyl group. Said heterocyclic ring may also have a lower alkylenedioxy group as a substituent.); a lower alkoxycarbonyl group-substituted lower alkyl group; a carboxy group-substituted lower alkyl group; a lower alkyl group having, as a substituent, a lower alkyl group-substituted or unsubstituted aminocarbonyl group; a hydroxyl group-containing lower alkyl group; an imidazolyl-substituted lower alkyl group; a pyridyl-substituted lower alkyl group; a pyrrolidinyl-lower alkyl group which may have, as substituent(s) on the pyrrolidine ring, 1–3 groups selected from the group consisting of a lower alkyl group, a lower alkoxy-lower alkoxy group and a hydroxyl group; or a group —$SO_2$—D—$R^9$ (wherein D represents a lower alkylene group. $R^9$ represents a five- or six-membered saturated or unsaturated heterocylic ring residue having 1-3 halogen atoms or nitrogen atoms. Said heterocyclic ring may have, as a substituent, a hydroxyl group, a lower alkoxy-lower alkoxy group, a lower alkoxycarbonyl group, or a lower alkyl group which may have a lower alkoxy-lower alkoxy group or a hydroxyl group.).

$R^2$ represents a hydrogen atom; a cycloalkyl-lower alkyl group; a cycloalkyl group; a phenyl group; a phenyl-lower alkyl group which may have, as substituent(s) on the phenyl ring, 1-3 groups selected from the group consisting of a halogen atom, a lower alkyl group, a cyano group, a carboxy group and a lower alkoxy group; a pyridyl-substituted lower alkyl group; a thienyl-substituted lower alkyl group; a cycloalkylcarbonyl group; a benzoyl group; a tetrahydropyranyl-substituted lower alkyl group; a phenyl-lower alkylsulfonyl group; a phenylsulfonyl group; or a cycloalkyl-lower alkylsulfonyl group.

$R^1$ and $R^2$ may form a pyrrolidinyl group together with the nitrogen atom to which they bond. Said pyrrolidinyl group has 1-2 substituents selected from the group consisting of a hydroxyl group, a lower alkoxy-lower alkoxy group, a lower alkyl group having a lower alkoxy-lower alkoxy group or a hydroxyl group, a lower alkoxycarbonyl group, apiperidinylcarbonyl group and a cycloalky.-lower alkyl group-substituted or unsubstituted aminocarbonyl group.

$R^3$ represents a hydrogen atom; a lower alkyl group which may have a hydroxyl group; a carboxy-substituted lower alkyl group; a lower alkoxycarbonyl group-substituted lower alkyl group; a group

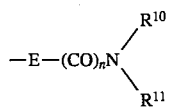

(wherein E represents a lower alkylene group which may have a hydroxyl group. n represents 0 or 1. Each of $R^{10}$ and $R^{11}$, which may be the same or different, represents a hydrogen atom; a lower alkyl group which may have a hydroxyl group; or a lower alkanoyl group. Further, $R^{10}$ and $R^{11}$ may form a five- or six-membered saturated heterocyclic ring, together with the nitrogen atom to which they bond and further with or without a nitrogen, oxygen or sulfur atom which may be present between $R^{10}$ and $R^{11}$. Said heterocyclic ring may have 1-3 substituents selected from the group consisting of a hydroxyl group; an oxo group; a lower alkoxy-lower alkoxy group; a lower alkyl group which may have a lower alkoxy-lower alkoxy group or a hydroxyl group; and a lower alkyl-substituted or unsubstituted amino group. Said heterocylic ring may also have a lower alkylenedioxy group as a substituent.); or a pyrrolidinyl-lower alkyl group which may have, as substituent(s) on the pyrrolidine ring, 1-3 groups selected from the group consisting of a lower alkyl group, a lower alkoxy-lower alkoxy group and a hydroxyl group.

$R^4$ represents a hydrogen atom; a cycloalkyl group; a cycloalkyl-lower alkyl group; a phenyl-lower alkyl group which may have, as substituent(s) on the phenyl ring, 1-3 groups selected from the group consisting of a halogen atom, a lower alkyl group and a lower alkoxy group; a phenyl group; a thienyl-substituted lower alkyl group; a pyridyl-substituted lower alkyl group; an imidazolyl-substituted lower alkyl group; or a tetrahydropyranyl-substituted lower alkyl group.

Y represents a group

a group

or a

Each of $R^5$ and $R^6$ which may be the same or different, represents a hydrogen atom; a lower alkyl group; a cycloalkyl group; a cycloalkyl-lower alkyl group; or a piperidinyl-lower alkyl group which may have, as a substituent on the piperidinyl ring, a lower alkoxy-lower alkoxy group or a hydroxyl group.].

W represents an oxygen atom or a sulfur atom.

The carbon-to-carbon bond between the 3- and 4-positions of the carbostyril skeleton represents a single bond or a double bond.

When W is an oxygen atom and $R^1$ is a hydroxyl group-containing lower alkyl group, $R^2$ must not be any of a hydrogen atom, a cycloalkyl group and a phenyl-lower alkyl group which may have, as substituent(s) on the phenyl ring, 1-3 groups selected from the group consisting of a lower alkoxy group and a halogen atom.

When $R^1$ and $R^2$ form a pyrrolidinyl group, the pyrrolidinyl group must not be a pyrrolidinyl group substituted with a hydroxyl group or with a hydroxyl group-containing lower alkyl group.}.

According to the research by the present inventors, the carbostyril derivative represented by the above general formula (1) or its salt is superior in platelets aggregation inhibitory activity, phosphodiesterase inhibitory activity, cardiocontraction increase activity (positive contraction activity), antiulcerative activity, antiinflammatory activity, brain and peripheral blood flow increasing activity, platelet plug dissecting activity, thromboxane $A_2$ antagonistic activity, etc. The compound of the present invention is characterized by having long sustaining times for the above-mentioned activities, low toxicity (the toxicity to heart when used for cardiac vascular hypertrophy, myocardial disturbance, etc. is particularly low), and very low circulatory effects for heart rate increase, blood pressure reduction, etc. The present compound also has an advantage that it is readily absorbed by intestinal tract and easily transferred into blood. Thus, the compound of the present invention can be most suitably used as a prophylactic and treating agent for thrombosis (e.g. cerebral apoplexia, cerebral infarction, myocardial infarction), a peripheral circulation improving agent, a cerebral circulation improving agent, an antiinflammatory agent, an antiasthmatic agent, a prophylactic and treating agent for diabetic complication (e.g. neurosis, nephritis), a cardiotonic agent and a phosphodiesterase agent.

The compound of the present invention further has a platelets adhesion inhibitory activity and therefore can be used, for example, as a prophylactic and treating agent for arteriosclerosis, ischemic heart disease, chronic arterial embolism, acute or chronic nephritis, etc.; for the postoperative administration of blood vessel in percutaneous transluminal coronary angioplasty (PTCA), etc.; as a prophylactic and treating agent for coronary arterial re-embolism due to indwelling of stent in blood vessel; and at the time of dialysis treatment or artificial organ embedding.

Each of the individual groups shown in the above general formula (1) is as follows.

As to the lower alkylene group, there can be mentioned, for example, straight chain or branched chain alkylene groups each of 1-6 carbon atoms, such as methylene, ethylene, methylmethylene, trimethylene, 2-methyltrimethylene, 2,2-dimethyltrimethylene, tetramethylene, pentamethylene, hexamethylene, 2-ethyltrimethylene, 1-methyltrimethylene and the like.

The lower alkyl group which may have a lower alkoxy-lower alkoxy group or a hydroxyl group, can be exemplified by straight chain or branched chain alkyl groups each of 1–6 carbon atoms, which may each have 1–3 hydroxyl groups or 1–3 alkoxyalkoxy groups whose alkoxy portions are each a straight chain or branched chain alkoxy group of 1–6 carbon atoms, such as methyl, ethyl, propyl, isopropyl, butyl, tert-butyl, pentyl, hexyl, methoxymethoxymethyl, 2-methoxymethoxyethyl, 3-methoxymethoxypropyl, 2,3-dimethoxymethoxypropyl, 2-hydroxyethyl, 3-hydroxypropyl, 4-hydroxybutyl, 2-hydroxybutyl, 3-hydroxybutyl, 5-hydroxypentyl, 2-hydroxypentyl, 3-hydroxypentyl, 4-hydroxypentyl, 6-hydroxyhexyl, 2-hydroxyhexyl, 3-hydroxyhexyl, 4-hydroxyhexyl, 1-methyl-2-hydroxyethyl, 2-hydroxypropyl, 1,1-dimethyl-2-hydroxyethyl, 1,2-dihydroxyethyl, 2,2-dihydroxyethyl, 1,3-dihydroxypropyl, 2,3-dihydroxypropyl, 1,2,3-trihydroxypropyl, 1,4-dihydroxybutyl, 2,4-dihydroxybutyl, 3,4-dihydroxybutyl, 1,2-dihydroxybutyl, 2,3-dihydroxybutyl, 1,3-dihydroxybutyl, 2,2-dihydroxybutyl, 1,2,3-trihydroxybutyl, 2,3,4-trihydroxybutyl,2,3-dihydroxypentyl, 3,4-dihydroxypentyl, 3,5-dihydroxypentyl,2,3,4-trihydroxypentyl, 3,4,5-trihydroxypentyl, 2,4,5-trihydroxypentyl, 2,3-dihydroxyhexyl, 2,5-dihydroxyhexyl, 2,6-dihydroxyhexyl, 3,4-dihydroxyhexyl, 4,5-dihydroxyhexyl, 4,6-dihydroxyhexyl, 5,6-dihydroxyhexyl, 2,3,4-trihydroxyhexyl, 3,4,5-trihydroxyhexyl,4,5,6-trihydroxyhexyl and the like.

As to the lower alkanoyl group, there can be mentioned, for example, straight chain or branched chain alkanoyl groups each of 1–6 carbon atoms, such as formyl, acetyl, propionyl, butyryl, isobutyryl, pentanoyl, tert-butylcarbonyl, hexanoyl and the like.

As to the lower alkyl-substituted or unsubstituted amino group, there can be mentioned, for example, amino groups which may each have, as substituent(s), 1–2 straight chain or branched chain alkyl groups each of 1–6 carbon atoms, such as amino, methylamino, ethylamino, propylamino, isopropylamino, butylamino, tert-butylamino, pentylamino, hexylamino, dimethylamino, diethylamino, dipropylamino, dibutylamino, dipentylamino, dihexylamino, N-methyl-N-ethylamino, N-ethyl-N-propylamino, N-methyl-N-butylamino, N-methyl-N-hexylamino and the like.

As to the lower alkyl-substituted or unsubstituted aminocarbonyl group, there can be mentioned, for example, aminocarbonyl groups which may have, as substituent(s), 1–2 straight chain or branched chain alkyl groups each of 1–6 carbon atoms, such as aminocarbonyl, methylaminocarbonyl, ethylaminocarbonyl, propylaminocarbonyl, isopropylamino-carbonyl, butylaminocarbonyl, tert-butylaminocarbonyl, pentylaminocarbonyl, hexylaminocarbonyl, dimethylaminocarbonyl, diethylaminocarbonyl, dipropylaminocarbonyl, dibutylaminocarbonyl, dipentylaminocarbonyl, dihexylaminocarbonyl, N-methyl-N-ethylaminocarbonyl, N-ethyl-N-propylaminocarbonyl, N-methyl-N-butylaminocarbonyl, N-methyl-N-hexylaminocarbonyl and the like.

As to the lower alkylenedioxy group, there can be mentioned, for example, straight chain or branched chain alkylenedioxy groups each of 1–4 carbon atoms, such as methylenedioxy, ethylenedioxy, trimethylenedioxy, tetramethylenedioxy and the like.

As to the lower alkoxycarbonyl group-substituted lower alkyl group, there can be mentioned, for example, straight chain or branched chain alkoxycarbonylalkyl groups each of 1–6 carbon atoms, whose alkyl portions are each a straight chain or branched chain alkyl group of 1–6 carbon atoms, such as methoxycarbonylmethyl, 3-methoxycarbonylpropyl, 4-ethoxycarbonylbutyl, 6-propoxycarbonylhexyl, 5-isopropoxycarbonylpentyl, 1,1-dimethyl-2-butoxycarbonylethyl, 2-methyl-tert-butoxycarbonylpropyl, 2-pentyloxycarbonylethyl, hexyloxycarbonylmethyl and the like.

The carboxy-lower alkyl group can be exemplified by carboxyalkyl groups whose alkyl portions are each a straight chain or branched chain alkyl group of 1–6 carbon atoms, such as carboxymethyl, 2-carboxyethyl, 1-carboxyethyl, 3-carboxypropyl, 4-carboxybutyl, 1,1-dimethyl-2-carboxyethyl, 5-carboxypentyl, 6-carboxyhexyl, 2-methyl-3-carboxypropyl and the like.

As to the lower alkyl group having, as a substituent, a lower alkyl group-substituted or unsubstituted aminocarbonyl group, there can be mentioned straight chain or branched chain alkyl groups each of 1–6 carbon atoms, each having, as a substituent, an aminocarbonyl group which may have 1–2 straight chain or branched chain alkyl groups each of 1–6 carbon atoms, such as aminocarbonylmethyl, 1-aminocarbonyl-ethyl, 2-aminocarbonylethyl, 3-aminocarbonylpropyl, 4-aminocarbonylbutyl, 5-aminocarbonylpentyl, 6-aminocarbonylhexyl, 1,1-dimethyl-2-aminocarbonylethyl, 2-methyl-3-aminocarbonylpropyl, methylaminocarbonylmethyl, ethylaminocarbonylmethyl, propylaminocarbonylmethyl, isopropylaminocarbonylmethyl, butylaminocarbonylmethyl, tert-butylaminocarbonylmethyl, pentylaminocarbonylmethyl, hexylaminocarbonylmethyl, dimethylaminocarbonylmethyl, diethylaminocarbonylmethyl, diethylaminocarbonylmethyl, dipropylaminocarbonylmethyl, dibutylaminocarbonylmethyl, dipentylaminocarbonylmethyl, dihexylaminocarbonylmethyl, N-methyl-N-ethylaminocarbonylmethyl, N-ethyl-N-propylaminocarbonylmethyl, N-methyl-N-butylaminocarbonylmethyl, N-methyl-N-hexylaminocarbonylmethyl, 2-methylaminocarbonylethyl, 1-ethylaminocarbonylethyl, 3-propylaminocarbonylpropyl, 4-butylaminocarbonylbutyl, 1,1-dimethyl-2-pentylaminocarbonylethyl, 5-hexylaminocarbonylpentyl, 6-dimethylaminocarbonylhexyl, 2-diethylaminocarbonylethyl, 1-(N-methyl-N-hexylamino)carbonylethyl, 3-dihexylaminocarbonylpropyl, 4-dibutylaminocarbonylbutyl, 2-(N-methyl-N-pentylamino)carbonylethyl and the like.

As to the hydroxyl group-containing lower alkyl group can be exemplified by straight chain or branched chain alkyl groups each of 1–6 carbonyl atoms, each having 1–3 hydroxyl groups, such as 2-hydroxyethyl, 3-hydroxypropyl, 4-hydroxybutyl, 2-hydroxybutyl, 3-hydroxybutyl, 5-hydroxypentyl, 2-hydroxypentyl, 3-hydroxypentyl, 4-hydroxypentyl, 6-hydroxypentyl, 2-hydroxyhexyl, 3-hydroxyhexyl, 4-hydroxyhexyl, 1-methyl-2-hydroxyethyl, 2-hydroxypropyl, 1,1-dimethyl-2-hydroxyethyl, 1,2-dihydroxyethyl, 2,2-dihydroxyethyl, 1,3-dihydroxypropyl, 2,3-dihydroxypropyl, 1,2,3-trihydroxypropyl, 1,4-dihydroxybutyl, 2,4-dihydroxy butyl, 3,4-dihydroxybutyl, 1,2-dihydroxybutyl, 2,3-dihydroxybutyl, 1,3-dihydroxybutyl, 2,2-dihydroxybutyl, 1,2,3-trihydroxybutyl, 2,3,4-trihydroxybutyl, 2,3-dihydroxypentyl, 3,4-dihydroxypentyl, 3,5-dihydroxypentyl, 2,3,4-trihydroxypentyl, 3,4,5-trihydroxypentyl, 2,4,5-trihydroxypentyl, 2,3-dihydroxyhexyl, 2,5-dihydroxyhexyl, 2,6-dihydroxyhexyl, 3,4-dihydroxyhexyl, 4,5-dihydroxyhexyl, 4,6-dihydroxyhexyl, 5,6-dihydroxyhexyl, 2,3,4-trihydroxyhexyl, 3,4,5-trihydroxyhexyl, 4,5,6-trihydroxyhexyl and the like.

As to the imidazolyl-substituted lower alkyl group, there can be mentioned, for example, imidazolylalkyl groups whose alkyl portions are each a straight chain or branched chain alkyl group of 1–6 carbon atoms, such as (2-imidazolyl)-methyl, 2-(1-imidazolyl)ethyl, 1-(4-imidazolyl)ethyl, 3-(5-imidazolyl)propyl, 4-(2-imidazolyl)-butyl, 1,1-dimethyl-2-(4-imidazolyl)ethyl, 5-(1-imidazolyl)pentyl, 6-(5-imidazolyl)hexyl, 2-methyl-3-(1-imidazolyl)propyl and the like.

The pyridyl-substituted lower alkyl group can be exemplified by pyridyl-substituted alkyl groups whose alkyl portions are each a straight chain or branched chain alkyl group of 1–6 carbon atoms, such as (2-pyridyl)methyl, 2-(3-pyridyl)ethyl, 1-(4-pyridyl)ethyl, 3-(4-pyridyl)propyl, 4-(2-pyridyl)butyl, 1,1-dimethyl-2-(3-pyridyl)ethyl, 5-(4-pyridyl)pentyl, 6-(2-pyridyl)hexyl, 2-methyl-3-(3-pyridyl)propyl and the like.

The pyrrolidinyl-lower alkyl group which may have, as substituent(s) on the pyrrolidine ring, 1–3 groups selected from the group consisting of a lower alkyl group, a lower alkoxy-lower alkoxy group and a hydroxyl group, can be exemplified by pyrrolidinylalkyl groups whose alkyl groups are each a straight chain or branched chain alkyl group of 1–6 carbon atoms and which may have, as substituent(s) on the pyrrolidine ring, 1–3 groups selected from the group consisting of a straight chain or branched chain alkyl group of 1–6 carbon atoms and a hydroxyl group, such as (2-pyrrolidinyl)methyl, 2-(3-pyrrolidinyl)ethyl, 1-(2-pyrrolidinyl)ethyl, 3-(2-pyrrolidinyl)propyl, 4-(3-pyrrolidinyl)butyl, 5-(3-pyrrolidinyl)pentyl, 6-(2-pyrrolidinyl)hexyl, (3-methoxymethoxy-1-ethoxy-2-pyrrolidinyl)methyl, (1,3-dimethyl-4-ethoxymethoxy-2-pyrrolidinyl)methyl, 2-(3-propoxymethoxy-1-pyrrolidinyl)ethyl, 1,1-dimethyl-2-(2-pyrrolidinyl)ethyl, 2-methyl-3-(3-pyrrolidinyl)propyl, (1-ethyl-4-hydroxy-2-pyrrolidinyl)methyl, 2-(1-methyl-3-pyrrolidinyl)ethyl, 1-(1-propyl-2-pyrrolidinyl)-ethyl, 3-(1-butyl-4-hydroxy-2-pyrrolidinyl)propyl, 4-(1-pentyl-3,4-dihydroxy-3-pyrrolidinyl)butyl, 5-(1-hexyl-3-pyrrolidinyl)pentyl, 6-(1-methyl-2-pyrrolidinyl)hexyl, (1,3-dimethyl-4-hydroxy-2-pyrrolidinyl)methyl, 2-(3-hydroxy-2-pyrrolidinyl)ethyl, (4-hydroxy-2-pyrrolidinyl)methyl, 3-(5-hydroxy-2-pyrrolidinyl)propyl and the like.

As to the lower alkoxycarbonyl group, there can be mentioned, for example, alkoxycarbonyl groups whose alkoxy portions are each a straight chain or branched chain alkoxy group of 1–6 carbon atoms, such as methoxycarbonyl, ethoxycarbonyl, propoxycarbonyl, isopropoxycarbonyl, butoxycarbonyl, pentyloxycarbonyl, hexyloxycarbonyl and the like.

As to the cycloalkyl-lower alkyl group, there can be mentioned, for example, cycloalkylalkyl groups each of 3–8 carbon atoms, whose alkyl portions are each a straight chain or branched chain alkyl group of 1–6 carbon atoms, such as cyclopropylmethyl, cyclobutylmethyl, cyclopentylmethyl, cyclohexylmethyl, cycloheptylmethyl, cyclooctylmethyl, 2-cyclopropylethyl, 1-cyclobutylethyl, 3-cyclopentylpropyl, 4-cyclohexylbutyl, 5-cycloheptylpentyl, 6-cyclooctylhexyl, 2-methyl-3-cyclohexylpropyl, 2-cyclohexylethyl, 1-cyclohexylethyl and the like.

As to the cycloalkyl group, there can be mentioned, for example, cycloalkyl groups each of 3–8 carbon atoms, such as cyclopropyl, cyclobutyl, cyclopentyl, cyclohexyl, cycloheptyl, cyclooctyl, cyclononanyl, cyclodecanyl and the like.

The lower alkoxy group can be exemplified by straight chain or branched chain alkoxy groups each of 1–6 carbon atoms, Such as methoxy, ethoxy, propoxy, isopropoxy, butoxy, tert-butoxy, pentyloxy, hexyloxy and the like.

As to the lower alkyl group, there can be mentioned, for example, straight chain or branched chain alkyl groups each of 1–6 carbon atoms, such as methyl, ethyl, propyl, isopropyl, butyl, tert-butyl, pentyl, hexyl and the like.

The phenyl-lower alkyl group which may have, as substituent(s) on the phenyl ring, 1–3 groups selected from the group consisting of a halogen atom, a lower alkyl group, a cyano group, a carboxy group and a lower alkoxy group, can be exemplified by phenylalkyl groups whose alkyl portions are each a straight chain or branched chain alkyl group of 1–6 carbon atoms and which may have, as substituent(s) on the phenyl ring, 1–3 groups selected from the group consisting of a halogen atom, a straight chain or branched chain alkyl group of 1–6 carbon atoms, a carboxy group, a cyano group and a straight chain or branched chain alkoxy group of 1–6 carbon atoms, such as benzyl, 2-phenylethyl, 1-phenylethyl, 3-phenylpropyl, 4-phenylbutyl, 1,1-dimethyl-2-phenylethyl, 5-phenylpentyl, 6-phenylhexyl, 2-methyl-3-phenylpropyl, 2-chlorobenzyl, 2-(3-chlorophenyl)ethyl, 1-(4-chlorophenyl)ethyl, 3-(2-fluorophenyl)propyl, 4-(3-fluorophenyl)butyl, 1,1-dimethyl-2-(4-fluorophenyl)ethyl, 5-(2-bromophenyl)pentyl, 6-(3-bromophenyl)hexyl, 2-methyl-3-(4-bromophenyl)propyl, 4-fluorobenzyl, 3-iodobenzyl, 2-(4-iodophenyl)ethyl, 1-(3,5-dichlorophenyl)ethyl, 3,4-dichlorobenzyl, 2-(3,4-dichlorophenyl)ethyl, 3-(2,6-dichlorophenyl)propyl, 4-(3,4-dichlorophenyl)butyl, 1,1-dimethyl-2-(3,4-difluorophenyl)ethyl, 5-(3,5-dibromophenyl)-pentyl, 6-(3,4,5-trichlorophenyl)hexyl, 4-methylbenzyl, 2-(2-methylphenyl)ethyl, 1-(3-methylphenyl)-ethyl, 3-(3-ethylphenyl)propyl, 4-(2-ethylphenyl)butyl, 5-(4-ethylphenyl)pentyl, 6-(3-isopropylphenyl)hexyl, 2-methyl-3-(4-hexylphenyl)propyl, 2-(3,4-dimethylphenyl)ethyl, 2-(2,5-dimethylphenyl)ethyl, 2-(3,4,5-trimethylphenyl)ethyl, 4-methoxybenzyl, 3,4-dimethoxybenzyl, 3,4,5-trimethoxybenzyl, 1-(3-methoxyphenyl)ethyl, 2-(2-methoxyphenyl)ethyl, 3-(2-ethoxyphenyl)propyl, 4-(4-ethoxyphenyl)butyl, 5-(3-ethoxyphenyl)pentyl, 6-(4-isopropoxyphenyl) hexyl, 1,1-dimethyl-2-(4-hexyloxyphenyl)ethyl, 2-methyl-3-(3,4-dimethoxyphenyl)propyl, 2-(3,4-dimethoxyphenyl)ethyl, 2-(3,4-diethoxyphenyl)ethyl, 2-(3,4,5-trimethoxyphenyl)ethyl, 1-(2,5-dimethoxyphenyl)ethyl, (2-chloro-4-methoxy)benzyl, 4-cyanobenzyl, 1-(3-cyanophenyl)ethyl, 1-(2-cyanophenyl)propyl, 1-(2,3-dicyanophenyl)butyl, 1-(2,3,4-tricyanophenyl)pentyl, 1-(2,4-dicyanophenyl)hexyl, 4-carboxybenzyl, 1-(3-carboxyphenyl)ethyl, 1-(2-carboxyphenyl)propyl, 1-(2,4-dicarboxyphenyl)butyl, 1-(2,4,6-tricarboxyphenyl)pentyl, 1-(2-chloro-4-carboxyphenyl)hexyl, (3-methyl-4-cyano)benzyl and the like.

As to the thienyl-substituted lower alkyl group, there can be mentioned, for example, thienyl-substituted alkyl groups whose alkyl portions are each a straight chain or branched chain alkyl group of 1–6 carbon atoms, such as (2-thienyl)methyl, 2-(3-thienyl)ethyl, 1-(2-thienyl)ethyl, 3-(2-thienyl)propyl, 4-(3-thienyl)butyl, 1,1-dimethyl-2-(2-thienyl)ethyl, 5-(3-thienyl)pentyl, 6-(2-thienyl)hexyl, 2-methyl-3-(3-thienyl)propyl and the like.

The cycloalkylcarbonyl group can be exemplified by cycloalkylcarbonyl groups each of 3–10 carbon atoms, such as cyclopropylcarbonyl, cyclobutylcarbonyl, cyclopentylcarbonyl, cyclohexylcarbonyl, cycloheptylcarbonyl, cyclooctylcarbonyl, cyclononanylcarbonyl, cyclodecanylcarbonyl and the like.

As to the tetrahydropyranyl-substituted lower alkyl group, there can be mentioned tetrahydropyranyl-substituted alkyl groups whose alkyl portions are each a straight chain or branched chain alkyl group of 1–6 carbon atoms, such as (2-tetrahydropyranyl)methyl, (3-tetrahydropyranyl)methyl, (4-tetrahydropyranyl)methyl, 2-(2-tetrahydropyranyl)ethyl, 2-(3-tetrahydropyranyl)ethyl, 2-(4-tetrahydropyranyl)ethyl, 1-(2-tetrahydropyranyl)ethyl, 1-(3-tetrahydropyranyl)ethyl, 1-(4-tetrahydropyranyl)ethyl, 3-2-(tetrahydropyranyl)propyl, 3-(3-tetrahydropyranyl)propyl, 3-(4-tetrahydropyranyl)propyl, 4-(2-tetrahydropyranyl)butyl, 4-(3-tetrahydropyranyl)butyl, 4-(4-tetrahydropyranyl)butyl, 1,1-dimethyl-2-(2-tetrahydropyranyl)ethyl, 1,1-dimethyl-2-(3-tetrahydropyranyl)ethyl, 1,1-dimethyl-2-(4-tetrahydropyranyl)ethyl, 5-(2-tetrahydropyranyl)pentyl, 5-(3-tetrahydropyranyl)pentyl, 5-(4-tetrahydropyranyl)pentyl, 6-(2-tetrahydropyranyl)hexyl, 6-(3-tetrahydropyranyl)hexyl, 6-(4-tetrahydropyranyl)hexyl, 2-methyl-3-(2-tetrahydropyranyl)propyl, 2-methyl-3-(3-tetrahydropyranyl)propyl, 2-methyl-3-(4-tetrahydropyranyl)propyl and the like.

The phenyl-lower alkylsulfonyl group can be exemplified by phenylalkylsulfonyl groups whose alkyl portions are each a straight chain or branched chain alkyl group of 1–6 carbon atoms, such as benzylsulfonyl, 2-phenylethylsulfonyl, 1-phenylethylsulfonyl, 3-phenylpropylsulfonyl, 4-phenylbuytl-sulfonyl, 1,1-dimethyl-2-phenylethylsulfonyl, 5-phenylpentylsulfonyl, 6-phenylhexylsulfonyl, 2-methyl-3-phenylpropylsulfonyl and the like.

As to the cycloalkyl-lower alkylsulfonyl group, there can be mentioned, for example, cycloalkylalkylsulfonyl groups each of 3–8 carbon atoms, whose alkyl portions are each a straight chain or branched chain alkyl group of 1–6 carbon atom, such as cyclopropylmethylsulfonyl, cyclobutylmethylsulfonyl, cyclopentylmethylsulfonyl, cyclohexylmethylsulfonyl, cycloheptylmethylsulfonyl, cyclooctylmethylsulfonyl, 2-cyclopropylethylsulfonyl, 1-cyclobutylethylsulfonyl, 3-cyclopentylpropylsulfonyl, 4-cyclohexylbutylsulfonyl, 5-cycloheptylpentylsulfonyl, 6-cyclooctylhexylsulfonyl, 2-methyl-3-cyclohexylpropylsulfonyl, 2-cyclohexylethylsulfonyl, 1-cyclohexylethylsulfonyl and the like.

The cycloalkyl-lower alkyl group-substituted or unsubstituted aminocarbonyl group can be exemplified by aminocarbonyl groups which may have, as substituent(s), 1–2 cycloalkylalkyl groups each of 3–8 carbon atoms whose alkyl portions are each a straight chain or branched chain alkyl group of 1–6 carbon atoms, such as aminocarbonyl, cyclohexylmethylaminocarbonyl, cyclopropylmethylaminocarbonyl, cyclobutylmethylaminocarbonyl, cyclopentylmethylaminocarbonyl, cycloheptylmethylaminocarbonyl, cyclooctylmethylaminocarbonyl, (2-cyclopropylethyl)aminocarbonyl, (1-cyclobutylethyl)aminocarbonyl, (3-cyclopentylpropyl)aminocarbonyl, (4-cyclohexylbutyl)aminocarbonyl, (5-cycloheptylpenty)aminocarbonyl, (6-cyclooctylhexyl)aminocarbonyl, (2-methyl-3-cyclohexylpropyl)aminocarbonyl, (2-cyclohexylethyl)aminocarbonyl, (1-cyclohexylethyl)aminocarbonyl, dicyclohexylmethylaminocarbonyl, N-cyclohexylmethyl-N-cycloheptylmethylaminocarbonyl and the like.

The lower alkylene group which may have a hydroxyl group, can be exemplified by the above-mentioned lower alkylene groups and further by straight chain or branched chain alkylene groups each of 1–6 carbon atoms which may have hydroxyl group(s), such as 2-hydroxytrimethylene, 2-hydroxytetramethylene, 2,3-dihydroxytetramethylene, 3-hydroxypentamethylene, 3-hydroxytetramethylene, 5-hydroxyhexamethylene and the like.

The phenyl-lower alkyl group which may have, as substituent(s) on the phenyl ring, 1–3 groups selected from the group consisting of a halogen atom, a lower alkyl group and a lower alkoxy group, can be exemplified by phenylalkyl groups whose alkyl portions are each a straight chain or branched chain alkyl group of 1–6 carbon atoms and which may have, as substituent(s) on the phenyl ring, 1–3 groups selected from the group consisting of a halogen atom, a straight chain or branched chain alkyl group of 1–6 carbon atoms and a straight chain or branched chain alkoxy group of 1–6 carbon atoms, such as benzyl, 2-phenylethyl, 1-phenylethyl, 3-phenylpropyl, 4-phenylbutyl, 1,1-dimethyl-2-phenylethyl, 5-phenylpentyl, 6-phenylhexyl, 2-methyl-3-phenylpropyl, 2-chlorobenzyl, 2-(3-chlorophenyl)ethyl, 1-(4-chlorophenyl)ethyl, 3-(2-fluorophenyl)propyl, 4-(3-fluorophenyl)butyl, 1,1-dimethyl-2-(4-fluorophenyl)ethyl, 5-(2-bromophenyl)pentyl, 6-(3-bromophenyl)hexyl, 2-methyl-3-(4-bromophenyl)propyl, 4-fluorobenzyl, 3-iodobenzyl, 2-(4-iodophenyl)ethyl, 1-(3,5-dichlorophenyl)ethyl, 3,4-dichlorobenzyl, 2-(3,4-dichlorophenyl)ethyl, 3-(2,6dichlorophenyl)propyl, 4-(3,4-dichlorophenyl)butyl, 1,1-dimethyl-2-(3,4-difluorophenyl)ethyl, 5-(3,5-dibromophenyl)pentyl, 6-(3,4,5-trichlorophenyl)hexyl, 4-methylbenzyl, 2-(2-methylphenyl)ethyl, 1-(3-methylphenyl)ethyl, 3-(3-ethylphenyl)propyl, 4-(2-ethylphenyl)butyl, 5-(4-ethylphenyl)pentyl, 6-(3-isopropylphenyl)hexyl, 2-methyl-3-(4-hexylphenyl)propyl, 2-(3,4-dimethylphenyl)ethyl, 2-(2,5-dimethylphenyl)ethyl, 2-(3,4,5-trimethylphenyl)ethyl, 4-methoxybenzyl, 3,4-dimethoxybenzyl, 3,4,5-trimethoxybenzyl, 1-(3-methoxyphenyl)ethyl, 2-(2-methoxyphenyl)ethyl, 3-(2-ethoxyphenyl)propyl, 4-(4-ethoxyphenyl)butyl, 5-(3-ethoxyphenyl)pentyl, 6-(4-isopropoxyphenyl)hexyl, 1,1-dimethyl-2-(4-hexyloxyphenyl)ethyl, 2-methyl-3-(3,4-dimethoxyphenyl)propyl, 2-(3,4-dimethoxyphenyl)ethyl, 2-(3,4-diethoxyphenyl)ethyl, 2-(3,4,5-trimethoxyphenyl)ethyl, 1-(2,5-dimethoxyphenyl)ethyl, (2-chloro-4-methoxy-)benzyl and the like.

As to the piperidinyl-lower alkyl group which may have, as a substituent on the piperidinyl ring, a lower alkoxy-lower alkoxy group or a hydroxyl group, there can be mentioned, for example, piperidinylalkyl groups whose alkyl portions are each a straight chain or branched chain alkyl group of 1–6 carbon atoms and which may have, as substituent(s) on the piperidinyl ring, 1–3 hydroxyl groups or 1–3 alkoxyalkoxy groups whose alkoxy portions are each a straight chain or branched chain alkoxy group of 1–6 carbon atoms, such as (4-hydroxyl-1-piperidinyl)methyl, 2-(4-hydroxy-1-piperidinyl)ethyl, 1-(4-hydroxy-1-piperidinyl)ethyl, 3-(4-hydroxy-1-piperidinyl)propyl, 4-(4-hydroxy-1-piperidinyl-)butyl, 5-(4-hydroxy-1-piperidinyl)pentyl, 6-(4-hydroxy-1-piperidinyl)-hexyl, 1,1-dimethyl-2-(3-hydroxy-1-piperidinyl)ethyl, 2-methyl-3-(2-hydroxy-1-piperidinyl)propyl, 2-(2,4-dihydroxy-1-piperidinyl)ethyl, 3-(2-hydroxy-4-piperidinyl)propyl, (2,4,6-trihydroxy-1-piperidinyl)methyl, 1-(2-hydroxy-3-piperidinyl)ethyl, 4-(3-hydroxy-2-piperidinyl)-butyl, 5-(3-hydroxy-4-piperidinyl-)pentyl, 6-(2-hydroxy-3-piperidinyl)hexyl, 2-(4-methoxymethoxy-1-piperidinyl)ethyl, 3-(4-ethoxymethoxy-1-piperidinyl) propyl, 2-(2,4-dimethoxymethoxy-1-piperidinyl)ethyl and the like.

The five- or six-membered saturated heterocyclic ring group formed by $R^7$ and $R^8$ or by $R^{10}$ and $R^{11}$ together with the nitrogen atom to which $R^7$ and $R^8$ or $R^{10}$ and $R^{11}$ bond and further with or without a nitrogen, sulfur or oxygen atom which may be present between $R^7$ and $R^8$ or $R^{10}$ and $R^{11}$, can be exemplified by pyrrolidinyl, piperidinyl, piperazinyl, morpholinyl, thiomorpholinyl, isothiazolidinyl, 3,4,5,6-tetrahydro-1,2-thiazinyl.

The above heterocyclic ring group having 1–3 substituents selected from the group consisting of a hydroxyl group, a lower alkoxy-lower alkoxy group, a lower alkyl group which may have a lower alkoxy-lower alkoxy group or a hydroxyl group, a lower alkyl-substituted or unsubstituted amino group, an oxo group and a lower alkyl-substituted or unsubstituted aminocarbonyl group, or having a lower alkylenedioxy group as a substituent, can be exemplified by the above heterocyclic ring groups each having 1–3 substituents selected from the group consisting of a hydroxyl group, an alkoxyalkoxy group whose alkoxy portion is a straight chain or branched chain alkoxy group of 1–6 carbon atoms, a straight chain or branched chain alkyl group of 1–6 carbon atoms which may have, as substituent(s), 1–3 hydroxyl groups or 1–3 alkoxyalkoxy groups whose alkoxy portions are each a straight chain or branched chain alkoxy group of 1–6 carbon atoms, an amino group which may have, as substituent(s), 1–2 straight chain or branched chain alkyl groups each of 1–6 carbon atoms, an oxo group, and an aminocarbonyl group which may have, as substituent(s), 1–2 straight chain or branched chain alkyl groups each of 1–6 carbon atoms, or each having, as a substituent, a straight chain or branched chain alkylenedioxy group of 1–4 carbon atoms, such as 4-hydroxy-1-piperidinyl, 2,6-dimethyl-1-piperidinyl, 4-methylamino-1-piperidinyl, 4,4-ethylenedioxy-1-piperidinyl, 3,4-dihydroxy-1-pyrrolidinyl, 2-methoxymethoxy-methyl-1-pyrrolidinyl, 2-methoxymethoxymethyl-4-hydroxy-1-pyrrolidinyl, 5-methoxymethoxymethyl-2-oxo-1-pyrrolidinyl, 4-(2-methoxymethoxyethyl)-1-piperazinyl, 2-hydroxymethyl-1-pyrrolidinyl, 2-dimethylaminocarbonyl-1-pyrrolidinyl, 2-hydroxymethyl-4-hydroxy-1-pyrrolidinyl, 1,1-dioxo-3,4,5,6-tetrahydro-1,2-thiazin-2-yl, 4-(2-hydroxyethyl)-1-piperazinyl, 4-dimethylamino-1-piperidinyl, 1,1- dioxo-2-isothiazolidinyl, 3-hydroxy-1-pyrrolidinyl, 2-dimethylamino-1-pyrrolidinyl, 4-methoxymethoxy-1-piperidinyl, 4-(2-ethoxyethoxy)-1-piperidinyl, 3-propoxypropoxy-1-pyrrolidinyl, 3-(4-butoxybutoxy)thiomorpholino, 2-(5-pentyloxypentyloxy)morpholino, 3-(6-hexyloxyhexyloxy)-3,4,5,6-tetrahydro-1,2-thiazin-2-yl, 2-oxo-5-hydroxymethyl-1-pyrrolidinyl, 4-methyl-1-piperazinyl, 2,4,6-trimethyl-1-piperidinyl, 3-ethyl-1-pyrrolidinyl, 3-propyl-1-piperazinyl, 3-methylmorpholino, 5-butyl-2-thiomorpholino, 2-amino-1-pyrrolidinyl, 4-(N-methyl-N-propylamino)-1-piperidinyl, 3-dibutylamino-1-piperazinyl, 3-(N-ethyl-N-pentylamino)morpholino, 2-dihexylaminothiomorpholino, 3-dimethyl-aminocarbonyl-1-pyrrolidinyl, 3-methylaminocarbonyl-1-piperidinyl, 2-ethylaminocarbonylmorpholino, 3-propylaminocarbonyl-1-piperazinyl, 3-butylaminocarbonyl-2-thiomorpholino, 3-pentylaminocarbonyl-3,4,5,6-tetrahydro-1,2-thiazin-2-yl, 3-hexylaminocarbonyl-2-isothiazolidinyl, 3-dibutylaminocarbonyl-1-piperazinyl, 4-(N-methyl-N-ethylaminocarbonyl)-1-piperidinyl, 4-hydroxy-2,6-dimethyl-1-piperidinyl, 2-oxo-1-piperazinyl, 3-oxo-1-piperazinyl, 4,4-methylenedioxy-1-piperazinyl and the like.

The above heterocyclic ring group having 1–3 substituents selected from the group consisting of a hydroxyl group, a lower alkoxy-lower alkoxy group, an oxo group, a lower alkyl group which may have a lower alkoxy-lower alkoxy group or a hydroxyl group, and a lower alkyl group-substituted or unsubstituted amino group, or having a lower alkylenedioxy group as a substituent, can be exemplified by the above heterocyclic ring groups each having 1–3 substituents selected from the group consisting of a hydroxyl group, an alkoxyalkoxy group whose alkoxy portion is a straight chain or branched chain alkoxy group of 1–6 carbon atoms, a straight chain or branched chain alkyl group of 1–6 carbon atoms which may have, as substituent(s), 1–3 hydroxyl groups or 1–3 alkoxyalkoxy groups whose alkoxy portions are each a straight chain or branched chain alkoxy group of 1–6 carbon atoms, an amino group which may have 1–2 straight chain or branched chain alkyl groups each of 1–6 carbon atoms, and an oxo group, or each having a straight chain or branched chain alkylenedioxy group of 1–4 carbon atoms as a substituent, such as 4-hydroxy-1-piperidinyl, 2,6-dimethyl-1-piperidinyl, 4-methylamino-1-piperidinyl, 4,4-ethylenedioxy-1-piperidinyl, 3,4-dihydroxy-1-pyrrolidinyl, 2-methoxymethoxymethyl-1-pyrrolidinyl, 2-methoxymethoxymethyl-4-hydroxy-1-pyrrolidinyl, 5-methoxymethoxymethyl-2-oxo-1-pyrrolidinyl, 4-(2-methoxymethoxyethyl)-1-piperazinyl, 2-hydroxymethyl-1-pyrrolidinyl, 2-hydroxymethyl-4-hydroxy-1-pyrrolidinyl, 1,1-dioxo-3,4,5,6-tetrahydro-1,2-thiazin-2-yl, 4-(2-hydroxyethyl)-1-piperazinyl, 4-dimethylamino-1-piperidinyl, 1,1-dioxo-2-isothiazolydinyl, 3-hydroxy-1-pyrrolidinyl, 2-dimethylamino-1-pyrrolidinyl, 4-methoxymethoxy-1-piperidinyl, 4-(2-ethoxyethoxy)-1-piperidinyl, 3-propoxypropoxy-1-pyrrolidinyl, 3-(4-butoxybutoxy)thiomorpholino, 2-(5-pentyloxypentyloxy)morpholino, 3-(6-hexyloxyhexyloxy)-3,4,5,6-tetrahydro-1,2-thiazin-2-yl, 2-oxo-5-hydroxymethyl-1-pyrrolidinyl, 4-methyl-1-piperazinyl, 2,4,6-trimethyl-1-piperidinyl, 3-ethyl-1-pyrrolidinyl, 3-propyl-1-piperazinyl, 3-methylmorpholino, 5-butyl-2-thiomorpholino, 2-amino-1-pyrrolidinyl, 4-(N-methyl-N-propylamino)-1-piperidinyl, 3-dibutylamino-1-piperazinyl, 3-(N-ethyl-N-pentylamino)morpholino, 2-dihexylaminothiomorpholino, 3-dimethylaminocarbonyl-1-pyrrolidinyl, 3-methylaminocarbonyl-1-piperidinyl, 2-ethylaminocarbonylmorpholino, 4-hydroxy-2,6-dimethyl-1-piperidinyl, 2-oxo-1-piperazinyl, 3-oxo-1-piperazinyl, 4,4-methylenedioxy-1-piperazinyl and the like.

The five- or six-membered saturated or unsaturated heterocyclic ring residue containing 1–3 nitrogen atoms, can be exemplified by pyrrolyl, 2H-pyrrolyl, imidazolyl, pyrazolyl, pyridyl, pyridazyl, pyrimidyl, pyrazyl, 2-pyrrolinyl, pyrrolidinyl, 2-imidazolyl, imidazolidinyl, 2-pyrazolinyl, pyrazolidinyl, piperidinyl, piperazinyl, 1,2,4-triazolyl and 1,3,4-triazolyl.

The above heterocyclic ring residue having, as substituent(s), a hydroxyl group, a lower alkoxyalkoxy group, a lower alkoxycarbonyl group or a lower alkyl group which may be substituted with a lower alkoxy-lower alkoxy group or a hydroxyl group, can be exemplified by the above heterocyclic ring residues each having, as substituent(s), a hydroxyl group, an alkoxyalkoxy group whose alkoxy portion is a straight chain or branched chain alkoxy group of 1–6 carbon atoms, a straight chain or branched chain alkoxycarbonyl group of 1–6 carbon atoms, or a straight chain or branched chain alkyl group of 1–6 carbon atoms which may have, as substituent(s), 1–3 hydroxyl groups or 1–3 alkoxyalkoxy groups whose alkoxy portions are each a straight chain or branched chain alkoxy group of 1–6 carbon atoms, such as 4-hydroxy-1-piperidinyl, 3-hydroxy-1-piperidinyl, 2-hydroxy-1-piperidinyl, 2-methoxycarbonyl-1-pyrrolidinyl, s2-methoxymethoxymethyl-1-pyrrolidinyl, 2-(2-methoxymethoxyethyl)-1-imidazolyl, 3-methoxymethoxymethyl-pyrazolyl, 4-(3-ethoxymethoxypropyl)-2-pyrimidyl, 4-methoxymethoxymethyl-2-imidazolin-2-yl, 4-ethoxymethoxymethyl-1-pyrazolidinyl, 2-hydroxymethyl-1-pyrrolidinyl, 2-(2-hydroxyethyl)-1-imidazolyl, 3-ethoxycarbonyl-1,2,4-triazol-1-yl, 3-hydroxy-1-pyrrolyl, 3-ethoxycarbonyl-2H-pyrrolyl, 3-hydroxymethyl-pyrazolyl, 4-hydroxy-2-pyridyl, 4-ethoxycarbonyl-3-pyridazyl, 4-(3-hydroxypropyl)-2-pyrimidyl, 2-propoxycarbonyl-3-pyrazyl, 2-hydroxy-2-pyrrolinin-1-yl, 4-hydroxymethyl- 2-imidazolin-2-yl, 2-methoxycarbonyl-1-imidazolidinyl, 3-methoxymethoxy-1-pyrrolidinyl, 4-(2-ethoxyethoxy)-1-piperidinyl, 4-methoxymethoxy-1-piperidinyl, 3-hydroxy-2-pyrazolin-1-yl, 4-hydroxymethyl-1-pyrazolidinyl, 4-ethoxycarbonyl-1-piperazinyl and the like.

The pyrrolidinyl group having 1–2 substituents selected from the group consisting of a hydroxyl group, a lower alkoxy-lower alkoxy group, a lower alkyl group which may have, as substituent(s), a lower alkoxy-lower alkoxy group or a hydroxyl group, a lower alkoxycarbonyl group, a piperidinylcarbnyl group and a cycloalkyl-lower alkyl group-substituted or unsubstituted aminocarbonyl group, can be exemplified by pyrrolidinyl groups each having 1–2 substituents selected from the group consisting of a hydroxyl group, an alkoxyalkoxy group whose alkoxy portion is a straight chain or branched chain alkoxy group of 1–6 carbon atoms, a straight chain or branched chain alkyl group of 1–6 carbon atoms which may have 1–3 hydroxyl groups or 1–3 alkoxyalkoxy groups whose alkoxy portions are each a straight chain or branched chain alkoxy group of 1–6 carbon atoms, a straight chain or branched chain alkoxycarbonyl group of 1–6 carbon atoms, a piperidinylcarbonyl group and an aminocarbonyl group which may have 1–2 cycloalkylalkyl group of 3–8 carbon atoms whose alkyl portion is a straight chain or branched chain alkyl group of 1–6 carbon atoms, such as 2-methoxymethoxymethyl-1-pyrrolidinyl, 2-methoxymethoxymethyl-4-methoxymethoxy-1-pyrrolidinyl, 3,4-dihydroxy-1-pyrrolidinyl, 3,4-dimethoxymethoxy-1-pyrrolidinyl, 2-hydroxymethyl-1-pyrrolidinyl, 2-methoxycarbonyl-1-pyrrolidinyl, 2-(1-piperidinylcarbonyl)-1-pyrrolidinyl, 2-cyclohexylmethylaminocarbonyl-1-pyrrolidinyl, 4-hydroxy-1-pyrrolidinyl, 2-hydroxymethyl-4-hydroxy-1-pyrrolidinyl, 2-methoxycarbonyl-4-hydroxy-1- pyrrolidinyl, 2-(1-piperidinylcarbonyl)-4-hydroxy-1-pyrrolidinyl, 2-cyclohexylmethylaminocarbonyl-4-hydroxy-1-pyrrolidinyl, 3-ethoxycarbonyl-1-pyrrolidinyl, 2-propoxycarbonyl-1-pyrrolidinyl, 3-butoxycarbonyl-1-pyrrolidinyl, 2-pentyloxycarbonyl-1-pyrrolidinyl, 3-hexyloxycarbonyl-1-pyrrolidinyl, 2-hydroxy-1-pyrrolidinyl, 3-hydroxy-1-pyrrolidinyl, 2-cycloheptylmethylaminocarbonyl-1-pyrrolidinyl, 3-cyclooctylmethylaminocarbonyl-1-pyrrolidinyl, 2-cyclopentylmethylaminocarbonyl-1-pyrrolidinyl, 3-cyclopropylmethylaminocarbonyl-1-pyrrolidinyl, 2-cyclobutylmethylaminocarbonyl-1-pyrrolidinyl, 2-(1-piperidinylcarbonyl)-4-methoxycarbonyl-1-pyrrolidinyl, 2-cyclohexylaminocarbonyl-4-methyl-1-pyrrolidinyl, 2-ethyl-4-hydroxy-1-pyrrolidinyl, 4-propyl-1-pyrrolidinyl, 2-hydroxymethyl-4-methoxymethoxy-1-pyrrolidinyl, 2-methoxycarbonyl-4-(2-ethoxyethoxy)-1-pyrrolidinyl, 2-(1-piperidinylcarbonyl)-4-propoxymethoxy-1-pyrrolidinyl, 2-cyclohexylmethylaminocarbonyl- 4-butoxymethoxy-1-pyrrolidinyl and the like.

As to the lower alkoxy-lower alkoxy group, there can be mentioned, for example, alkoxyalkoxy groups whose alkoxy portions are each a straight chain or branched chain alkoxy group of 1–6 carbon atoms, such as methoxymethoxy, 3-methoxypropoxy, 4-ethoxybutoxy, 4-propoxyhexyloxy, 5-isopropoxypentyloxy, 1,1-dimethyl-2-butoxyethoxy, 2-methyl-tert-butoxypropoxy, 2-pentyloxyethoxy, hexyloxymethoxy and the like.

As to the halogen atom, there can be mentioned, for example, a fluorine atom, a chlorine atom, a bromine atom and an iodine atom.

The carbostyril derivative represented by the above general formula (1) can be produced by various processes. It can be easily produced by, for example, the processes shown by the following reaction formulas.

[Reaction formula-1]

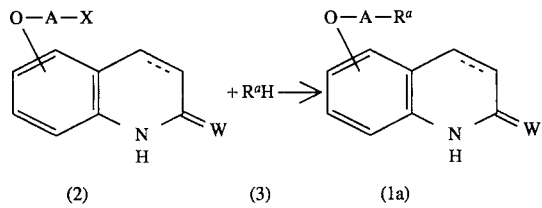

(2)    (3)    (1a)

[wherein A, W and the carbon-to-carbon bond between the 3- and 4-positions of the carbostyril skeleton have the same definitions as given above. $R^a$ represents a group

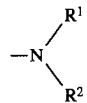

(wherein $R^1$ and $R^2$ have the same definitions as given above.). X represents a halogen atom, a lower alkanesulfonyloxy group, an arylsulfonyloxy group or an aralkylsulfonyloxy group.]

The reaction between a compound of general formula (2) and a compound of general formula (3) is conducted in an appropriate solvent or in the absence of any solvent, in the presence or absence of a basic compound. The reaction is conducted generally at room temperature to 200° C., preferably at room temperature to 150° C., and is complete generally in about 1–30 hours. The solvent used can be exemplified by ethers such as dioxane, tetrahydrofuran, ethylene glycol dimethyl ether, diethyl ether and the like; aromatic hydrocarbons such as benzene, toluene, xylene and the like; halogenated hydrocarbons such as dichloromethane, chloroform, carbon tetrachloride and the like; lower alcohols such as methanol, ethanol, isopropanol and the like; polar solvents such as dimethylformamide (DMF), dimethyl sulfoxide (DMSO), hexamethylphosphoric triamide, pyridine, acetone, actonitrile and the like. The basic compound used can be exemplified by inorganic bases such as potassium carbonate, sodium carbonate, sodium hydroxide, potassium hydroxide, sodium hydrogencarbonate, potassium hydrogencarbonate, sodium amide, sodium hydride, potassium hydride and the like; and organic bases such as triethylamine, tripropylamine, pyridine, quinoline and the like. The above reaction proceeds advantageously when an alkali metal iodide (e.g. potassium iodide or sodium iodide) or the like is added to the reaction system. The compound of general formula (3) is added in an amount of generally at least 1 mole, preferably 1–8 moles per mole of the compound of general formula (2).

In the reaction formula 1, the lower alkanesulfonyloxy group represented by X can be exemplified by methanesulfonyloxy, ethanesulfonyloxy, isopropanesulfonyloxy, propanesulfonyloxy, butanesulfonyloxy, tert-butanesulfonyloxy, pentanesulfonyloxy and hexanesulfonyloxy. The arylsulfonyloxy group can be exemplified by substituted or unsubstituted arylsulfonyloxy groups such as phenylsulfonyloxy, 4-methylphenylsulfonyloxy, 2-methylphenylsulfonyloxy, 4-nitrophenylsulfonyloxy, 4-methoxyphenylsulfonyloxy, 3-chlorophenylsulfonyloxy, α-naphthylphenylsulfonyloxy and the like. The aralkylsulfonyloxy group can be exemplified by substituted or unsubstituted aralkylsulfonyloxy groups such as benzylsulfonyloxy, 2-phenylethylsulfonyloxy, 4-phenylbutylsulfonyloxy, 4-methylbenzylsulfonyloxy, 2-methylbenzylsulfonyloxy, 4-nitrobenzylsulfonyloxy, 4-methoxybenzylsulfonyloxy, 3-chlorobenzylsulfonyloxy, α-naphthylmethylsulfonyloxy and the like.

[Reaction formula-2]

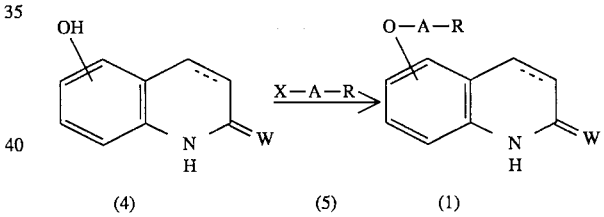

(4)    (5)    (1)

[wherein W, X, A, R and the carbon-to-carbon bond between the 3- and 4-positions of the carbostyril skeleton have the same definitions as given above.].

The reaction between a compound of general formula (4) and a Compound of general formula (5) is conducted in an appropriate solvent, preferably using a basic compound as a dehalogenating agent, generally at room temperature to 200° C., preferably at 50°–150° C. in about 1–30 hours. The appropriate solvent can be exemplified by lower alcohols such as methanol, ethanol, isopropanol and the like; ketones such as acetone, methyl ethyl ketone and the like; ethers such as diethyl ether, dioxane, diethylene glycol dimethyl ether and the like; aromatic hydrocarbons such as toluene, xylene and the like; DMF; DMSO; and hexamethylphosphoric triamide. The basic compound usable as a dehalogenating agent can be exemplified by inorganic bases such as sodium hydroxide, potassium hydroxide, sodium carbonate, potassium carbonate, sodium methoxide, sodium ethoxide, potassium ethoxide, sodium hydroxide, metallic potassium, sodium amide and the like; and organic bases such as pyridine, quinoline, triethylamine, tripropylamine and the like. In the reaction, it is possible to add, as a reaction accelerator, an alkali metal iodide (e.g. potassium iodide or sodium iodide) to the reaction system. The amount of the compound of general formula (5) used has no restriction, but the compound is used in an amount of generally 1–5 moles, preferably 1–2 moles per mole of the compound of general formula (4).

[Reaction formula-3]

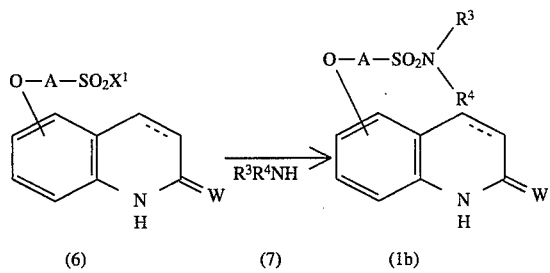

[wherein A, W, $R^3$, $R^4$ and the carbon-to-carbon bond between the 3- and 4-positions of the carbostyril skeleton have the same definitions as given above. $X^1$ represents a halogen atom.].

The reaction between a compound (6) and a compound (7) can be conducted under the same conditions as employed in the reaction between the compound (2) and the compound (3) shown in the Reaction formula-1.

[Reaction formula-4]

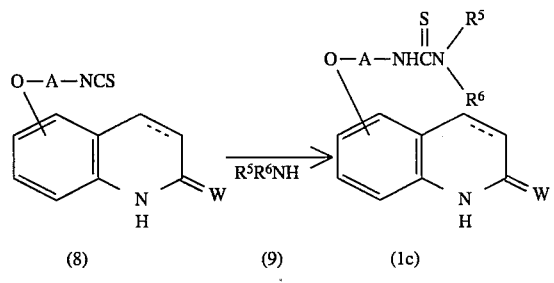

[wherein A, W, $R^5$, $R^6$ and the carbon-to-carbon bond between the 3- and 4-positions of the carbostyril skeleton have the same definitions as given above.].

The reaction between a compound (8) and a compound (9) is conducted in the same solvent as used in the reaction between the compound (2) and the compound (3) shown in the reaction formula 1, generally at room temperature to 100° C., preferably at room temperature to about 70° C., and is complete generally in about 0.5–5 hours. The amount of the amine (9) used is generally 1–2 moles, preferably 1–1.5 moles per mole of the compound (8).

[Reaction formula-5]

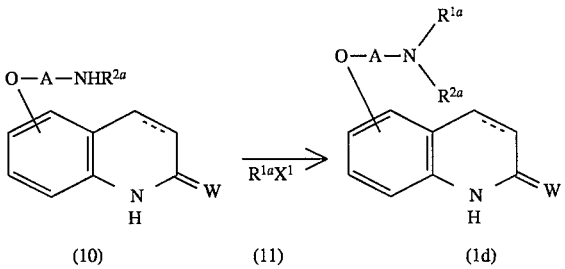

[wherein A, W, $R^2$, $X^1$ and the carbon-to-carbon bond between the 3- and 4-positions of the carbostyril skeleton have the same definitions as given above. $R^{1a}$ represents a group

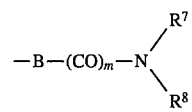

(B, m, $R^7$ and $R^8$ have the same definitions as given above.); a lower alkoxycarbonyl-substituted lower alkyl group; a carboxy group-substituted lower alkyl group; a lower allyl group having as a substituent, a lower alkyl group-substituted or unsubstituted aminocarbonyl group; a hydroxyl group-containing lower alkyl group; an imidazolyl-substituted lower alkyl group; a pyridyl-substituted lower alkyl group; pyrrolidinyl-lower alkyl group which may have, as substituent(s) on the pyrrolidine ring, 1–3 groups selected from the group consisting of a lower alkyl group, a lower alkoxy-lower alkoxy group and a hydroxyl group; or a group —$SO_2D$—$R^9$ (wherein D and $R^9$ have the same definitions as given above.). $R^{2a}$ represents $R^2$ other than the case $R^2$ and $R^1$ form a pyrrolidinyl group together with the nitrogen atom to which $R^2$ and $R^1$ bond.].

The reaction between a compound (10) and a compound (11) can be conducted under the same conditions as employed in the reaction between the compound (2) and the compound (3) shown in the Reaction formula 1.

[Reaction formula-6]

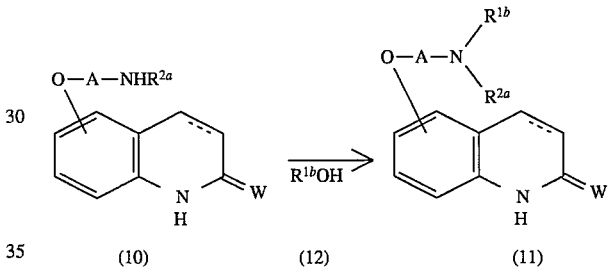

[wherein A, W, $R^{2a}$ and the carbon-to-carbon bond between the 3- and 4-positions of the carbostyril skeleton have the same definitions as given above. $R^{1b}$ represents a group —CO—B—$(CO)_m$—$NR^7R^8$ (wherein B, m, $R^7$ and $R^8$ have the same definitions as given above.].

The reaction between a compound of general formula (10) and a compound of general formula (12) is conducted in accordance with an ordinary amide bond formation reaction. In the amide bond formation reaction, there can be easily used known processes for amide bond formation reaction. For example, there can be mentioned, (a) a mixed acid anhydride process which comprises reacting a carboxylic acid (12) with an alkylhalocarboxylic acid to obtain a mixed acid anhydride and reacting the anhydride with an amine (10); (b) an active ester process which comprises converting a carboxylic acid (12) to an active ester such as p-nitrophenyl ester, N-hydroxysuccinimide ester, 1-hydroxybenzotriazole ester or the like, and reacting the active ester with an amine (10); (c) a carbodiimide process which comprises subjecting a carboxylic acid (12) and an amine (10) to condensation in the presence of an activating agent such as dicyclohexylcarbodiimide, carbonyldiimidazole or the like; and (d) other processes, for example, a process which comprises converting a carboxylic acid (12) to a carboxylic acid anhydride using a dehydrating agent such as acetic anhydride or the like and reacting the anhydride with an amine (10), a process which comprises reacting a carboxylic acid (12) with a lower alcohol to form an ester and reacting the ester with an amine (10) at a high pressure and at a high temperature, and a process which comprises converting a carboxylic acid (12) to an acid halide (a carboxylic acid halide) and reacting the halide with an amine (10).

In the mixed acid anhydride process, the mixed acid anhydride is obtained by an ordinary Schoten-Baumann reaction and it is reacted with the amine (10) generally without being isolated, to obtain a compound of general formula (1f). The Schotten-Baumann reaction is conducted in the presence of a basic compound. The basic compound can be any of those generally used in the Schotten-Baumann reaction, and includes, for example, organic bases such as potassium carbonate, triethylamine, trimethylamine, pyridine, dimethylaniline, N-methylmorpholine, 1,5-diazabicyclo[4.3.0]nonene-5 (DBN), 1,8-diazabicyclo[5.4.0]undecene-7 (DBU), 1,4-diazabicyclo[2.2.2]octane (DABCO) and the like, and inorganic bases such as sodium carbonate, potassium hydrogencarbonate, sodium hydrogencarbonate and the like. The reaction is conducted generally at about $-20°$ to $100°$ C., preferably at about $-0°–50°$ C., and is complete in 5 minutes to 10 hours, preferably 5 minutes to 2 hours. The reaction of the thus obtained mixed acid anhydride with the amine (10) is conducted generally at about $-20°$ to $150°$ C., preferably at about $10°–50°$ C., and is complete in 5 minutes to 10 hours, preferably 5 minutes to 5 hours. The mixed acid anhydride process is conducted generally in a solvent. Any solvent generally used in the mixed acid anhydride process can be used. Specific examples of the solvent are halogenated hydrocarbons such as methylene chloride, chloroform, dichloroethane and the like; aromatic hydrocarbons such as benzene, toluene, xylene and the like; ethers such as diethyl ether, tetrahydrofuran, dimethoxyethane and the like; esters such as methyl acetate, ethyl acetate and the like; and aprotic polar solvents such as DMF, DMSO, hexamethylphorphoric triamide and the like. The alkylhalocarboxylic acid used in the mixed acid anhydride process includes, for example, methyl chloroformate, methyl bromoformate, methyl chloroformate, ethyl bromoformate and isobutyl chloroformate. In the process, the proportions of carboxylic acid (12), alkylhalocarboxylic acid and amine (10) used are generally each 1 mole, but the first and second compounds are preferably used each in an amount of 1–1.5 moles per mole of the amine (10).

When there is used the process which comprises reacting a carboxylic acid halide with an amine (10), the reaction is conducted in an appropriate solvent in the presence of a basic compound. As to the basic compound, there can be widely used known compounds. They include, for example, the basic compounds used in the above Schotten-Baumann reaction, sodium hydroxide, potassium hydroxde, sodium hydride, potassium hydride, silver carbonate and alcoholates (e.g. sodium methylate, sodium ethylate). The solvent includes, for example, the solvents usable in the above mixed acid anhydride process, alcohols (e.g. methanol, ethanol, propanol, butanol, 3-methoxy-1-butanol, ethyl celloslve, methyl cellosolve), pyridine, acetone, acetonitrile and mixtures thereof. The proportions of the amine (10) and the carboxylic acid halide used are not critical and can be selected in wide ranges, but the latter is used in an amount of generally about 1 mole, preferably about 1–5 moles per mole of the former. The reaction is conducted generally at about $-30°$ to $180°$ C., preferably at about $0°–150°$ C., and is complete generally in about 5 minutes to 30 hours.

[Reaction formula-7]

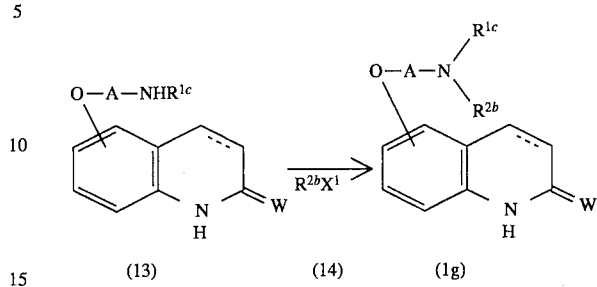

(13)  (14)  (1g)

[wherein A, W, X and the carbon-to-carbon bond between the 3-and 4-positions of the carbostyril skeleton have the same definitions as given above. $R^{2b}$ represents a cycloalkyl-lower alkyl group; a cycloalkyl group; a phenyl group; a phenyl-lower alkyl group which may have, as substituent(s) on the phenyl ring, 1–3 groups selected from the group consisting of a halgoen atom, a lower alkyl group, a cyano group, a carboxy group and a lower alkoxy group; a pyrrolidyl-substituted alkyl group; a thienyl-substituted lower alkyl group; a tetrahydropyranyl-substituted lower alkyl group; a phenyl-lower alkylsulfonyl group; a phenylsulfonyl group; or acycloalkyl-lower alkylsulfonyl group. $R^{1c}$ represents the above-mentioned $R^{1a}$ and $R^{1b}$.].

The reaction between a compound (13) and a compound (14) can be conducted under the same conditions as employed in the reaction between the compound (2) and the compound (3) shown in the Reaction formula-1.

[Reaction formula -8]

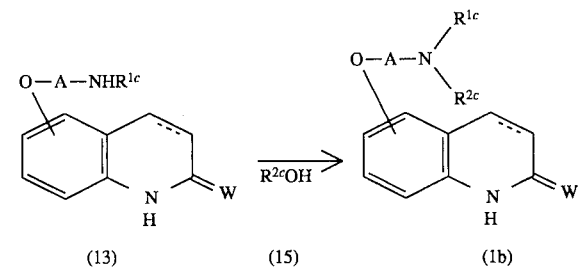

(13)  (15)  (1b)

[wherein A, W, $R^{1c}$ and the carbon-to-carbon bond between the 3- and 4-positions of the carbostyril skeleton have the same definitions as given above. $R^{2c}$ represents a cycloalkylcarbonyl group or a benzoyl group.].

The reaction between a compound (13) and a compound (15) can be conducted under the same conditions as employed in the reaction between the compound (10) and the compound (12) shown in the Reaction formula-6.

[Reaction formula -9]

-continued

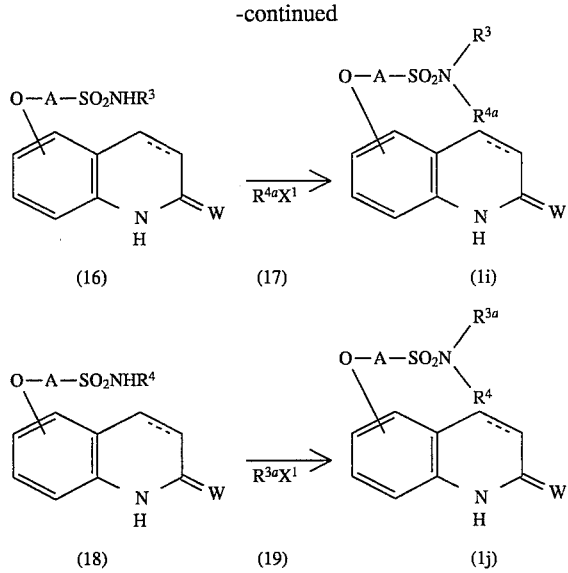

[wherein A, W, $X^1$, $R^3$, $R^4$ and the carbon-to-carbon bond between the 3- and 4-positions of the carbostyril skeleton have the same definitions as given above. $R^{3a}$ represents the above-mentioned $R^3$ other than the case $R^3$ is a hydrogen atom. $R^{4a}$ represents the above-mentioned $R^{4a}$ other than the case $R^4$ is a hydrogen atom.].

The reaction between a compound (16) and a compound (17) and the reaction between a compound (18) and a compound (19) can be conducted under the same conditions as employed in the reaction between the compound (2) and the compound (3) shown in the Reaction formula-1.

[Reaction formula -10]

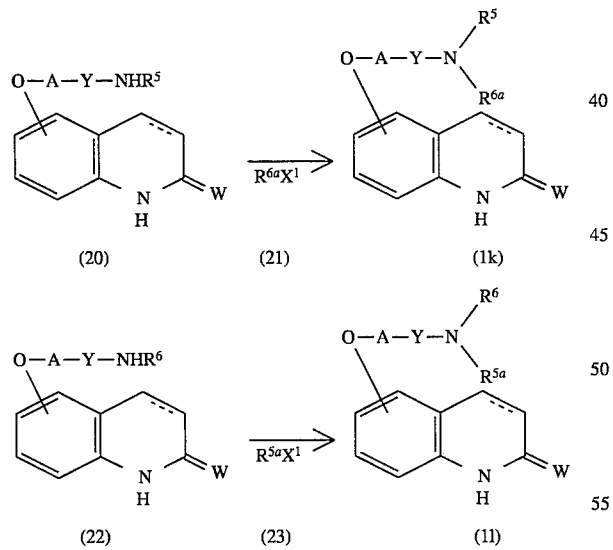

[wherein A, W, Y, $R^5$, $R^6$ and the carbon-to-carbon bond between the 3- and 4-positions of the carbostyril skeleton have the same definitions as given above. $R^{5a}$ represents the above-mentioned $R^5$ other than the cace $R^5$ is a hydrogen atom, and $R^{6a}$ represents the above-mentioned $R^6$ other than the cace $R^6$ is a hydrogen atom.].

The reaction between a compound (20) and a compound (21) and the reaction between a compound (22) and a compound (23) can be conducted under the same conditions as employed in the reaction between the compound (2) and the compound (3) shown in the Reaction formula-2.

[Reaction formula -11]

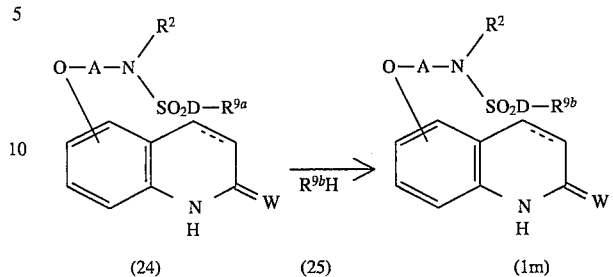

[wherein A, W, $R^2$, D and the carbon-to-carbon bond between the 3- and 4-positions of the carbostyril skeleton have the same definitions as given above. $R^{9a}$ represents a halogen atom. $R^{9b}$ represents a five- or six-membered saturated or unsaturated heterocyclic ring residue containing 1–3 nitrogen atoms, which residue may have, as substituent(s), a hydroxyl group, a lower alkoxy-lower alkoxy group, a lower alkoxycarbonyl group or a lower alkyl group which may be substituted with a lower alkoxy-lower alkoxy group or a hydroxyl group.].

The reaction between a compound (24) and a compound (25) can be conducted under the same conditions as employed in the reaction between the compound (2) and the compound (3) shown in the Reaction formula-1.

[Reaction formula -12]

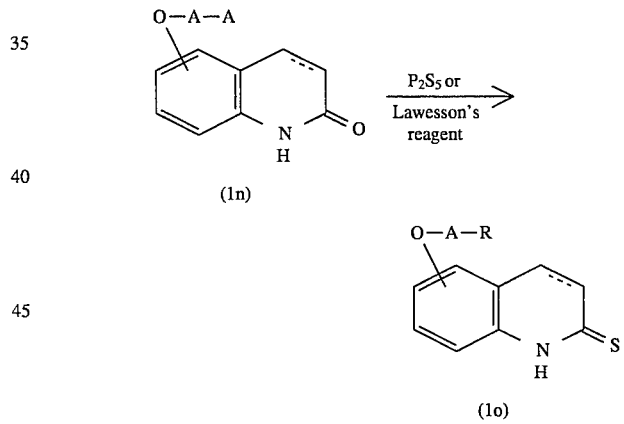

[wherein A, R and the carbon-to-carbon bond between the 3- and 4-positions of the carbostyril skeleton have the same definitions as given above.].

The reaction between a compound (1n) and phosphorus pentasulfide or a Lawesson's reagent represented by the formula,

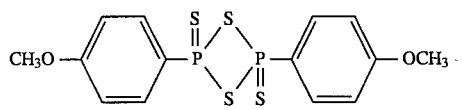

is conducted in an ordinary inert solvent such as aromatic hydrocarbon (e.g. benzene, toluene, xylene, chlorobenzene), ether (e.g. diethyl ether, tetrahydrofuran, dioxane), halogenated hydrocarbon (e.g. methylene chloride, chloroform), dimethyl sulfoxide, hexamethylphosphoric triamide or the like. The amount of phosphorus pentasulfide or Lawesson's reagent used is generally 0.2 mole to a large excess, preferably 0.4–2 moles per mole of the compound (1n). The reaction temperature is generally room temperature to 200° C., preferably 50°–150° C., and the reaction time is 0.5–50 hours.

[Reaction formula -13]

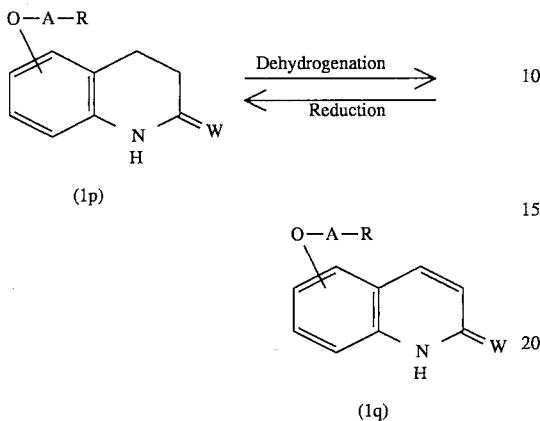

[wherein A, W and R have the same definitions as given above.].

The reduction of a compound of general formula (1q) is conducted under the conditions of ordinary catalytic reduction. The catalyst used can be exemplified by metals such as palladium, palladium-carbon, platinum, Raney nickel and the like. Such a metal is used preferably in an ordinary catalytic amount. The solvent used includes, for example, alcohols such as methanol, ethanol, isopropanol and the like; ethers such as dioxane, tetrahydrofuran and the like; aliphatic hydrocarbons such as hexane, cyclohexane and the like; esters such as ethyl acetate and the like; and fatty acids such as acetic acid and the-like. The reduction can be conducted at atmospheric pressure or under pressure, but is conducted generally at about atmospheric pressure to 20 kg/cm$^2$, preferably at atmospheric pressure to 10 kg/cm$^2$. The reaction temperature is generally about 0°–150° C., preferably about room temperature to 100° C.

The dehydrogenation of a compound of general formula (1p) is conducted in an appropriate solvent, using an oxidizing agent. The oxidizing agent includes, for example, benzoquinones such as 2,3-dichloro-5,6-dicyanobenzoquinone, chloranil (2,3,5,6-tetrachlorobenzoquinone) and the like; halogenating agents such as N-bromosuccinimide, N-chlorosuccinimide, bromine and the like; selenium dioxide; palladium-carbon; palladium black; palladium oxide; and hydrogenation catalysts such as Raney nickel and the like. The amount of the halogenating agent used is not critical and can be approprately selected from a wide range, but is used in an amount of generally about 1–5 moles, preferably about 1–2 moles per mole of the compound of general formula (1p). When a hydrogenation catalyst is used, it is used in an ordinary catalystic amount. The solvent can be exemplified by ethers such as dioxane, tetrahydrofuran, methoxyethanol, dimethoxyethane and the like; aromatic hydrocarbons such as benzene, toluene, xylene, cumene and the like; halogenated hydrocarbons such as dichloromethane, dichloroethane, chloroform, carbon tetrachloride and the like; alcohols such as butanol, amyl alcohol, hexanol and the like; polar protonic solvents such as acetic acid and the like; and polar aprotic solvents such as dimethylformamide, dimethyl sulfoxide, hexamethylphosphoric triamide and the like. The reaction is conducted generally at about room temperature to 300° C., preferably at about room temperature to 200° C. and is complete generally in 1–40 hours.

The compounds (3), (7) and (9) each as starting material can be easily produced by, for example, the processes shown by the following reaction formulas.

[Reaction formula-14]

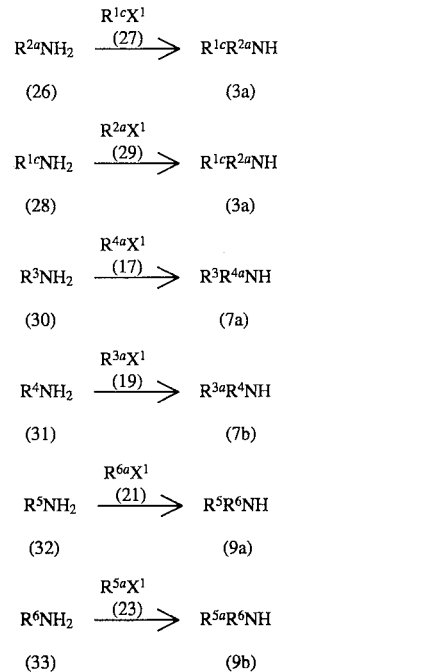

[wherein $R^{2a}$, $R^{1c}$, $R^{4a}$, $R^{3a}$, $R^{6a}$, $R^{5a}$, $R^3$, $R^4$, $R^5$, $R^6$ and $X^1$ have the same definitions as given above.].

The reaction between a compound (26) and a compound (27), the reaction between a compound (28) and a compound (29), the reaction between a compound (30) and a compound (17), the reaction between between a compound (31) and a compound (19), the reaction between a compound (32) and a compound (21) and the reaction between a compound (33) and a compound (23) can be conducted under the same conditions as employed in the reaction between the compound (2) and the compound (3) shown in the Reaction formula-1.

[Reaction formula-15]

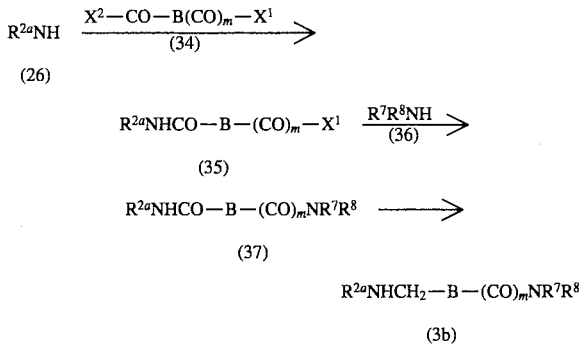

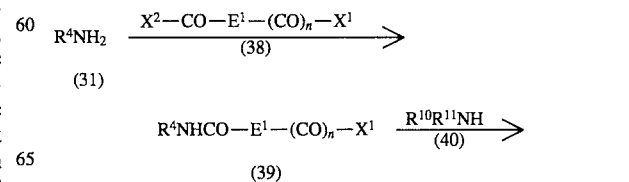

-continued

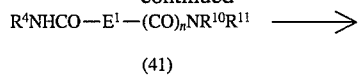

(41)

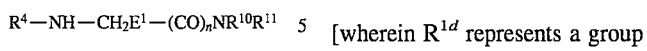

(7c)

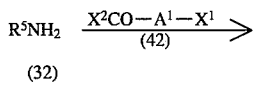

(32)

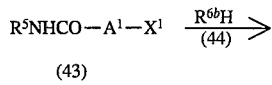

(43)

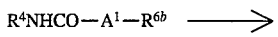

(45)

$$R^4\text{—NHCH}_2\text{—}A^1\text{—}R^{6b}$$

(9c)

wherein $R^{2a}$, B, m, $X^1$, $R^7$, $R^8$, $R^4$, $R^{10}$, $R^{11}$ and $R^5$ have the same definitions as given above. $X^2$ represents a halogen atom. $E^1$ represents a hydroxyl group-substituted or unsubstituted lower alkylene group. $A^1$ represents a lower alkylene group. $R^{6b}$ represents a piperidinyl group which may have a lower alkoxy-lower alkoxy group or a hydroxyl group as a substituent on the piperidinyl ring.].

The reaction between a compound (26) and a compound (34), the reaction between a compound (31) and a compound (38) and the reaction between a compound (32) and a compound (42) can be conducted under the same conditions as employed in the reaction between the compound (2) and the compound (3) shown in the Reaction formula-1. The reaction between a compound (35) and a compound (37), the reaction between a compound (39) and a compound (40) and the reaction between a compound (43) and a compound (44) can also be conducted under the same conditions as employed in the reaction between the compound (2) and the compound (3) shown in the Reaction formula-1.

The reduction of a compound (37), (41) or (45) is conducted in an appropriate solvent in the presence of a hydride and reducing agent. The reducing agent includes, for example, sodium boron hydride, lithium aluminum hydride and diborane. The amount of reducing agent used is at least about 1 mole , preferably about 1–3 moles per mole of the starting material. When lithium aluminum hydride is used as the reducing agent, it is used in an amount of preferably about the same weight as that of the starting material. The solvent includes, for example, water; alcohols such as methanol, ethanol, isopropanol and the like; and ethers such as tetrahydrofuran, diethyl ether, diglyme and the like. The reaction is conducted generally at about −60° C. to 150° C., preferably at about −30° C. to 100° C., and is complete generally in about 10 minutes to 15 hours. When lithium aluminum hydride or diborane is used as the reducing agent, an anhydrous solvent such as diethyl ether, 10 tetrahydrofuran, diglyme or the like is used preferably.

[Reaction formula-16]

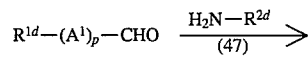

(46)

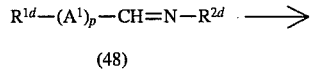

(48)

-continued

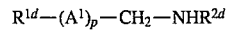

(3c)

[wherein $R^{1d}$ represents a group

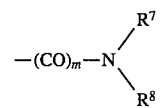

(m, $R^7$ and $R^8$ have the same definitions as given above.), a lower alkoxycarbonyl group, a carboxy group, a lower alkyl group-substituted or unsubstituted aminocarbonyl group, a hydroxyl group, an imidazolyl group, a pyridyl group or a pyrrolidinyl group which may have, as substituent(s) on the pyrrolidine ring, 1–3 groups selected from the group consisting of a lower alkyl group, a lower alkoxy-lower alkoxy group and a hydroxyl group. p represents 0 or 1. $R^{2d}$ represents a cycloalkyl-lower alkyl group, a cycloalkyl group, a phenyl group, a phenyl-lower alkyl group which may have, as substituent(s) on the phenyl ring, 1–3 groups selected from the group consisting of a halogen atom, a lower alkyl group, a cyano group, acarboxy group and a lower alkoxy group, a pyridyl-substituted lower alkyl group, a thienyl-substituted lower alkyl group, a cycloalkylcarbonyl group, a benzoyl group, a tetrahydropyranyl-substituted lower alkyl group, a phenyl-lower alkylsulfonyl group, a phenylsulfonyl group or a cycloalkyl-lower alkylsulfonyl group. $A^1$ has the same definition as given above.].

The reaction between a compound of general formula (46) and a compound of general formula (47) is conducted in an appropriate solvent or in the absence of any solvent in the presence or absence of a dehydrating agent. The solvent includes, for example, alcohols such as methanol, ethanol, isopropanol and the like; aromatic hydrocarbons such as benzene, toluene, xylene and the like; and aprotic polar solvents such as dimethylformamide, dimethylacetamide, N-methylpyrrolidone and the like. The dehydrating agent includes, for example, drying agents ordinarily used in dehydration of solvent, such as molecular sieve and the like; mineral acids such as hydrochloric acid, sulfuric acid, boron trifluoride and the like; and organic acids such as p-toluenesulfonic acid and the like. The reaction is conducted generally at about room temperature to 200° C., preferably at about room temperature to 150° C., and is complete generally in about 1–48 hours. The amount of the compound of general formula (47) used is not critical, but is generally at least about 1 mole , preferably about 1–15 moles per mole of the compound of general formula (46). The amount of the dehydrating agent used is generally a large excess when a dryng agent is used, and is a catalytic amount when an acid used. The thus obtained compound of general formula (48) is used in the subsequent reduction without being isolated.

The reduction of the compound of general formula (48) can be conducted by various methods. For example, there is preferably used a method using a hydride reducing agent. The hydride and reducing agent includes, for example, lithium aluminum hydride, sodium boron hydride and diborane. The amount of the reducing agent used is at least about 1 mole , preferably about 1–10 moles per mole of the compound of general formula (48). The reduction is conducted generally in an appropriate solvent such as water, lower alcohol (e.g. methanol, ethanol, isopropanol), ether (e.g. tetrahydrofuran, diethyl ether, diglyme) or the like, generally at about −60° C. to 50° C., preferably at about −30° C. to room temperature for about 10 minutes to 5 hours. An anhydrous solvent such as diethyl ether, tetrahydrofuran, diglyme or the like is preferably used when there is used, as the reducing agent, lithium aluminum hydride or diborane.

The reduction of the compound of general formula (48) can be conducted also by subjecting the compound to catalytic hydrogenation in the presence of a catalyst in an appropriate solvent. The solvent includes, for example, water; acetic acid; alcohols such as methanol, ethanol, isopropanol and the like; hydrocarbons such as hexane, cyclohexane and the like; ethers such as dioxane, tetrahydrofuran, diethyl ether, ethylene glycol dimethyl ether and the like; esters such as ethyl acetate, methyl acetate and the like; and aprotic polar solvents such as dimethylformamide and the like. The catalyst includes, for example, palladium, palladium black, palladium-carbon, platinum, platinum oxide, copper chromite and Raney nickel. The amount of the catalyst used is generally about 0.02–1 time the amount of the compound of general formula (48). The reaction temperature is generally at about –20° C. to 150° C., preferably at about 0°–100° C.; the hydrogen pressure is generally about 1–10 atm; and the reaction is complete generally in about 0.5–10 hours.

[Reaction formula-17]

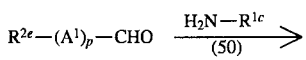

(49)

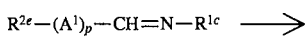

(51)

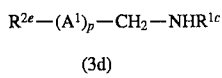

(3d)

[wherein $A^1$ and p are the same as defined above; $R^{2e}$ represents a cycloalkyl group, a phenyl group which may have, as substituent(s) on the phenyl ring, 1–3 groups selected from the group consisting of a halogen atom, a lower alkyl group, a cyano group, a carboxy group and a lower alkoxy group, a pyridyl group, a thienyl group or a tetrahydropyranyl group. $R^{1c}$ has the same definition as given above.].

The reaction between a compound (49) and a compound (50) can be conducted under the same conditions as employed in the reaction between the compound (46) and the compound (47) shown in the reaction formula 16.

The reaction for converting a compound (51) to a compound (3d) can be conducted under the same conditions as employed in the reaction for converting the compound (48) to the compound (3c).

[Reaction formula -18]

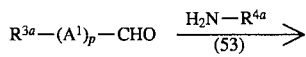

(52)

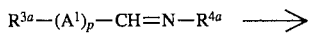

(54)

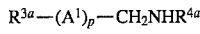

(7d)

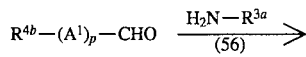

(55)

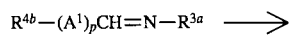

(57)

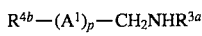

(7e)

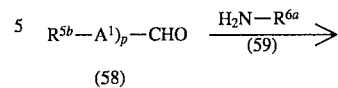

(58)

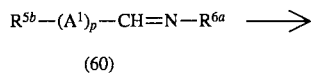

(60)

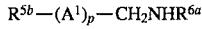

(9d)

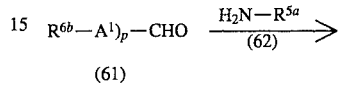

(61)

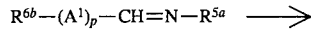

(63)

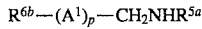

(9e)

[wherein $R^{3a}$, $A^1$, $R^{4a}$, $R^{5a}$ and $R^{6a}$ and have the same definitions as given above. $R^{4b}$ represents a cycloalkyl group, a phenyl group which may have, as substituent(s) on the phenyl ring, 1–3 groups selected from the group consisting of a halogen atom, a lower alkyl group and a lower alkoxy group, a thienyl group, a pyridyl group, an imidazolyl group or a tetrahydropyranyl group. $R^{5b}$ and $R^{6b}$ independently represent a hydrogen atom, a cycloalkyl group or a piperidinyl group which may have a lower alkoxy-lower alkoxy group or a hydroxyl group as a substituent on the piperidinyl ring.].

The reaction between a compound (52) and a compound (53), the reaction between a compound (55) and a compound (56), the reaction between a compound (58) and a compound (59) and the reaction between a compound (61) and a compound (62) can be conducted under the same conditions as employed in the reaction between the compound (46) and the compound (47) shown in the Reaction formula-16.

The reaction for converting a compound (54) to a compound (7d), the reaction for converting a compound (57) to a compound (7e), the reaction for converting a compound (60) to a compound (9d) and the reaction for converting a compound (63) to a compound (9e) can be conducted under the same conditions as employed in the reaction for converting the compound (48) to the compound (3c) shown in the Reaction formula-16.

[Reaction formula-19]

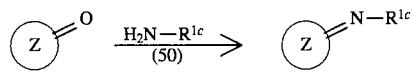

(64)            (65)

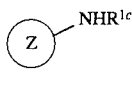

(3e)

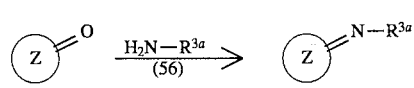

(64)            (66)

-continued

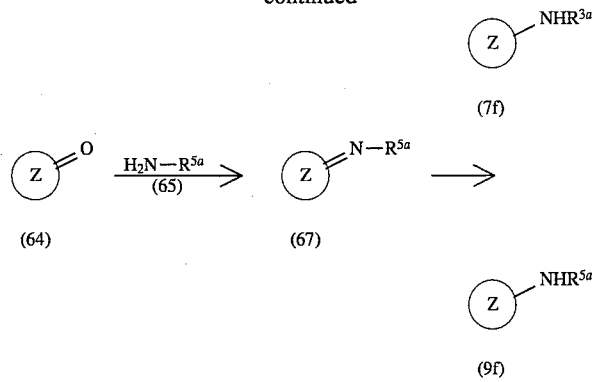

[wherein Ⓩ represents a cycloalkyl group $R^{1c}$, $R^{3a}$ and $R^{5a}$ have the same definitions as given above.].

The reaction between a compound (64) and a compound (50), the reaction between a compound (64) and a compound (56) and the reaction between a compound (64) and a compound (62) can be conducted under the same conditions as employed in the reaction between the compound (46) and the compound (47) shown in the Reaction formula-16.

The reaction for converting a compound (65) to a compound (3e), the reaction for converting a compound (66) to a compound (7f) and the reaction for converting a compound (67) to a compound (9f) can be conducted under the same conditions as employed in the reaction for converting the compound (48) to the compound (3c) shown in the Reaction formula-16).

The compound (5) used as a starting material can be produced by, for example, the following processes.

[Reaction formula -20]

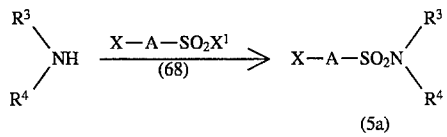

[wherein $R^3$, $R^4$, X, A and $X^1$ have the same definitions as given above.].

The reaction between a compound (7) and a compound (68) can be conducted under the same conditions as employed in the reaction between the compound (2) and the compound (3) shown in the Reaction formula-1.

[Reaction formula-21]

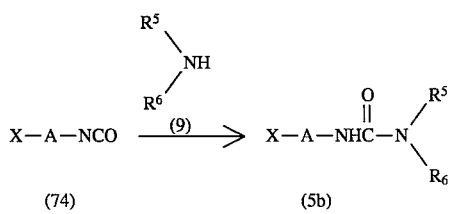

[wherein X, A, $R^5$ and $R^6$ have the same definitions as given above.].

The reaction between a compound (74) and a compound (9) can be conducted under the same conditions as employed in the reaction between the compound (8) and the compound (9) shown in the Reaction formula-4.

[Reaction formula -22]

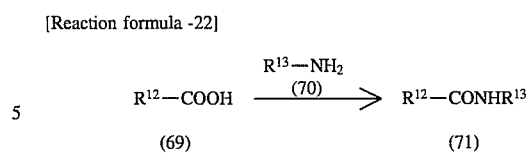

[wherein $R^{12}$ represents a pyrrolidinyl group which may have, as a substituent, a hydroxyl group, a lower alkoxy-lower alkoxy group, a lower alkyl group which may be substituted with a lower alkoxy-lower alkoxy group or a hydroxyl group, a lower alkoxycarbonyl group, a piperidinylcarbonyl group or an aminocarbonyl group which may be substituted with a cycloalkyl-lower alkyl group. $R^{13}$ represents a cycloalkyl-lower alkyl group or a hydrogen atom.].

The reaction between a compound (69) and a compound (70) can be conducted under the same conditions as employed in the reaction between the compound (10) and the compound (12) shown in the reaction formula 6. In the reaction, it is possible to protect the 1-position of the pyrrolidine ring with a protecting group, for example, a phenyl-lower alkoxycarbonyl group (e.g. a benzyloxycarbonyl group), react the protected compound with a compound (70) and reduce the reaction product under the same conditions as employed in the reduction of the compound (48) by catalytic hydrogenation, shown in the Reaction formula-16, to conduct deprotection.

[Reaction formula-23]

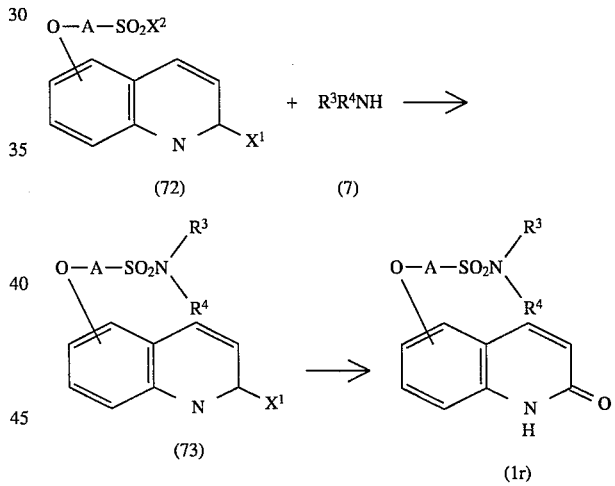

[wherein $X^1$, X, A, $R^3$ and $R^4$ have the same definitions as given above.].

The reaction between a compound (72) and a compound (7) can be conducted under the same conditions as employed in the reaction between the compound (2) and the compound (3) shown in the Reaction formula-1.

The reaction for converting a compound (73) to a compound (1r) can be conducted by heating the compound (73) in the presence of an acid or a basic compound. The acid can be exemplified by inorganic acids such as hydrochloric acid, hydrobromic acid, sulfuric acid, phosphoric acid and the like, and organic acids such as acetic acid and the like. The basic compound can be exemplified by inorganic bases such as sodium hydroxide, potassium hydroxide, sodium carbonate, potassium carbonate, sodium hydrogencarbonate, potassium hydrogencarbonate and the like. The reaction is conducted generally at about 50°–150° C., preferably at about 70°–120° C., and is complete generally in about 0.5–24 hours.

[Reaction formula-24]

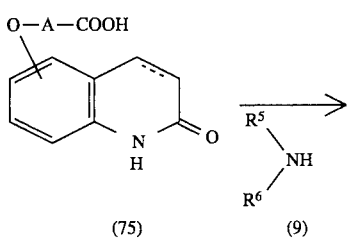

(75)        (9)

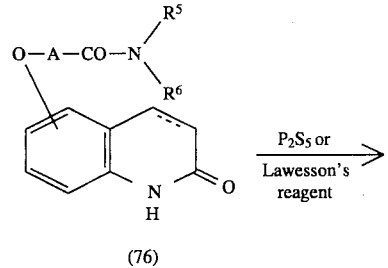

(76)

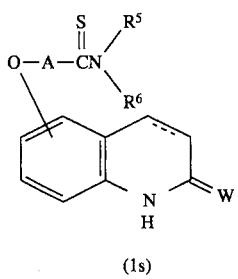

(1s)

[wherein A, $R^5$, $R^6$, W and the carbon-to-carbon bond between the 3- and 4-positions of the carbostyril skeleton have the same definitions as given above.].

The reaction between a compound (75) and a compound (9) can be conducted under the same conditions as employed in the reaction between the compound (10) and the compound (12) shown in the Reaction formula-16.

The reaction between a compound (76) and phosphorus pentasulfide or a Lawesson's reagent can be conducted under the same conditions as employed in the reaction between the compound (1n) and phosphorus pentasulfide or a Lawesson's reagent, shown in the Reaction formula-12. In the reaction, there can be obtained a compound wherein only the carbonyl group of side chain amide group has been subjected to thiocarbonylation, or a compound wherein both the carbonyl group of side chain amide group and the carbonyl group of 2-position of carbostyril skeleton have been subjected to thiocarbonylation.

When the compound (1s) is a compound (1) wherein $R^7$ and $R^8$ or $R^{10}$ and $R^{11}$ form a five- or six-membered saturated heterocyclic ring together with the nitrogen atom to which they bond and further with or without a nitrogen, oxygen or sulfur atom which may be present between $R^7$ and $R^8$ or $R^{10}$ and $R^{11}$ and said heterocyclic ring has a lower alkoxy-lower alkoxy group as a substituent, a compound (1) wherein $R^9$ is a five- or six-membered saturated or unsaturated heterocyclic ring residue having 1–3 nitrogen atoms and said heterocyclic ring residue has a lower alkoxy-lower alkoxy group, a compound (1) wherein $R^1$ and $R^3$ form a pyrrolidinyl group together with the nitrogen atom to which they bond and said pyrrolidinyl group has a lower alkoxy-lower alkoxy group as a substituent, a compound (1) wherein $R^1$ or $R^3$ is a pyrrolidinyl-lower alkyl group which has, as substituent(s) on the pyrrolidine ring, at least one lower alkoxy-lower alkoxy group, or a compound (1) wherein $R^5$ or $R^6$ is a piperidinyl-lower alkyl group which has, as substituent(s) on the piperidinyl ring, at least one lower alkoxy-lower alkoxy group, these compounds (1) can be converted by hydrolysis, to a compound (1) wherein $R^7$ and $R^8$ or $R^{10}$ and $R^{11}$ form the above heterocyclic ring group having a hydroxyl group as a substituent, a compound (1) wherein $R^9$ is the above heterocyclic ring group having a substituent, a compound (1) wherein $R^1$ or $R^3$ is a pyrrolidinyl-lower alkyl group having at least one hydroxyl group as substituent(s) on the pyrrolidine ring, and a compound (1) wherein $R^5$ or $R^6$ is a piperidinyl-lower alkyl group having at least one hydroxyl group as substituent(s) on the piperidinyl ring, respectively.

The above hydrolysis can be conducted under the conditions employed in ordinary hydrolysis. The hydrolysis is conducted generally in the presence of a basic compound, a mineral acid, an organic acid or the like in an appropriate solvent. The basic compound includes, for example, sodium hydroxide, potassium hydroxide, barium hydroxide and potassium carbonate; the mineral acid includes, for example, sulfuric acid, hydrochloric acid and nitric acid; and the organic acid includes, for example, acetic acid, aromatic sulfonic acids (e.g. p-toluenesulfonic acid) and Lewis acids (e.g. boron trichloride). The solvent includes, for example, water; alcohols such as methanol, ethanol, isopropanol and the like; ketones such as acetone, methyl ethyl ketone and the like; ethers such as dioxane, tetrahydrofuran, ethylene glycol dimethyl ether and the like; acetic acid; and mixtures thereof. The reaction proceeds generally at about room temperature to 200° C., preferably at about room temperature to 150° C., and is complete generally in about 0.5–30 hours.

A compound (1) wherein $R^1$ or $R^3$ is a lower alkoxycarbonyl group-substituted lower alkyl group, can be converted by hydrolysis to a compound (1) wherein $R^1$ or $R^3$ is a carboxy group-substituted lower alkyl group.

The hydrolysis can be carried out in the presence of an acid or a basic compound in an appropriate solvent or in the absence of any solvent. The solvent includes, for example, water; lower alcohols such as methanol, ethanol, isopropanol and the like; ketones such as acetone, methyl ethyl ketone and the like; ethers such as dioxane, tetrahydrofuran, ethylene glycol dimethyl ether and the like; fatty acids such as acetic acid, formic acid and the like; and mixed solvents thereof. The acid includes, for example, mineral acids such as hydrochloric acid, sulfuric acid, hydrobromic acid and the like, and organic acids such as formic acid, acetic acid, aromatic sulfonic acids and the like. The basic compound includes, for example, metal carbonates such as sodium carbonate, potassium carbonate and the like, and metal hydroxides such as sodium hydroxide, potassium hydroxide, calcium hydroxide and the like. The reaction proceeds favorably generally at about room temperature to 200° C., preferably at about room temperature to 150° C., and is complete generally in about 0.5–25 hours.

A compound (1) wherein $R^1$ is a group

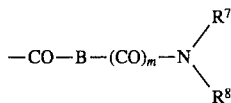

and a compound (1) wherein $R^3$ is a group

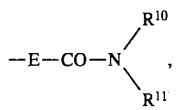

can be converted, by reduction under the same conditions as employed in the reduction of the compound (37) shown in the reaction formula 15, to a compound (1) wherein R is a group

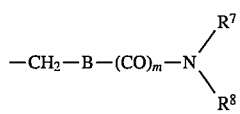

and a compound (1) wherein $R^3$ is a group

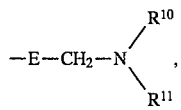

respectively.

A compound (1) wherein wherein $R^7$ and $R^8$ or $R^{10}$ and $R^{11}$ form a five- or six-membered saturated heterocyclic ring together with the nitrogen atom to which they bond and further with or without a nitrogen, oxygen or sulfur atom which may be present between $R^7$ and $R^8$ or $R^{10}$ and $R^{11}$ and said heterocyclic ring has, as a substituent, a lower alkyl group having at least one lower alkoxy-lower alkoxy group, a compound (1) wherein $R^9$ is a five- or six-membered saturated or unsaturated heterocyclic ring residue having 1–3 nitrogen atoms and said heterocyclic ring residue has a lower alkyl group having at least one lower alkoxy-lower alkoxy group, and a compound (1) wherein $R^1$ and $R^2$ form a pyrrolidinyl group together with the nitrogen atom to which they bond and said pyrrolidinyl group has, as a substituent, a lower alkyl group having at least one lower alkoxy-lower alkoxy group, can be converted, by hydrolysis under the same conditions as employed in the hydrolysis of each of the above-mentioned compounds (1) each having a heterocyclic ring having a lower alkoxy-lower alkoxy group as a substituent, to a compound (1) wherein $R^7$ and $R^8$ or $R^{10}$ and $R^{11}$ form a five- or six-membered saturated heterocyclic ring together with the nitrogen atom to which they bond and further with or without a nitrogen, oxygen or sulfur atom which may be present between $R^7$ and $R^8$ or $R^{10}$ and $R^{11}$ and said heterocyclic ring has, as a substituent, a lower alkyl group having at least one hydroxyl group, a compound (1) wherein $R^9$ is a five- or six-membered saturated or unsaturated heterocyclic ring residue having 1–3 nitrogen atoms and said heterocyclic ring residue has a lower alkyl group having at least one hydroxyl group, and a compound (1) wherein $R^1$ and $R^2$ form a pyrrolidinyl group together with the nitrogen atom to which they bond and said pyrrolidinyl group has, as a substituent, a lower alkyl group having at least one hydroxyl group, respectively.

A compound (1) wherein $R^3$, $R^7$ or $R^8$ is a hydroxyl group-substituted lower alkyl group, can be converted, by protecting the hydroxyl group with, for example, a tetrahydropyranyloxy group or a lower alkylenedioxy group (e.g. a 1,1-dimethylmethylenedioxy group), subjecting the protected compound to the reactions shown in the reaction formulas 2–22 and deprotecting the protected group, to a desired compound (1) wherein $R^3$, $R^7$ or $R^8$ is a hydroxyl group-substituted lower alkyl group. The deprotection is conducted by hydrolysis under the same conditions as employed in the hydrolysis of each of the above-mentioned compounds (1) each having a heterocyclic ring having a lower alkoxy-lower alkoxy group as a substituent.

A compound (1) wherein $R^7$ or $R^8$ is a hydrogen atom, can be converted, by protecting the site to which the hydrogen atom bonds, with a lower alkoxycarbonyl group (e.g. a tert-butoxycarbonyl group), subjecting the protected compound to the reactions shown in the reaction formulas 2–22 and deprotecting the protected group, to a desired compound (1) wherein $R^7$ or $R^8$ is a hydrogen atom. The deprotection is conducted by hydrolysis under the same conditions as employed in the hydrolysis of the above-mentioned compound wherein $R^1$ or $R^3$ is a lower alkoxycarbonyl-substituted lower alkyl group.

The carbostyril derivative represented by general formula (1) according to the present invention can be easily converted to an acid addition salt by allowing a pharmaceutically acceptable acid to act on the derivative. The acid includes, for example, inorganic acids such as hydrochloric acid, sulfuric acid, phosphoric acid, hydrobromic acid and the like, and organic acids such as oxalic acid, maleic acid, fumaric acid, malic acid, tartaric acid, citric acid, benzoic acid and the like.

The carbostyril derivative represented by general formula (1) according to the present invention, which has an acidic group, can be easily converted to a salt by allowing a pharmaceutically acceptable basic compound to act on the derivative. The basic compound includes, for example, sodium hydroxide, potassium hydroxide, calcium hydroxide, sodium carbonate and potassium hydrogencarbonate.

The products thus obtained in each step can be isolated and purified by ordinary separation means. The separation means can be exemplified by solvent extraction, dilution, recrystallization, column chromatography and preparative thin-layer chromatography.

Needless to say, the compounds of the present invention include optical isomers.

The compound of general formula (1) is generally used in the form of ordinary pharmaceutical preparations. The pharmaceutical preparations are prepared using diluents or excipients ordinarily used, such as filler, bulking agent, binder, humectant, disintegrator, surfactant, lubricant and the like. The pharmaceutical preparations can be used in various forms depending upon the purpose of remedy, and typical forms include tablets, pills, powders, solutions, suspensions, emulsions, granules, capsules, suppositories, injections (solutions, suspensions, etc.), etc. In preparing tablets, various carriers conventionally known in the art can be used. The carriers can be exemplified by excipients such as lactose, white sugar, sodium chloride, grape sugar, urea, starch, calcium carbonate, kaolin, crystalline cellulose, silicic acid and the like; binders such as water, ethanol, propanol, simple syrup, grape sugar solution, starch solution, gelatin solution, carboxymethyl cellulose, shellac, methyl cellulose, potassium phosphate, polyvinylpyrrolidone and the like; disintegrators such as dry starch, sodium alginate, powdered agar, powdered laminaran, sodium hydrogencarbonate, calcium carbonate, polyoxyethylene sorbitan-fatty acid esters, sodium lauryl sulfate, stearic acid monoglyceride, starch, lactose and the like; disintegration inhibitors such as white sugar, stearin, cacao butter, hydrogenated oil and the like; absorption promoters such as quaternary ammonium salts, sodium lauryl sulfate and the like; humectants such as glycerine, starch and the like; adsorbents such as starch, lactose, kaolin, bentonite, colloidal silicic acid and the like; and lubricants such as refined talc, stearic acid salts, boric acid powder, polyethylene glycol and the like. The tablets can be prepared, as necessary, in the form of ordinary coated tablets, such as sugar-coated tablets, enteric coated tablets or film-coated tablets, or in the form of double-layered tablets or multi-layered tablets. In preparing pills, various carriers conventionally known in the art can be used. The carriers can be exemplified by excipients such as glucose, lactose, starch, cacao butter, hardened vegetable oils, kaolin, talc and the like; binders such as powdered acacia, powdered tragacanth, gelatin, ethanol and the like; and disintegrators such as laminaran, agar and the like. In preparing suppositories, various carriers conventionally known in the art can be used. The carriers can be exemplified by a polyethylene glycol, cacao butter, a higher alcohol, a higher alcohol ester, gelatin and a semi-synthetic glyceride. In preparing injections in the form of solution or suspension, they are sterilized and preferably isotonic to blood. In preparing these solutions, pills and suspensions, there can be used all of the diluents conventionally used in the art, such as water, ethyl alcohol, propylene glycol, ethoxylated isostearyl alcohol, polyoxyisostearyl alcohol and polyoxyethylene sorbitan-fatty acid ester. In this case, the injections may contain sodium chloride, glucose or glycerine in an amount sufficient to make the injections isotonic, and may further contain a solubilizing agent, a buffer solution, a soothing agent, etc. all ordinarily used. The pharmaceutical preparations may furthermore contain, as necessary, a coloring agent, a preservative, a perfume, a flavoring agent, a sweetening agent and other drugs.

The amount of the compound of general formula (1) to be contained in the present pharmaceutical preparation is not particularly restricted and can be selected in a wide range, and is generally 1–70% by weight, preferably 1–30% by weight in the pharmaceutical preparation.

The method for administering the present pharmaceutical preparation is not particularly restricted. The pharmaceutical preparation can be administered in various methods depending upon the form of preparation, the age, sex and other conditions of patient, the degree of disease condition of patient, etc. For example, tablets, pills, a solution, a suspension, an emulsion, granules or capsules are administered orally. An injection is intravenously administered singly or in admixture with an ordinary auxiliary solution of grape sugar, amino acid or the like, or, as necessary, is singly administered intramuscularly, intradermally, subcutaneously or intraperitoneally. Suppositories are administered intrarectally.

The dose of the pharmaceutical preparation of the present invention is appropriately selected depending upon the administration method, the age, sex and other conditions of patient, the degree of disease condition of patient, etc., and is generally about 0.1–10 mg per kg of body weight per day in terms of the amount of the active ingredient, i.e. the compound (1) of general formula (1). Preferably, each administration unit form contains the active ingredient in an amount of 1–200 mg.

[EXAMPLES]

Reference Examples, Examples, Pharmacological Test Results and Preparation Examples are shown below.

Reference Example 1

27 g of 1-(2-aminoethyl)-4-methoxymethoxypiperidine was dropwise added to a solution of 15 g of benzaldehyde in 300 ml of ethanol, at room temperature. The mixture was stirred at the same temperature for 1 day. To the reaction mixture was added 5 g of 10% Pd-C, and the resulting mixture was allowed to absorb hydrogen at room temperature at atmospheric pressure. After a reaction was over, the catalyst was removed by filtration. The filtrate was diluted with ethyl acetate. The dilution was subjected to extraction with 10% hydrochloric acid. The aqueous layer was made alkaline with an aqueous potassium hydroxide solution and then subjected to extraction with ethyl acetate. The extract was washed with water and dried with magnesium sulfate. The solvent was removed by distillation. The resulting residue was purified by a silica gel column chromatography (eluant: 10% methanol-chloroform) to obtain 25.50 g of 1-(2-benzylaminoethyl)-4-methoxymethoxypiperidine.

Light yellow oil $^1$H-NMR (CDCl$_3$) δ; 1.35–1.75 (4H, m), 1.75–2.0 (2H, m), 2.0–2.2 (2H, m), 2.47 (2H, t, J=6.1 Hz), 2.69 (2H, t, J=6.1 Hz), 3.37 (3H, s), 3.5–3.7 (1H, m), 3.80 (2H, s), 4.68 (2H, s), 7.2–7.4 (5H, m).

Reference Example 2

1.7 ml of chloroacetyl chloride was dropwise added to a solution of 3.0 g of aniline hydrochloride and 7 ml of triethylamine in 30 ml of dichloromethane. The mixture was stirred at room temperature for 3 hours, then washed with water and a saturated aqueous sodium hydrogencarbonate solution in this order, and dried with magnesium sulfate. The solvent was removed by distillation. The resulting residue was crystallized from ethyl acetate-n-hexane to obtain 2.45 g of N-(2-chloroacetyl)aniline as a light brown solid. A suspension of 2.45 g of the N-(2-chloroacetyl)-aniline, 2.8 g of 4-methoxymethoxypiperidine, 2.45 g of sodium iodide and 2.3 ml of triethylamine dissolved in 30 ml of acetonitrile was refluxed for 1.5 hours. The reaction mixture was diluted with ethyl acetate. The dilution was washed with water and dried with magnesium sulfate. The solvent was removed by distillation. The resulting residue was purified by a silica gel column chromatography (eluant: ethyl acetate: n-hexane= 1:1) to obtain 3.64 g of 1-(anilinocarbonylmethyl)-4-methoxymethoxypiperidine as a light yellow oil.

A solution of 3.64 g of 1-(anilinocarbonylmethyl)-4-methoxymethoxypiperidine in 10 ml of tetrahydrofuran was added to a suspension of 630 mg of lithium aluminum hydride in 50 ml of tetrahydrofuran. The mixture was refluxed for 3 hours. To the reaction mixture were added 1.5 ml of an aqueous solution containing 10% of potassium hydroxide and 1.5 ml of water. The mixture was diluted with ethyl acetate, and the dilution was filtered. The solvent in the filtrate was removed by distillation to obtain 3.41 g of 1-(2-anilinoethyl)-4-methoxymethoxypiperidine.

Brown oil $^1$H-NMR (CDCl$_3$) δ; 1.6–1.7 (2H, m), 1.9 (2H, m), 2.2 (2H, m), 2.60 (2H, t, J=6 Hz), 2.9 (2H, m), 3.14 (2H, t, J=6 Hz), 3.37 (3H, s), 3.6 (1H, m), 4.69 (2H, s), 6.7 (2H, m), 7.18 (2H, dd, J=7.3 Hz, 8.5 Hz).

Reference Example 3

13.4 g of dicyclohexylcarbodiimide was added, at room temperature, to a solution of 19.3 g of 1-benzyloxycarbonyl-4-methoxymethoxy-L-proline, 8.5 ml of cyclohexylmethylamine and 7.5 g of N-hydroxysuccinimide in 200 ml of dioxane. The mixture was stirred at the same temperature for 2 hours, then heated at 60° C. for 1 hour, and allowed to cool, followed by filtration. The solvent in the filtrate was removed by filtration. The resulting residue was purified by a silica gel column chromatography (eluant; 5% methanol/chloroform) to obtain 21.2 g of N-(1-benzyloxycarbonyl-4-methoxymethoxy-L-prolyl)-N-cyclohexylmethylamine as a light yellow oil.

21.2 g of the obtained N-(1-benzyloxycarbonyl-4-methoxymethoxy-L-prolyl)-N-cyclohexylmethylamine was dissolved in 200 ml of ethanol. To the solution was added 2 g of 10% Pd-C. The mixture was subjected to hydrogenation for 3 hours. The catalyst was removed by filtration. The solvent in the filtrate was removed by distillation to obtain 14.9 g of N-(4-methoxymethoxy-L-prolyl)-N-cyclohexylmethylamine.

Light yellow oil $^1$H-NMR (CDCl$_3$) δ; 0.9–1.8 (11H, m), 2.0 (1H, m), 2.5 (1H, m), 2.96 81H, dd, J=3.8 Hz, 12.5 Hz), 3.08 (2H, dd, J=6.5 Hz, 12.5 Hz), 3.24 (1H, d, J=12.5 Hz), 3.37 (3H, s), 4.15 (1H, t, J=8.3 Hz), 4.3 (1H, m), 4.62 (1H, d, J=7 Hz), 4.66 (1H, d, J=7 Hz), 7.94 81H, br).

Reference Example 4

Using 3 g of 1-(2-aminoethyl)-4-methoxymethoxypiperidine and 2 g of cyclooctanone, 4.3 g of 1-(2-cyclooctylaminoethyl)-4-methoxymethoxypiperidine was obtained in the same manner as in Reference Example 1.

Light yellow oil $^1$H-NMR (CDCl$_3$) δ; 1.3–2.0 (18H, m), 2.05–2.2 (2H, m), 2.44 (2H, t, J=6.1 Hz), 2.55–2.85 (5H, m), 3.37(3H, s), 3.5–3.65 (1H, m), 4.68 (2H, s).

Reference Example 5

0.49 ml of 3-chloropropanesulfonyl chloride was dropwise added, at 0° C., to a solution of 1.19 g of 1-(2-cyclooctylaminoethyl)-4-methoxymethoxypiperidine and 0.67 ml of triethylamine in 10 ml of dichloromethane. The mixture was stirred at room temperature for 1 day. The reaction mixture was washed with water and dried with magnesium sulfate. The solvent was removed by distillation. The resulting residue was purified by silica gel column chromatography (eluant: 2% methanol/dichloromethane) to obtain 1.2 g of 1-{2-[N-(3-chloropropylsulfonyl)-N-cyclooctylamino]-ethyl}- 4-methoxymethoxypiperidine.

Light yellow oil $^1$H-NMR (CDCl$_3$) δ; 1.35–2.05 (18H, m), 2.15–2.35 (4H, m), 2.57 (2H, t), 2.7–2.9 (2H, m), 3.16 (2H, t, J=7.6 Hz), 3.27 (2H, t, J=7.0 Hz), 3.37(3H, s), 3.55–3.7 (1H, m), 3.69 (2H, t, J=6 Hz), 3.75–3.9 (1H, m), 4.68 (2H, s).

Reference Example 6

A solution of 53.3 g of 6-(4-chlorobutoxy)carbostyril and 32 g of sodium sulfite dissolved in 500 ml of water and 200 ml of ethanol was refluxed for 1 day. The solution was allowed to cool and stand for 3 days and then filtered. The filtrate was made acidic with diluted hydrochloric acid. The solvent was removed by distillation. To the resulting residue was added water, and the precipitate was collected by filtration to obtain 47.5 g of 6-(4-hydroxysulfonylbutoxy)carbostyril as a white powder.

Reference Example 7

300 g of phosphorus oxychloride was added to 47.5 g of 6-(4-hydroxysulfonylbutoxy)carbostyril. The mixture was refluxed for 5 hours. The phosphorus oxychloride was removed by distillation under reduced pressure. The resulting residue was diluted with chloroform. Thereto was added ice, and the organic layer was separated and dried with magnesium sulfate. The solvent was removed by distillation. The residue was crystallized from n-hexane to obtain 48.17 g of 4-(2-chloro-6-quinolyloxy)butylsulfonyl chloride.

White powder

Reference Example 8

1.75 g of 4-(2-chloro-6-quinolyloxy)butylsulfonyl chloride was added, at 0° C., to a solution of 1.6 g of 1-[2-(2-chlorobenzylamino)ethyl]-4-methoxymethoxypiperidine and 1 ml of triethylamine in 25 ml dichloromethane. The mixture was stirred at room temperature for 1 day. The reaction mixture was washed with water and dried with magnesium sulfate. The solvent was removed by distillation. The resulting residue was purified by a silica gel column chromatography (eluant: 3% methanol/dichloromethane) to obtain 2.63 g of 2-chloro-6-[4-{N-(2-chlorobenzyl)-N-[2-(4-methoxymethoxy-1-piperidinyl)ethyl]aminosulfonyl}butoxy]quinoline.

Light yellow oil $^1$H-NMR (CDCl3) δ; 7.80–8.05 (2H, m), 7.58 (1H, d, J=7.4 Hz), 7.15–7.45 (5H, m), 7.07 (1H, d, J=2.6 Hz), 4.65 (2H, s), 4.60 (2H, s), 4.12 (2H, t, J=5.8 Hz), 3.45–3.60 (1H, m), 3.10–3.45 (7H, m), 2.60–2.80 (2H, m), 2.44 (2H, t, J=6.2 Hz), 1.92–2.22 (6H, m), 1.75–1.92 (2H, m), 1.45–1.75 (2H, m).

Reference Example 9

A suspension of 30 g of 6-(4-chlorobutoxy)carbostyril, 103 ml of benzylamine and 33 g of sodium iodide in 300 ml of dimethylformamide was stirred at 80° C. for 8 hours. The reaction mixture was allowed to cool and then poured into water. The resulting precipitate was collected by filtration. The precipitate was washed with water and diethyl ether in this order to obtain 29.1 g of 6-(4-benzylaminobutoxy)carbostyril.

Light yellow powder

Reference Example 10

1.28 g of 6-(3-aminopropoxy)carbostyril hydrochloride was added, at 0° C., to 10 ml of an aqueous solution containing 0.3 g of carbon disulfide and 0.4 g of sodium hydroxide. The mixture was stirred at 80° C. for about 2 hours. Thereto was added 0.55 g of ethyl chlorocarbonate at 35° C. The resulting mixture was stirred for 30 minutes. The reaction mixture was poured into water, followed by extraction with ethyl acetate. The filtrate was dried with magnesium sulfate. The solvent was removed by distillation. To the resulting residue was added diethyl ether, and the resulting crystals were collected by filtration and purified by a silica gel column chromatography (eluant: 3.3% methanol/dichloromethane) to obtain 0.22 g of 6-(3-isothiocyanatopropoxy)carbostyril.

Reference Example 11

A solution of 3.13 g of 1-[2-(cyclooctylmethylamino)ethyl]-4-methoxymethoxypiperidine and 1.0 ml of 3-chloropropaneisocyanate in 20 ml of dichloromethane was stirred at room temperature for 3 hours. The solvent was removed by distillation under reduced pressure to obtain 4.2 g of N-cyclooctylmethyl-N-[2-(4-methoxymethoxy-1-piperidinyl)ethyl]-N'-(3-chloropropyl)urea.

$^1$H-NMR (CDCl3) δ; 1.15–1.8 (15H, m), 1.85–2.2 (6H, m), 2.25–2.4 (2H, m), 2.51 (2H, t, J=5 Hz), 2.75–2.85 (2H, m), 3.10 (2H, d, J=7.5 Hz), 3.25–3.3 (4H, m), 3.37 (3H, s), 3.55–3.7 (3H, m), 4.68 (2H, s).

Using appropriate starting materials, the compounds shown in the following Tables 1–14 were obtained in the same manner as in Reference Examples 1, 2 and 5.

TABLE 1

Reference Example 12

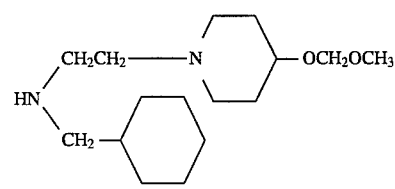

$^1$H-NMR(CDCL$_3$) δ;
0.8–2.0(15H, m), 2.13(2H, m), 2.44(4H, m), 2.66(2H, t, J=6Hz), 2.75(2H, m), 3.37(3H, s), 3.57(1H, m), 4.68(2H, s)

Reference Example 13

TABLE 1-continued

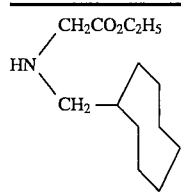

$^1$H-NMR (CDCl$_3$) δ;
1.28(3H, t, J=7.2Hz), 1.4–1.9(15H, m), 2.42(2H, d, J=6.5Hz), 3.39(2H, s), 4.19(2H, q, J=7.2Hz)

Reference Example 14

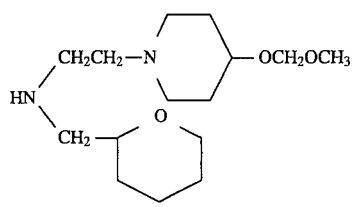

$^1$H-NMR (CDCl$_3$) δ;
1.2–2.0(12H, m), 2.1(2H, m), 2.47(2H, t, J=6.2Hz), 2.6–2.8(2H, m), 2.70(2H, t, J=6.2Hz), 3.37(3H, s), 3.42(2H, m), 3.57(1H, m), 3.96(1H, m), 4.68(2H, s)

TABLE 2

Reference Example 15

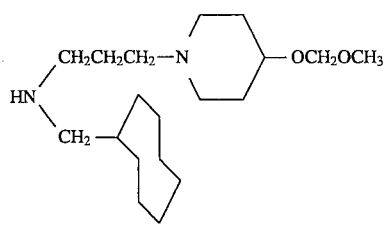

$^1$H-NMR(CDCL$_3$) δ;
1.2–2.0(21H, m), 2.1(2H, m), 2.3–2.7(6H, m), 2.8(2H, m), 3.38(3H, s), 3.6(1H, m), 4.70(2H, s)

Reference Example 16

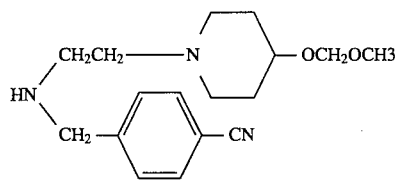

$^1$H-NMR (CDCl$_3$) δ;
1.6(2H, m), 1.9(2H, m), 2.1(2H, m), 2.48(2H, t, J=6Hz), 2.67(2H, t, J=6Hz), 2.7(2H, m), 3.37(3H, s), 3.6(1H, m), 3.86(2H, s), 4.68(2H, s), 7.43(2H, d, J=8Hz), 7.61(2H, d, J=8Hz)

Reference Example 17

TABLE 2-continued

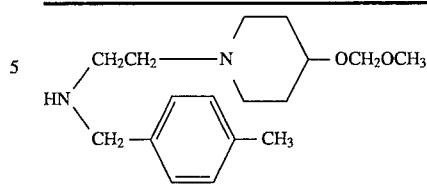

$^1$H-NMR (CDCl$_3$) δ;
1.6(2H, m), 1.8(2H, m), 2.1(2H, m), 2.33(3H, s), 2.47(2H, t, J=6Hz), 2.68(2H, t, J=6Hz), 2.7(2H, m), 3.37(3H, s), 3.6(1H, m), 3.76(2H, s), 4.68(2H, s), 7.12(2H, d, J=8Hz), 7.20(2H, d, J=8Hz)

TABLE 3

Reference Example 18

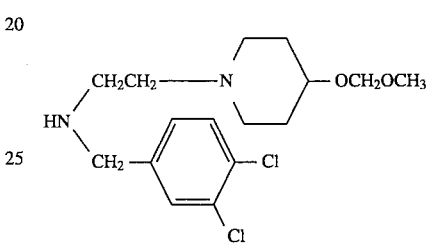

$^1$H-NMR(CDCl$_3$) δ;
1.6(2H, m), 1.9(2H, m), 2.12(2H, m), 2.47(2H, t, J=6Hz), 2.65(2H, t, J=6Hz), 2.7(2H, m), 3.37(3H, s), 3.6(1H, m), 3.76(2H, s), 4.68(2H, s), 7.15(1H, dd, J=2Hz, 8Hz), 7.38(1H, d, J=8Hz), 7.43(1H, d, J=2Hz)

Reference Example 19

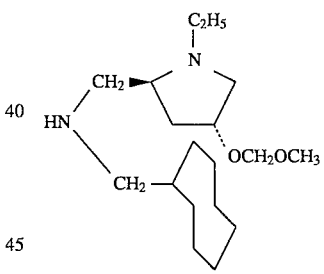

$^1$H-NMR (CDCl$_3$) δ;
1.07(3H, t, J=7.2Hz), 1.2–1.7(17H, m), 1.9(2H, m), 2.3(2H, m), 2.40(2H, d, J=6.8Hz), 2.53(1H, dd, J=6.5Hz, 11.5Hz), 2.7–2.9(3H, m), 3.36(3H, s), 3.43(1H, dd, J=6.2Hz, 9.8Hz), 4.2(1H, m), 4.62(1H, d, J=6.8Hz), 4.65(1H, d, J=6.8Hz)

TABLE 4

Reference Example 20

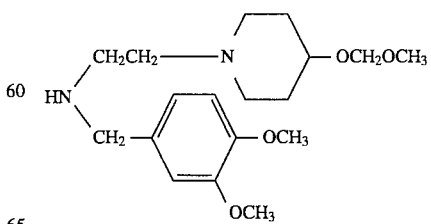

$^1$H-NMR(CDCL$_3$) δ;

TABLE 4-continued 1.6(2H, m), 1.8(2H, m), 2.1(2H, m), 2.45(2H, t, J=6Hz), 2.68(2H, t, J=6Hz), 2.7(2H, m), 3.37(3H, s), 3.5(1H, m), 3.75(2H, s), 3.87(3H, s), 3.89(3H, s), 4.68(2H, s), 6.8(3H, m)

Reference Example 21

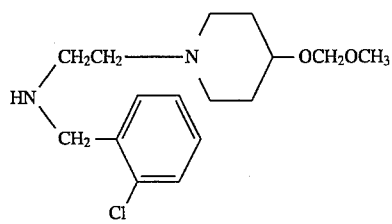

$^1$H-NMR (CDCl$_3$) δ;
1.6(2H, m), 1.8(2H, m), 2.1(2H, m), 2.48(2H, t, J=6Hz), 2.69(2H, t, J=6Hz), 2.7(2H, m), 3.37(3H, s), 3.6(1H, m), 3.89(2H, s), 4.67(1H, s), 7.18–7.24(2H, m), 7.34–7.40(2H, m)

Reference Example 22

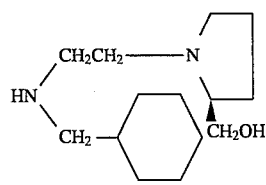

$^1$H-NMR (CDCl$_3$) δ;
0.80–1.00(2H, m), 1.10–1.90(13H, m), 2.30–2.95(8H, m), 3.10–3.20(1H, m), 3.30–3.40(1H, m), 3.50–3.80(1H, m)

TABLE 5

Reference Example 23

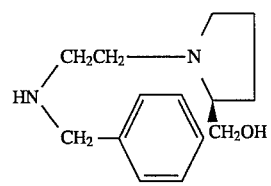

$^1$H-NMR(CDCL$_3$) δ;
1.60–1.95(5H, m), 2.25–3.20(7H, m), 3.35–3.90(4H, m), 7.20–7.40(5H, m)

Reference Example 24

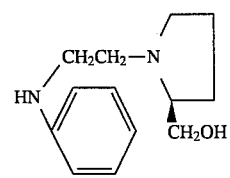

$^1$H-NMR (CDCl$_3$) δ;
1.50–2.00(4H, m), 2.25–2.40(1H, m), 2.55–2.70(2H, m), 3.00–3.65(6H, m), 6.55–6.75(3H, m), 7.10–7.30(2H, m)

Reference Example 25

TABLE 5-continued

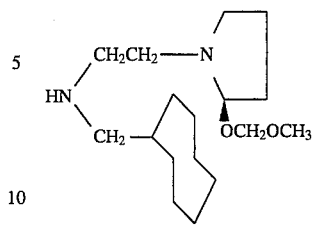

$^1$H-NMR (CDCl$_3$) δ;
1.20–2.00(19H, m), 2.15–2.75(7H, m), 2.90–3.20(2H, m), 3.96(3H, s), 3.40–3.60(2H, m), 4.63(2H, s)

TABLE 6

Reference Example 26

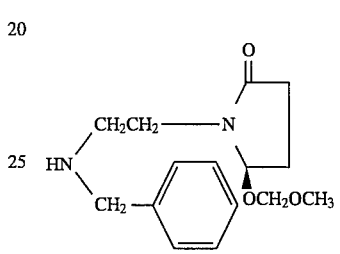

$^1$H-NMR(CDCl$_3$) δ;
1.80–2.65(7H, m), 2.85–3.00(1H, m), 3.25–3.95(9H, m), 4.40–4.70(2H, m), 7.20–7.45(5H, m)

Reference Example 27

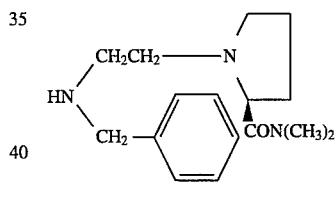

$^1$H-NMR (CDCl$_3$) δ;
1.70–2.15(4H, m), 2.25–2.40(1H, m), 2.60–2.80(4H, m), 2.94(3H, s), 3.04(3H, s), 3.16(1H, brt, J=6.5Hz), 3.36(1H, dd, J=9Hz, 6.5Hz), 3.48(2H, s), 3.75–3.90(2H, m), 7.20–7.40(5H, m)

Reference Example 28

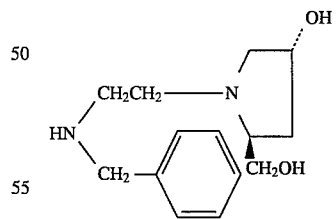

$^1$H-NMR (CDCl$_3$) δ;
1.75–2.00(2H, m), 2.20–2.80(7H, m), 2.85–3.15(2H, m), 3.25–3.50(2H, m), 3.60–3.80(3H, m), 4.35–4.40(1H, m), 7.20–7.40(5H, m)

TABLE 7

Reference Example 29

TABLE 7-continued

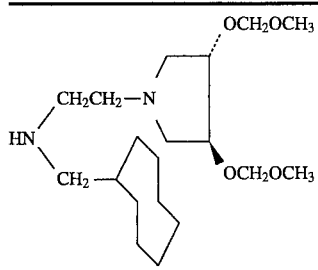

¹H-NMR(CDCL₃) δ;
1.20–1.90(15H, m), 2.30–2.70(7H, m), 2.80–2.95(2H, m), 3.37(6H, s), 3.70–3.85(2H, m), 4.13(2H, brs), 4.65(2H, d, J=6.5Hz), 4.71(2H, d, J=6.5Hz)

Reference Example 30

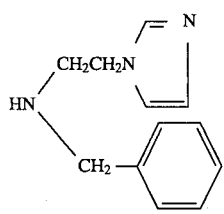

¹H-NMR (CDCl₃) δ;
2.97(2H, t, J=6Hz), 3.77(2H, s), 4.05(2H, t, J=6Hz), 6.95(1H, s), 7.07(1H, s), 7.20–7.45(5H, m), 7.51(1H, s)

Reference Example 31

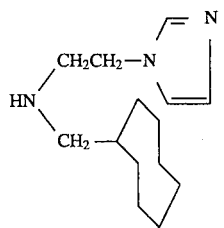

¹H-NMR (CDCl₃) δ;
1.00–1.70(15H, m), 2.34(2H, d, J=6.5Hz), 2.87(2H, t, J=6Hz), 3.98(2H, t, J=6Hz), 6.89(1H, s), 7.00(1H, s), 7.45(1H, s)

TABLE 8

Reference Example 32

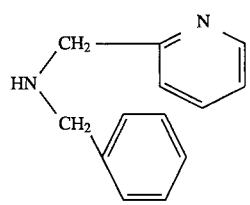

¹H-NMR(CDCL₃) δ;
3.85(2H, s), 3.93(2H, s), 7.10–7.40(7H, m), 7.64(1H, dt, J=7.5Hz, 2Hz), 8.56(2H, brd, J=5Hz)

Reference Example 33

TABLE 8-continued

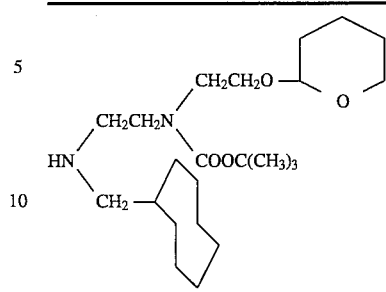

¹H-NMR(CDCl₃) δ;
1.20–1.80(21H, m), 1.46(9H, s), 2.43(2H, d, J=6.5Hz), 2.76(2H, t, J=6.5Hz), 3.30–3.60(6H, m), 3.75–3.90(2H, m), 4.59(1H, brs)

Reference Example 34

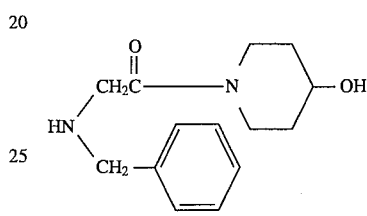

¹H-NMR (CDCl₃) δ;
1.44(2H, brs), 1.76(6H, brs), 3.00–3.20(2H, m), 3.35(2H, s), 3.45–3.60(1H, m), 3.75(2H, s), 3.80–3.95(1H, m), 3.95–4.10(1H, m), 7.15–7.35(5H, m)

TABLE 9

Reference Example 35

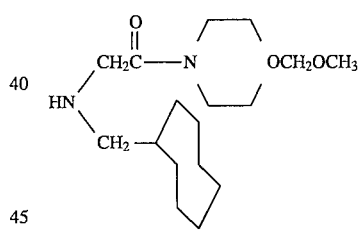

¹H-NMR(CDCL₃) δ;
1.15–1.80(15H, m), 1.80–2.00(2H, m), 2.10(2H, brs), 2.43(2H, d, J=6.5Hz), 3.20–3.35(2H, m), 3.38(3H, s), 3.43(2H, s), 3.60–3.70(1H, m), 3.75–3.90(1H, m), 3.90–4.05(1H, m), 4.70(2H, s)

Reference Example 36

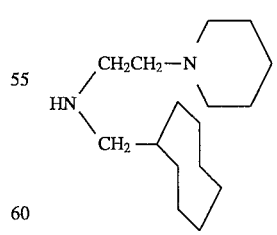

¹H-NMR (CDCl₃) δ;
1.20–1.80(21H, m), 2.30–2.45(9H, m), 2.68(2H, t, J=6Hz)

Reference Example 37

TABLE 9-continued

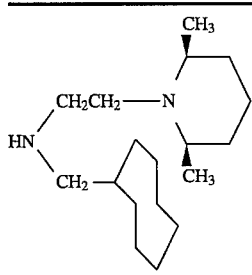

¹H-NMR (CDCl₃) δ;
1.14(6H, d, J=6.5Hz), 1.20–1.80(21H, m), 2.40–2.55(4H, m),
2.60–2.80(4H, m)

TABLE 10

Reference Example 38

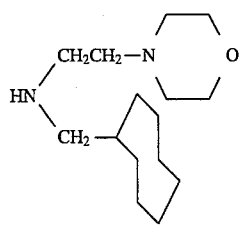

¹H-NMR(CDCL₃) δ;
1.20–1.70(14H, m), 2.40–2.85(12H, m), 3.70(4H, t, J=6Hz)

Reference Example 39

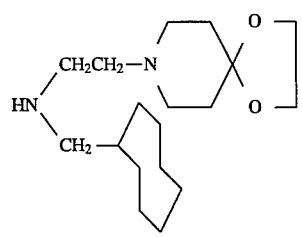

¹H-NMR (CDCl₃) δ;
1.20–1.80(19H, m), 2.40–2.60(9H, m), 2.68(2H, t, J=6Hz),
3.95(4H, s)

Reference Example 40

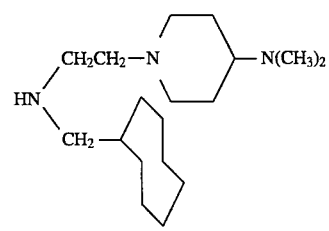

¹H-NMR (CDCl₃) δ;
1.20–2.20(22H, m), 2.27(6H, s), 2.35–2.50(4H, m),
2.67(2H, t, J=6Hz), 2.93(2H, brd, J=12Hz)

TABLE 11

Reference Example 41

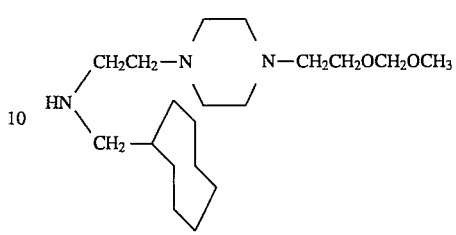

¹H-NMR(CDCL₃) δ;
1.20–1.80(15H, m), 2.35–2.70(16H, m), 3.36(3H, s),
3.66(2H, t, J=6Hz), 4.64(2H, s)

Reference Example 42

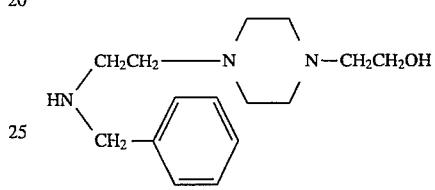

¹H-NMR (CDCl₃) δ;
1.50–2.00(5H, m), 2.40–2.65(11H, m), 2.70(2H, t, J=6Hz),
3.60(2H, t, J=6Hz), 7.20–7.40(5H, m)

Reference Example 43

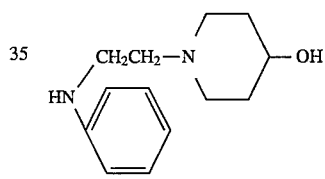

¹H-NMR (CDCl₃) δ;
1.40–2.00(10H, m), 2.17(2H, brt, J=9Hz), 2.62(2H, t, J=6Hz),
2.70–2.90(2H, m), 3.15(2H, t, J=6Hz), 3.65–3.80(2H, m),
4.30(1H, brs), 6.60–6.75(3H, m), 7.15–7.30(2H, m)

TABLE 12

Reference Example 44

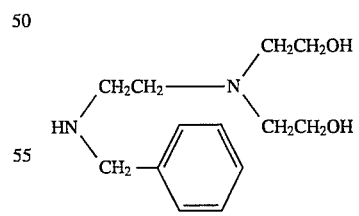

¹H-NMR(CDCl₃ + D₂O) δ;
2.60–2.80(8H, m), 3.58(4H, t, J=5Hz), 3.77(2H, s),
7.20–7.50(5H, m)

Reference Example 45

TABLE 12-continued

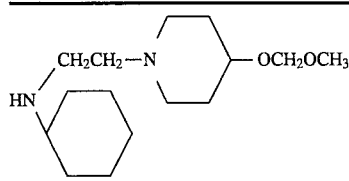

¹H-NMR (CDCl₃) δ;
1.0–2.0(14H, m), 2.05–2.2(2H, m), 2.3–2.5(3H, m), 2.6–2.8(4H, m),
3.70(3H, s), 3.5–3.65(1H, m), 4.68(2H, s)

Reference Example 46

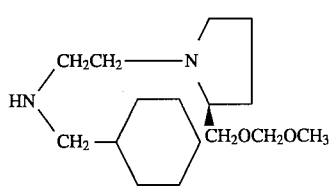

¹H-NMR (CDCl₃) δ;
0.8–2.0(15H, m), 2.25(1H, dd), 2.4–2.55(2H, m), 2.55–2.95(4H, m),
3.0–3.15(2H, m), 3.37(3H, s), 3.40–3.55(2H, m), 4.64(2H, s)

TABLE 13

Reference Example 47

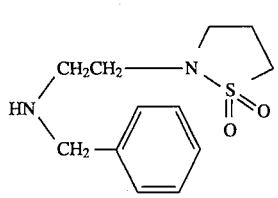

¹H-NMR(CDCl₃) δ;
2.25–2.4(2H, m), 2.84(2H, t, J=6.3Hz), 3.10–3.30(6H, m),
3.82(2H, s), 7.20–7.45(5H, m)

Reference Example 48

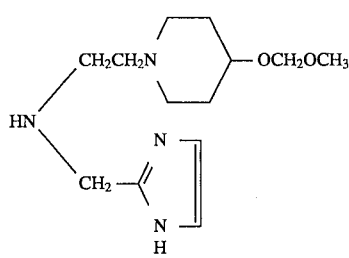

¹H-NMR (CDCl₃) δ;
1.6–1.75(2H, m), 1.9–2.05(2H, m), 2.15–2.35(2H, m),
2.49(2H, t, J=9.3Hz), 2.7–2.8(4H, m), 3.37(3H, s),
3.6–3.75(1H, m), 3.96(2H, s), 4.68(2H, s), 6.97(2H, s)

Reference Example 49

TABLE 13-continued

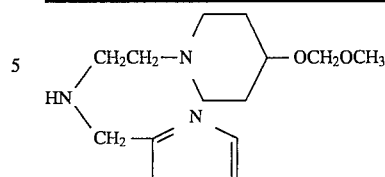

¹H-NMR (CDCl₃) δ;
1.5–1.75(2H, m), 1.8–2.0(2H, m), 2.05–2.2(2H, m),
2.4–2.85(6H, m), 3.37(3H, s), 3.5–3.65(1H, m), 3.93(2H, s),
4.68(2H, s), 7.15(1H, dt, J=5Hz, 2Hz), 7.25(1H, dd),
7.64(1H, dt, J=5Hz, 2Hz), 8.55(1H, dd)

TABLE 14

Reference Example 50

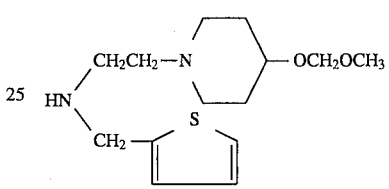

¹H-NMR(CDCl₃) δ;
1.55–1.7(2H, m), 1.8–1.95(2H, m), 2.05–2.15(2H, m),
2.47(2H, t, J=6Hz), 2.65–2.8(4H, m), 3.36(3H, s),
3.5–3.65(1H, m), 4.0(2H, s), 4.67(2H, s), 6.85–7.0(2H, m),
7.2(1H, dd, J=1.5Hz, 5Hz)

Using appropriate starting materials, a compound shown in the following Table 15 were obtained in the same manner as in Reference Example 3.

TABLE 15

Reference Example 51

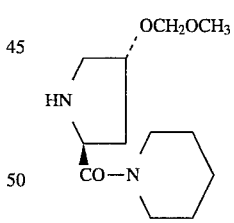

¹H-NMR (CDCl₃) δ;
1.5–1.7(6H, m), 1.87(1H, m), 2.16(1H, ddd, J=1.9Hz,
7.5Hz, 13.2Hz), 2.93(1H, dd, J=3.5Hz, 11.9Hz), 3.39(3H, s),
3.3–3.5(3H, m), 3.6(2H, m), 4.09(1H, t, J=8Hz), 4.3(1H, m),
4.65(2H, s)

Using appropriate starting materials, the compounds shown in the following Tables 16–22 were obtained in the same manner as in Reference Example 5.

TABLE 16

Reference Example 52

TABLE 16-continued

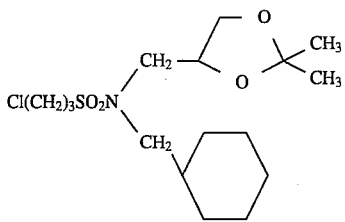

¹H-NMR (CDCl₃) δ;
0.85–1.05(2H, m), 1.1–1.3(3H, m), 1.35(3H, s), 1.45(3H, s),
1.65–1.85(6H, m), 2.25–2.35(2H, m), 3.05–3.4(6H, m),
3.6–3.75(3H, m), 4.05–4.15(1H, m), 4.25–4.4(1H, m)

Reference Example 53

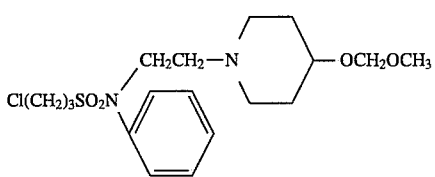

¹H-NMR (CDCl₃) δ;
1.55–1.75(2H, m), 1.8–1.95(2H, m), 2.15–2.25(2H, m), 2.31(2H, dd),
2.45(2H, d, J=6.7Hz), 2.65–2.85(2H, m), 3.28(2H, t, J=7.75Hz),
3.36(3H, s), 3.5–3.65(1H, m), 3.66(2H, t, J=6.3Hz),
3.81(2H, t, J=6.7Hz), 4.66(2H, s), 7.3–7.5(5H, m)

TABLE 17

Reference Example 54

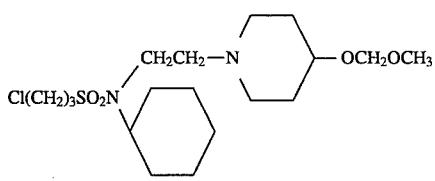

¹H-NMR (CDCl₃) δ;
1.0–2.0(14H, m), 2.15–2.35(4H, m), 2.52(2H, t, J=7.1Hz),
2.25–2.37(2H, m), 3.19(2H, t, J=7.6Hz), 3.30(2H, t, J=7.7Hz),
3.37(3H, s), 3.45–3.65(2H, m), 3.48(2H, t, J=6.5Hz), 4.68(2H, s)

Reference Example 55

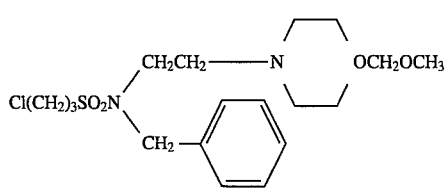

¹H-NMR (CDCl₃) δ;
1.45–1.7(2H, m), 1.82–1.95(2H, m), 2.05–2.2(2H, m),
2.30–2.35(2H, m), 2.41(2H, t, J=6.5z), 2.67–2.8(2H, m),
3.25–3.37(4H, m), 3.37(3H, s), 3.5–3.65(1H, m),
3.69(2H, t, J=6.2Hz), 4.46(2H, s), 4.67(2H, s), 7.30–7.42(5H, m)

TABLE 18

Reference Example 56

TABLE 18-continued

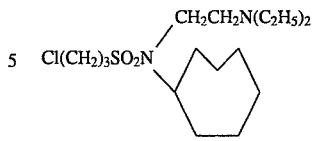

¹H-NMR(CDCl₃) δ;
1.04(6H, t, J=7.2Hz), 1.37–2.10(12H, m), 2.23–2.35(2H, m), 2.5–2.72(6H, m), 3.1–3.3(4H, m),
3.6–3.75(3H, m)

Reference Example 57

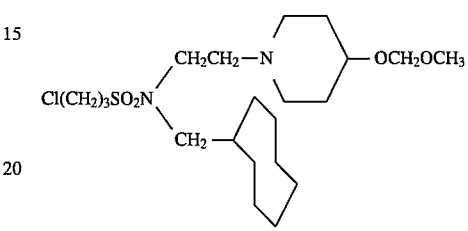

¹H-NMR(CDCl₃) δ;
1.2–2.1(19H, m), 2.3–2.45(2H, m), 3.16(2H, d, J=7.6Hz), 3.25–3.45(7H, m), 3.55–3.65(1H, m),
3.7(2H, t), 3.8–4.0(2H, m), 4.16(2H, s),
4.70(2H, s)

Reference Example 58

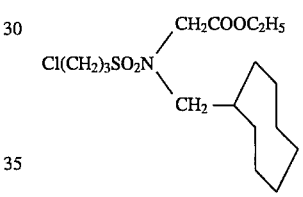

¹H-NMR(CDCl₃) δ;
1.18–1.87(18H, m), 2.27–2.42(2H, m), 3.10(2H, d, J=7.6Hz), 3.29(2H, t, J=7.6Hz), 3.68(2H, t,
J=6.3Hz), 4.09(2H, s), 4.22(2H, q, J=7.1Hz)

TABLE 19

Reference Example 59

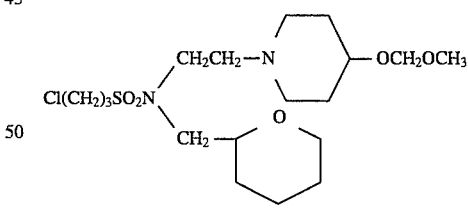

¹H-NMR(CDCl₃) δ;
1.15–1.7(8H, m), 1.8–1.95(2H, m), 2.15–2.35(4H, m),
2.5–2.65(2H, m), 2.75–2.85(2H, m), 3.2–3.6(12H, m),
3.67(2H, t, J=6.3Hz), 3.9–4.05(1H, m), 4.68(2H, s)

Reference Example 60

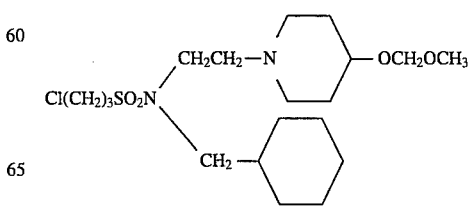

TABLE 19-continued

¹H-NMR(CDCl₃) δ;
0.85–2.0(15H, m), 2.15–2.4(4H, m), 2.51(2H, t, J=6.7Hz), 2.73–2.87(2H, m), 3.0(2H, d, J=7.4Hz), 3.24(2H, t, J=7.7Hz), 3.3–3.45(5H, m), 3.55–3.65(1H, m), 3.68(2H, t, J=6.2Hz), 4.68(2H, s)

TABLE 20

Reference Example 61

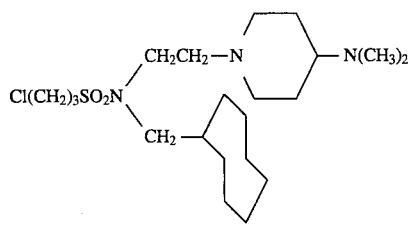

¹H-NMR(CDCl₃) δ;
1.15–1.9(31H, m), 1.95–2.1(2H, m), 2.25–2.35(8H, m), 2.51(2H, t, J=6.8Hz), 2.9–3.05(3H, m), 3.22(2H, t, J=7.6Hz), 3.34(2H, t, J=6.7Hz), 3.69(2H, t, J=6.2Hz)

Reference Example 62

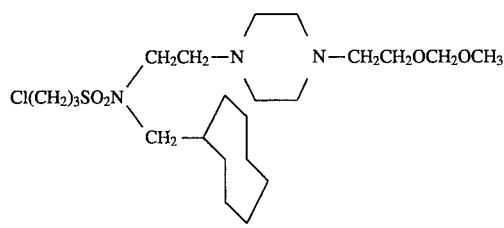

¹H-NMR(CDCl₃) δ;
1.18–1.95(15H, m), 2.2–2.37(2H, m), 2.4–2.7(12H, m), 3.01(2H, d, J=7.8Hz), 3.25(2H, t, J=7.6Hz), 3.3–3.45(5H, m), 3.6–3.75(4H, m), 4.64(2H, s)

TABLE 21

Reference Example 63

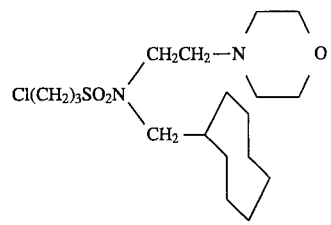

¹H-NMR(CDCl₃) δ;
1.15–1.9(15H, m), 2.2–2.4(2H, m), 2.4–2.6(6H, m), 3.02(2H, d, J=7.6Hz), 3.26(2H, t, J=7.7Hz), 3.36(2H, t, J=6.6Hz), 3.6–3.8(6H, m)

Reference Example 64

TABLE 21-continued

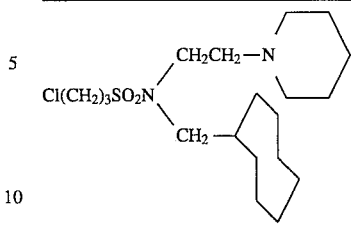

¹H-NMR(CDCl₃) δ;
1.15–2.15(21H, m), 2.20–2.65(8H, m), 3.01(2H, d, J=7.6Hz), 3.26(2H, t, J=7.6Hz), 3.35(2H, t, J=6.7Hz), 3.68(2H, t, J=6.2Hz)

Reference Example 65

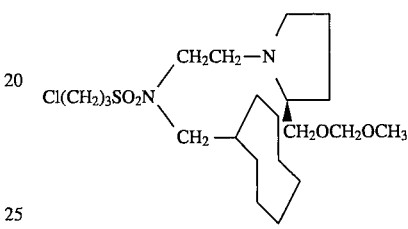

¹H-NMR(CDCl₃) δ;
1.15–2.0(19H, m), 2.1–2.5(4H, m), 2.6–2.75(1H, m), 2.9–3.57(13H, m), 3.68(2H, t, J=3.8Hz), 4.63(2H, s)

TABLE 22

Reference Example 66

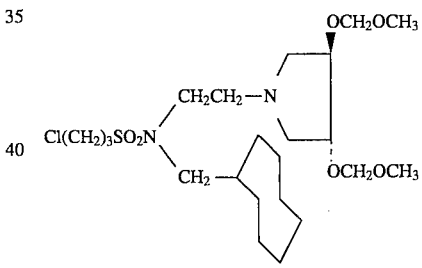

¹H-NMR(CDCl₃) δ;
1.15–1.8(15H, m), 2.2–2.35(2H, m), 2.5–2.8(4H, m), 2.85–3.05(4H, m), 3.25–3.4(10H, m), 3.68(2H, t, J=6.3Hz), 4.12(2H, t, J=4.2Hz), 4.6–4.75(4H, m)

Reference Example 67

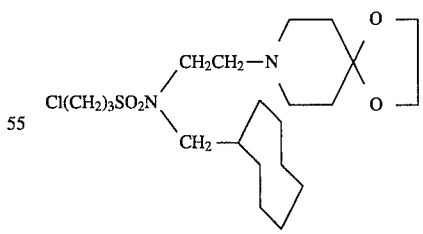

¹H-NMR(CDCl₃) δ;
1.15–1.85(19H, m), 2.25–2.35(2H, m), 2.5–2.65(6H, m), 3.02(2H, d, J=7.6Hz), 3.24(2H, t, J=7.6Hz), 3.35(2H, t, J=6.6Hz), 3.68(2H, t, J=6.2Hz), 3.95(4H, s)

Example 1

A suspension of 800 mg of 6-(4-bromobutoxy)carbostyril, 700 mg of 1-(2-benzylaminoethyl)-4-methoxymethoxypiperidine and 330 mg of sodium hydrogencarbonate in 20 ml of dimethylformamide was stirred at 100° C. for 6 hours. The reaction mixture was allowed to cool and mixed with water. The resulting mixture was subjected to decantation to obtain an oily substance. The substance was dissolved in chloroform, and the solution was washed with water and dried with magnesium sulfate. The solvent was removed by distillation to obtain 1.07 g of 6-[4-{N-[2-(4-methoxymethoxy-1-piperidinyl)ethyl]-N-dibenzylamino}butoxy]carbostyril.

$^1$H-NMR (CDCl3) δ; 1.5–1.9 (8H, m), 2.12 (2H, m), 2.5 (4H, m), 2.6 (2H, m), 2.7 (2H, m), 3.36 (3H, s), 3.6 (1H, m), 3.60 (2H, s), 3.95 (2H, t, J=6 Hz), 4.67 (2H, s), 6.71 (1H, d, J=9.5 Hz), 6.93 (1H, d, J=2.5 Hz), 7.12 (1H, dd, J=2.5 Hz, 9 Hz), 7.2–7.3 (6H, m).

Example 2

10 ml of 10% hydrochloric acid was added to a solution of 1.07 g of 6-[4-{N-[2-(4-methoxymethoxy-1-piperidinyl)ethyl]-N-benzylamino} butoxy]carbostyril in 10 ml of methanol. The mixture was stirred at room temperature for 1 day. The reaction mixture was washed with chloroform and then made alkaline with a 10% aqueous potassium hydroxide solution, followed by extraction with chloroform. The extract was washed with water and dried with magnesium sulfate. The solvent was removed by distillation. The resulting residue was purified by silica gel column chromatography (eluant: 5% methanol/chloroform), followed by recrystallization from ethyl acetate-diethyl ether, to obtain 330 mg of 6-[4-{N-[2-(4-hydroxy- 1-piperidinyl)ethyl]-N-benzylamino}butoxy]carbostyril.

White powder

Melting point: 126°–131° C.

Example 3

5 ml of a 1N aqueous sodium hydroxide solution and 5 ml of methanol were added to 795 mg of 6-[4-(N-ethoxycarbonylmethyl-N-cyclooctyl-methyl)butoxy]carbostyril. The mixture was stirred at 50° C. for 2 hours. The reaction mixture was neutralized with a 10% aqueous hydrochloric acid solution. The resulting precipitate was collected by filtration to obtain 691 mg of 6-[4-(N-carboxymethyl-N-cycloctylmethyl)butoxy]carbostyril.

White powder

Melting point: 154°–155° C.

Example 4

A suspension of 0.44 g of 6-hydroxycabostyril, 0.45 g of potassium carbonate and 1.2 g of 1-{2-[N-(3-chloropropylsulfonyl)-N-cyclooctylamino]ethyl}- 4-methoxymethoxypiperidine in 30 ml of dimethylformamide was stirred at 90° C. for 1 day. The reaction mixture was poured into water, followed by extraction with ethyl acetate. The extract was washed with water and dried with magnesium sulfate. The solvent was removed by distillation. The resulting residue was purified by silica gel column chromatography (eluant: 5% methanol/dichloromethane) to obtain 0.76 g of 6-[3-{N-[2-(4-methoxymethoxy-1-piperidinyl)ethyl-N-cyclooctylaminosulfonyl}propoxy]carbostyril.

Light yellow oil $^1$H-NMR (CDCl$_3$) δ; 7.75 (1H, d, J=9.5 Hz), 7.35 (1H, d, J=9 Hz), 7.15 (1H, dd, J=9 Hz, 2.6 Hz), 7.01 (1H, d, J=2.6 Hz), 6.73 (1H, d, J=9.5 Hz), 4.68 (2H, s), 4.15 (2H, t, J=5.8 Hz), 3.75–3.95 (H, m), 3.58–3.69 (1H, m), 3.37(3H, s), 3.22–3.35 (4H, m), 2.75–2.90 (2H, m), 2.55–2.68 (2H, m), 2.18–2.40 (4H, m), 1.40–2.05 (18H, m).

Example 5

A solution of 2.63 g of 2-chloro-6-[4-{N-(2-chlorobenzyl)-N-[2-(4-methoxymethoxy- 1-piperidinyl)ethyl]aminosulfonyl}butoxy]quinoline dissolved in 50 ml of acetic acid was refluxed for 3.5 hours. The solvent was removed by distillation under reduced pressure to obtain crude 6-[4-{N-(2-chlorobenzyl)-N-[2-(4-methoxymethoxy-1-piperidinyl)ethyl] aminosulfonyl}butoxy]carbostyril. To the substance were added 10 ml of methanol and 10 ml of a 5% aqueous hydrochloric acid solution. The mixture was stirred at room temperature for 1 day and then made alkaline with an aqueous potassium hydroxide solution, followed by extraction with ethyl acetate. The extract was washed with water and dried with magnesium sulfate. The solvent was removed by distillation. The resulting residue was purified by silica gel column chromatography (eluant: 10% methanol/dichloromethane) to obtain 1.4 g of 6-[4-{N-(2-chlorobenzyl)-N-[2-(4-hydroxy- 1-piperidinyl)ethyl]aminosulfonyl}butoxy]carbostyril.

White powder

Melting point: 147°–152° C.

Example 6

6.6 ml of 3-chloropropanesulfonyl chloride was dropwise added, at 0° C., to a dichloromethane solution containing 8 g of 6-(4-benzylaminobutoxy)carbostyril and 7.6 ml of triethylamine. The mixture was stirred at room temperature for 1 day. The reaction mixture was washed with 10% hydrochloric acid and water in this order and dried with magnesium sulfate. The solvent was removed by distillation. The resulting residue was dissolved in 30 ml of dioxane. To the solution was added 10 ml of a 10% potassium hydroxide solution, followed by stirring at room temperature for 30 minutes. The reaction mixture was neutralized with 10% hydrochloric acid, followed by extraction with chloroform. The extract was dried with magnesium sulfate. The solvent was removed by distillation. The resulting residue was crystallized from diethyl ether to obtain 7.3 g of 6-{4-[N-(3-chloropropylsulfonyl)-N-benzylamino]butoxy}carbostyril.

White powder $^1$H-NMR (CDCl$_3$) δ; 1.6–1.7 (4H, m), 2.25–2.35 (2H, m), 3.11 (2H, t, J=7.5 Hz), 3.25–3.35 (2H, m), 3.67 (2H, t, J=6.0 Hz), 3.9–4.0 (2H, m), 4.44 (2H, s), 6.71 (2H, d, J=9.5 Hz), 6.92 (1H, d, J=2.5 Hz), 7.09 (2H, dd, J=2.5 Hz, 9.0 Hz), 7.3–7.4 (6H, m), 7.73 (1H, d, J=9.5 Hz).

Example 7

1.0 g of 6-{4-[N-(3-chloropropylsulfonyl)-N-benzylamino]butoxy}carbostyril and 600 mg of 1,2,4-triazole were stirred at 140° C. for 3 hours. The reaction mixture was diluted with dioxane. The resulting crystals were collected by filtration and purified by a column chromatography (eluant: 3% methanol/chloroform). The purified crystals were recrystallized from ethyl acetate to obtain 327 mg of 6-[4-{N-[3-(1,2,4-triazol-1-yl)propylsulfonyl]-N-benzylamino} butoxy]-carbostyril.

Light yellow powder

Melting point: 137°–139° C.

Example 8

A solution of 6.7 g of 6-(4-chlorobutyl)carbostyril, 5 g of 1-(2-aminoethyl)-4-methoxymethoxypiperidine, 4.0 g of sodium iodide and 2.3 g of sodium hydrogencarbonate in 30 ml of dimethylformamide was stirred at 80° C. for 4 hours. The reaction mixture was diluted with chloroform. The dilution was washed with water and subjected to extraction with 5% hydrochloric acid. The extract was made alkaline with 10% potassium hydroxide, followed by extraction with chloroform. The extract was dried with magnesium sulfate. The solvent was removed by distillation to obtain 9.01 g of 6-{4-[2-(4-methoxymethoxy-1-piperidinyl)ethyl]aminobutoxy}carbostyril.

Light yellow oil $^1$H-NMR (CDCl$_3$) δ; 1.5–1.7 (2H, m), 1.75–1.9 (4H, m), 2.15–2.3 (2H, m), 2.6–2.7 (2H, m), 2.7–2.8 (2H, m), 2.85–2.95 (4H, m), 3.45 (3H, s), 3.5–3.65 (1H, m), 3.95–4.05 (2H, m), 4.65 (2H, s), 6.64 (1H, d, J=9.5 Hz), 6.91 (1H, d, J=2.5 Hz), 7.05 (1H, dd, J=2.5 Hz, 9.0 Hz), 7.39 81H, d, J=9.0 Hz), 7.70 (1H, d, J=9.5 Hz), 8.00 (1H, br).

Example 9

A solution of 2.5 g of 6-{4-[2-(4-methoxymethoxy-1-piperidinyl)ethyl]aminobutoxy}carbostyril, 1.5 g of cyclohexylmethanesulfonyl chloride and 1.35 ml of triethylamine in 30 ml of dichloromethane was stirred at room temperature for 16 hours. The reaction mixture was washed with water and dried with magnesium sulfate. The solvent was removed by distillation. The resulting residue was purified by a silica gel column chromatography (eluant: 3% methanol/chloroform)-to obtain 620 mg of 6-[4-{N-[2-(4-methoxymethoxy-1-piperidinyl)ethyl]-N-cyclohexylmethylsulfonylamino}butoxy]carbostyril.

Light yellow oil $^1$H-NMR (CDCl$_3$) δ; 1.0–2.0 (19H, m), 2.2–2.3 (2H, m), 2.4–2.6 (2H, m), 2.7–2.9 (2H, m), 3.2–3.4 (4H, m), 3.36 (3H, s), 3.5–3.65 (1H, m), 3.95–4.05 (2H, m), 4.67 (2H, s), 6.71 (1H, d, J=9.5), 7.13 (1H, dd, J=2.5H, 9.0 Hz), 7.34 (1H, d, J=9.0 Hz), 7.75 (1H, d, J=9.5 Hz).

Example 10

A solution of 0.22 g of 6-(3-isothiocyanatopropoxy)carbostyril and 0.3 g of 1-[2-(cyclooctylmethylamino)ethyl]-4-methoxymethoxypiperidine in 30 ml of chloroform was stirred at room temperature for 5 hours. The solvent was removed by distillation under reduced pressure. The resulting residue was purified by a silica gel column chromatography (eluant: 3% methanol/dichloromethane) to obtain 0.36 g of 6-[3-{N-2-(4-methoxymethoxy- 1-piperidinyl)ethyl-N-cyclooctylmethylamino}-thiocarbonylaminopropoxy]carbostyril.

Colorless oil

Example 11

A solution of 1.6 g of 6-hydroxycarbostyril, 1.4 g of potasium carbonate and 4.2 g of N-cyclooctylmethyl-N-[2-(4-methoxymethoxy-1-piperidinyl)-ethyl-N-( 3-chloropropyl)urea in 20 ml of dimethylformamide was stirred at 80° C. for 1 day. The reaction mixture was poured into ice water, followed by extraction with ethyl acetate. The extract was washed with water and dried with magnesium sulfate. The solvent was removed by distillation. The resulting residue was purified by a silica gel column chromatography (eluant: 5% methanol/dichloromethane) to obtain 0.76 g of 6-[3-{N-[2-(4-methoxymethoxy-1-piperidinyl)ethyl]-N-cyclooctylmethylamino}carbonylaminopropoxy]carbostyril.

Brown oil $^1$H-NMR (CDCl$_3$) δ; 7.73 (1H, d, J=9.5 Hz), 7.40 (1H, br), 7.29 (1H, d, J=11.4 Hz), 7.15 (1H, dd, J=11.4 Hz, 2.5 Hz), 7.01 (1H, d, 2.5 Hz), 6.70 (1H, d, J=9.5 Hz), 4.65 (2H, s), 4.06 (2H, t, J=6.2 Hz), 3.15–3.65 (8H, m), 3.10 (2H, d, J=7.5 Hz), 2.65–2.90 (2H, m), 2.35–2.60 (2H, m), 2.10–2.35 (2H, m), 1.97–2.10 (2H, t, J=6.5 Hz), 1.10–1.97 (19H, m).

Example 12

A solution of 0.68 g of 6-[3-(N-cyclohexyl-N-methylaminocarbonyl)propoxy]carbostyril and 0.81 g of a Lawesson's reagent in 10 ml of toluene was refluxed for 1.5 hours. The reaction mixture was allowed to cool, followed by solvent removal by distillation. The resulting residue was purified by a silica gel column chromatography (eluant: 2% methanol/dichloromethane) to obtain 0.69 g of 6-[3-(N-cyclohexyl-N-methylaminothiocarbonyl)propoxy]thiocarbostyril.

Yellow powder

Melting point: 170°–172° C.

Example 13

A solution of 13.7 g of 6-[3-(N-cyclohexyl-N-methylaminocarbonyl)propoxy]carbostyril and 4.45 g of phosphorus pentasulfide in 200 ml of benzene was refluxed for 5 hours. The reaction mixture was allowed to cool. The insolubles were removed by filtration. The filtrate was subjected to distillation to remove the solvent. The resulting residue was purified by a silica gel column chromatography (eluant: 5% methanol/dichloromethane) to obtain 7.2 g of 6-[3-(N-cyclohexyl-N-methylaminothiocarbonyl)propoxy]carbostyril.

Yellow powder

Melting point: 167°–170° C.

Using appropriate starting materials, the compounds shown in the following Tables 23–56 were obtained in the same manner as in Example 4.

TABLE 23

Example 14

—O—A—R:

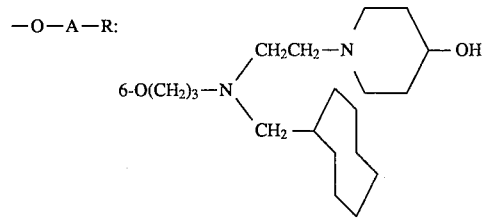

W: oxygen atom
Crystal form: white powder Free form
Melting point: 149–150°
Recrystallization solvent: ethyl acetate - diethyl ether Example 15

—O—A—R:

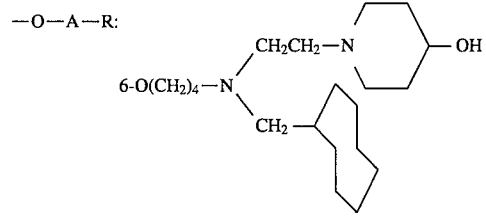

W: oxygen atom
Crystal form: white powder Free form
Melting point: 117–118° C.
Recrystallization solvent: ethyl acetate Example 16

TABLE 23-continued

—O—A—R:

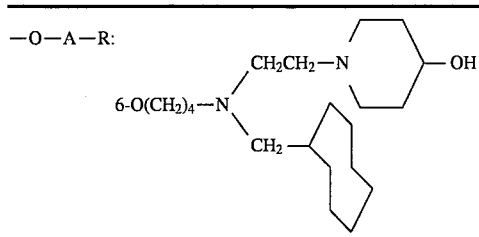

W: oxygen atom
Crystal form: white powder Free form
Melting point: 114.5-116° C.
Recrystallization solvent: ethyl acetate - diethyl ether

TABLE 24

Example 17

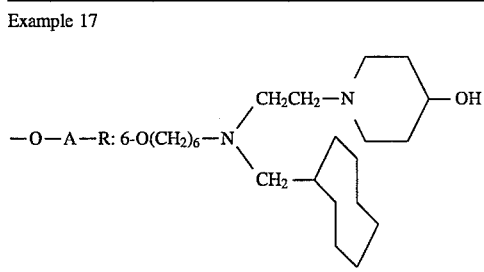

W: oxygen atom
Crystal form: white powder Free form
Melting point: 69-74° C.
Recrystallization solvent: diethyl ether - diisopropyl ether Example 18

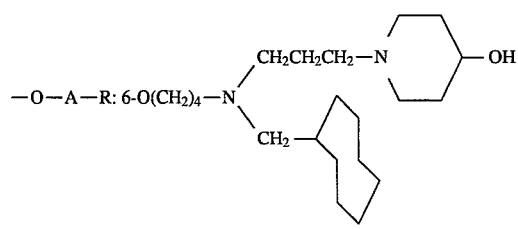

W: oxygen atom
Crystal form: white powder Free form
Melting point: 124-127° C.
Recrystallization solvent: diethyl ether Example 19

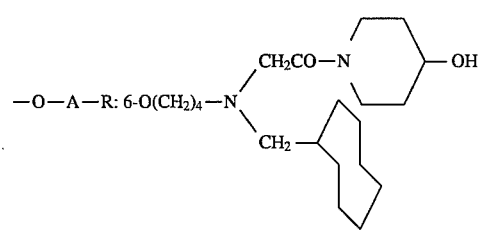

W: oxygen atom
Crystal form: white powder Free form
Melting point: 129.5-131.5° C.
Recrystallization solvent: chloroform - diethyl ether Example 20

TABLE 24-continued

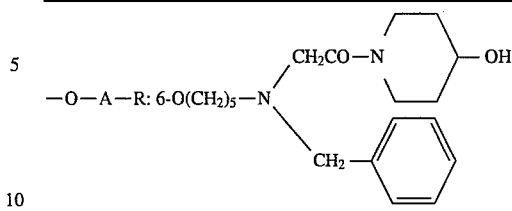

W: oxygen atom
Crystal form: white powder Free form
Melting point: 153.5-162.0° C.
Recrystallization solvent: methanol - diisopropyl ether

TABLE 25

Example 21

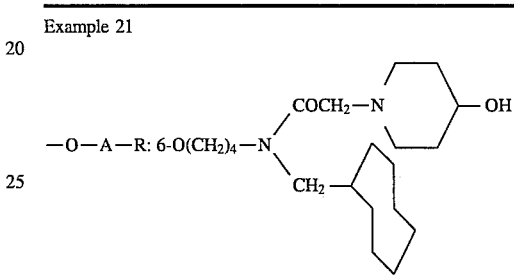

W: oxygen atom
Crystal form: light yellow oil Free form

Example 22

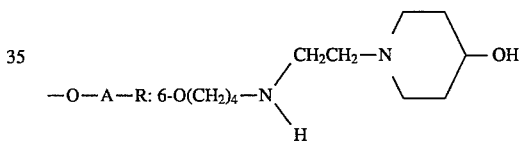

W: oxygen atom
Crystal form: light yellow powder Free form
Melting point: 96–98° C.
Recrystallization solvent: diethyl ether Example 23

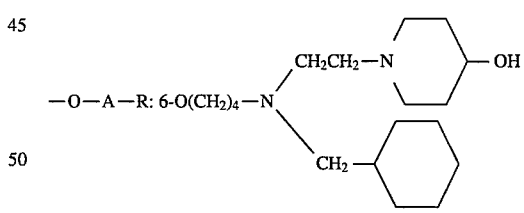

W: oxygen atom
Crystal form: white aciculator Free form
Melting point: 143–145° C.
Recrystallization solvent: ethyl acetate-diethyl ether Example 24

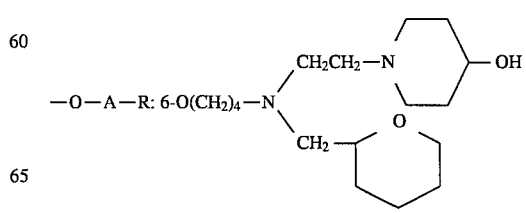

TABLE 25-continued

W: oxygen atom
Crystal form: light yellow powder Free form
Melting point: 105–107° C.
Recrystallization solvent: ethyl acetate-diethyl ether

TABLE 26

Example 25

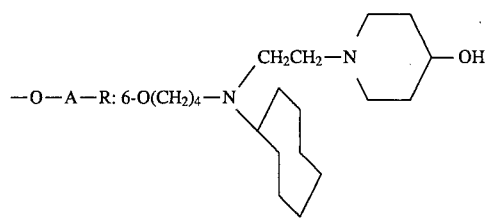

W: oxygen atom
Crystal form: light yellow powder Free form
Melting point: 113–115.5° C.
Recrystallization solvent: diethyl ether Example 26

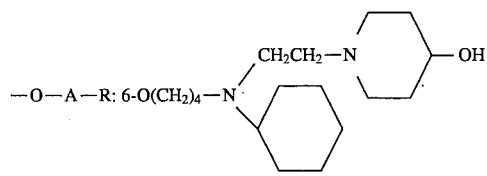

W: oxygen atom
Crystal form: white powder Free form
Melting point: 148–151° C.
Recrystallization solvent: ethyl acetate Example 27

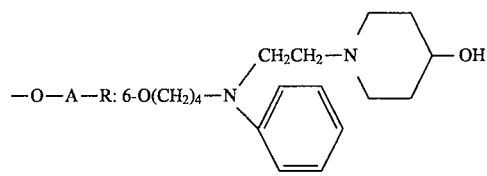

W: oxygen atom
Crystal form: light yellow powder Free form
Melting point: 116–118° C.
Recrystallization solvent: ethyl acetate diethyl ether Example 28

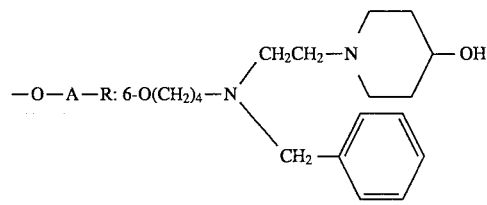

W: oxygen atom
Crystal form: white powder Free form
Melting point: 126–131° C.
Recrystallization solvent: ethyl acetate-diethyl ether

TABLE 27

Example 29

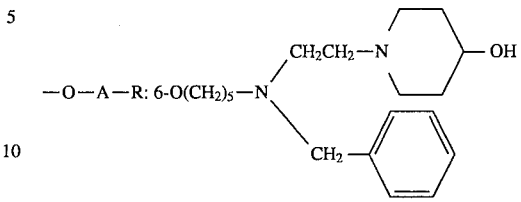

W: oxygen atom
Crystal form: light yellow powder Free form
Melting point: 134–136° C.
Recrystallization solvent: ethyl acetate-methanol Example 30

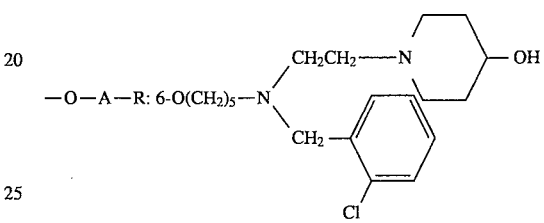

W: oxygen atom
Crystal form: white powder Free form
Melting point: 74° C. (decomposed)
Recrystallization solvent: ethyl acetate-diethyl ether Example 31

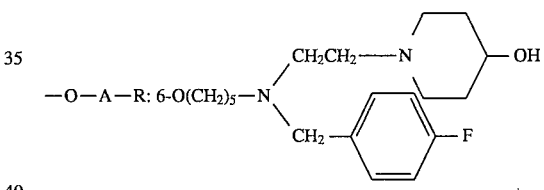

W: oxygen atom
Crystal form: white powder Free form
Melting point: 122–125° C.
Recrystallization solvent: methanol - diisopropyl ether Example 32

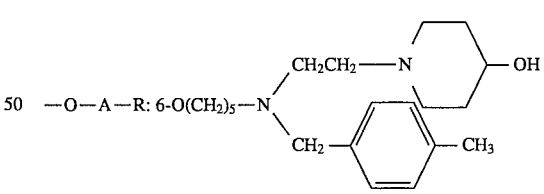

W: oxygen atom
Crystal form: white powder Free form
Melting point: 135–136° C.
Recrystallization solvent: ethyl acetate - diethyl ether

TABLE 28

Example 33

TABLE 28-continued

—O—A—R: 6-O(CH₂)₅—N(CH₂CH₂—N⟨piperidine⟩—OH)(CH₂—C₆H₄—CN)

W: oxygen atom
Crystal form: white powder Free form
Melting point: 131–133° C.
Recrystallization solvent: ethyl acetate - diethyl ether Example 34

—O—A—R: 6-O(CH₂)₅—N(CH₂CH₂—N⟨piperidine⟩—OH)(CH₂—C₆H₄—CO₂H)

W: oxygen atom
Crystal form: white powder Free form
Melting point: 217° C. (decomposed)

Example 35

—O—A—R: 6-O(CH₂)₅—N(CH₂CH₂—N⟨piperidine⟩—OH)(CH₂—C₆H₃(OCH₃)₂)

W: oxygen atom
Crystal form: light yellow amorphous Free form NMR (2)

Example 36

—O—A—R: 6-O(CH₂)₅—N(CH₂CH₂—N⟨piperidine⟩—OH)(CH₂—C₆H₃Cl₂)

W: oxygen atom
Crystal form: white powder Free form
Melting point: 77° C. (decomposed)
Recrystallization solvent: ethyl acetate diethyl ether

TABLE 29

Example 37

—O—A—R: 6-O(CH₂)₅—N(CH₂CH₂—N⟨piperidine⟩—OH)(CH₂—cyclohexyl)

W: oxygen atom
Crystal form: white powder Free form
Melting point: 98.5–101° C.
Recrystallization solvent: methanol - diisopropyl ether Example 38

—O—A—R: 6-O(CH₂)₅—N(CH₂CH₂—N⟨piperidine⟩—OH)(phenyl)

W: oxygen atom
Crystal form: white powder Free form
Melting point: 128–129.5° C.
Recrystallization solvent: methanol - diisopropyl ether Example 39

—O—A—R: 6-O(CH₂)₅—N(CH₂CH₂—N⟨piperidine⟩—OH)(CH₂—pyridyl)

W: oxygen atom
Crystal form: brown oil Free form NMR (3)

Example 40

—O—A—R: 6-O(CH₂)₅—N(CH₂CH₂—N⟨piperidine⟩—OH)(CH₂—thienyl)

W: oxygen atom
Crystal form: light yellow powder Free form NMR (4)

TABLE 30

Example 41

—O—A—R: 6-O(CH₂)₄—N(CH₂CH₂—N⟨piperidine⟩—OH)(CO—cyclohexyl)

W: oxygen atom
Crystal form: white powder Free form
Melting point: 139–147° C.
Recrystallization solvent: methanol - diethyl ether Example 42

TABLE 30-continued

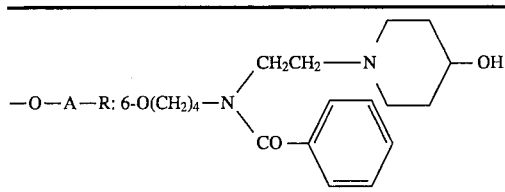

W: oxygen atom
Crystal form: white powder Free form
Melting point: 165–171° C.
Recrystallization solvent: methanol - diethyl ether Example 43

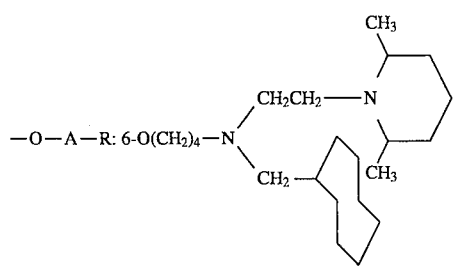

W: oxygen atom
Crystal form: brown caramel-like Free form NMR (5)

Example 44

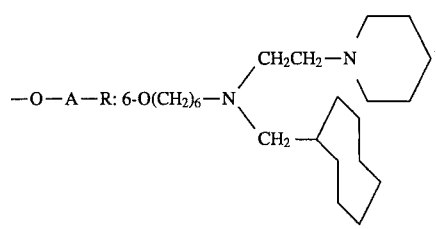

W: oxygen atom
Crystal form: white powder Free form
Melting point: 143–146° C.
Recrystallization solvent: dichloromethane - diisopropyl ether

TABLE 31

Example 45

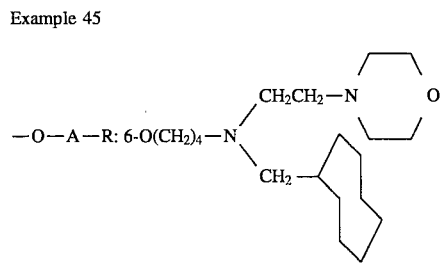

W: oxygen atom
Crystal form: white powder Free form
Melting point: 130–130.5° C.
Recrystallization solvent: dichloromethane - diisopropyl ether Example 46

TABLE 31-continued

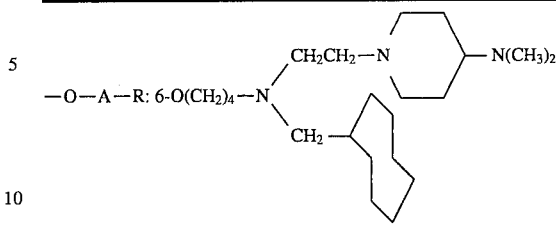

W: oxygen atom
Crystal form: brown caramel-like Free form NMR (6)

Example 47

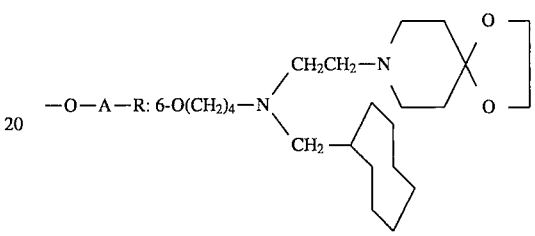

W: oxygen atom
Crystal form: light yellow prisms Free form
Melting point: 108–109° C.
Recrystallization solvent: chloroform - diisopropyl ether Example 48

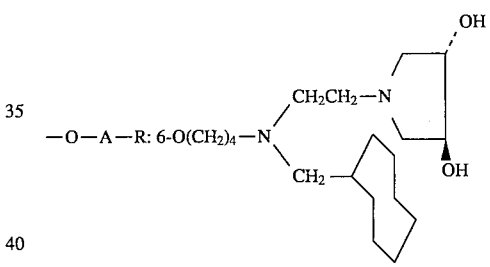

W: oxygen atom
Crystal form: white powder Free form
Melting point: 94.5–97° C.
Recrystallization solvent: isopropanol diisopropyl ether

TABLE 32

Example 49

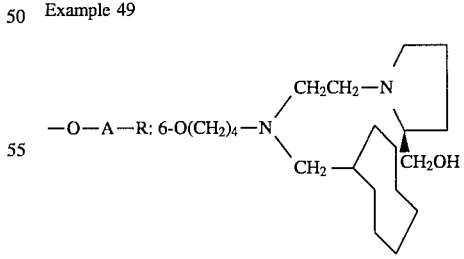

W: oxygen atom
Crystal form: colorless acicular Free form
Melting point: 126–127.5° C. °C.
Recrystallization solvent: dichloromethane - diisopropyl ether Example 50

TABLE 32-continued

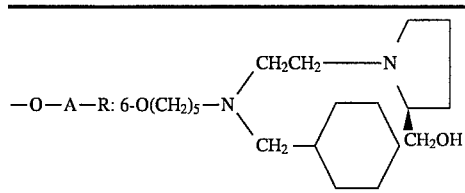

W: oxygen atom
Crystal form: light yellow caramel-like Free form NMR (7)

Example 51

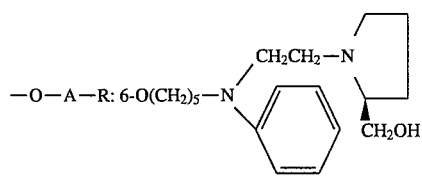

W: oxygen atom
Crystal form: white powder Free form
Melting point: 96.5–98° C.
Recrystallization solvent: methanol - diisopropyl ether Example 52

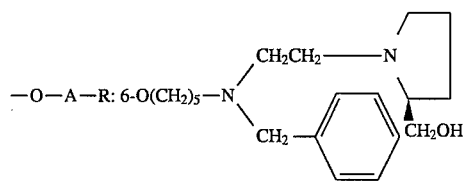

W: oxygen atom
Crystal form: white powder Free form
Melting point: 112–115° C.
Recrystallization solvent: methanol - diisopropyl ether

TABLE 33

Example 53

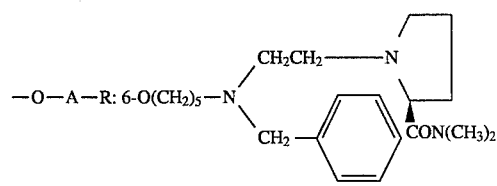

W: oxygen atom
Crystal form: yellow powder Free form NMR (8)

Example 54

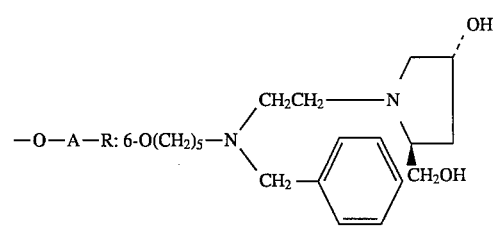

W: oxygen atom

TABLE 33-continued

Crystal form: white powder Free form
Melting point: 106.5–110.5° C.
Recrystallization solvent: isopropanol - diisopropyl ether Example 55

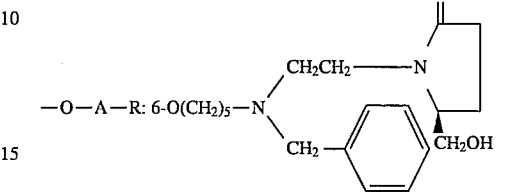

W: oxygen atom
Crystal form: colorless caramel-like Free form

Example 56

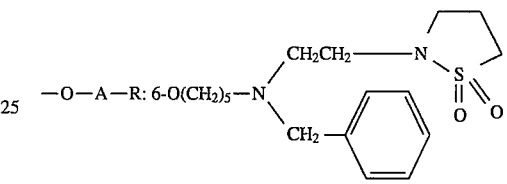

W: oxygen atom
Crystal form: white powder Free form
Melting point: 161–162° C.
Recrystallization solvent: methanol

TABLE 34

Example 57

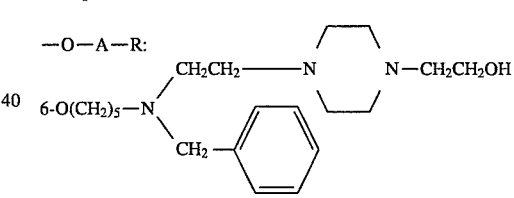

W: oxygen atom
Crystal form: colorless caramel-like Free form NMR (10)

Example 58

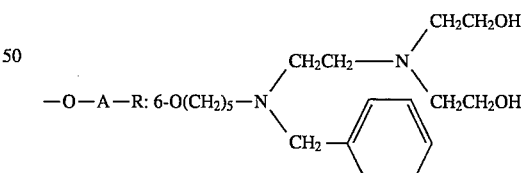

W: oxygen atom
Crystal form: white powder Free form
Melting point: 118–121° C. .5° C.

Example 59

TABLE 34-continued

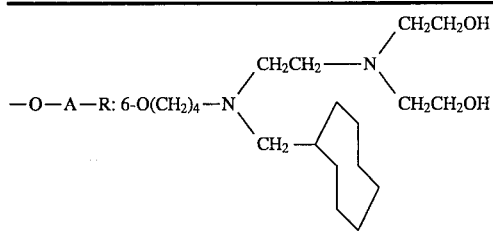
—O—A—R: 6-O(CH₂)₄—

W: oxygen atom
Crystal form: white powder Free form
Melting point: 107.5–108.5°
Recrystallization solvent: ethyl acetate Example 60

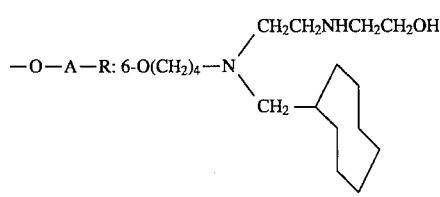
—O—A—R: 6-O(CH₂)₄—

W: oxygen atom
Crystal form: brown caramel-like Free form

TABLE 35

Example 61

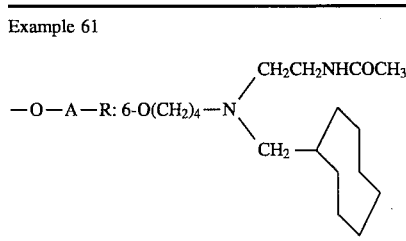
—O—A—R: 6-O(CH₂)₄—

W: oxygen atom
Crystal form: white powder Free form
Melting point: 83–86° C. 31.5° C.
Recrystallization solvent: ethyl acetate - diethyl ether Example 62

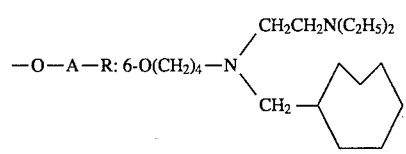
—O—A—R: 6-O(CH₂)₄—

W: oxygen atom
Crystal form: white powder Free form
Melting point: 123–125° C.

Example 63

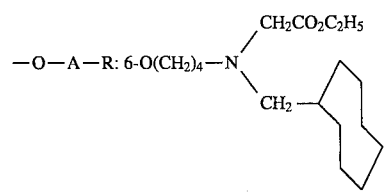
—O—A—R: 6-O(CH₂)₄—

W: oxygen atom
Crystal form: white powder Free form

TABLE 35-continued

Melting point: 98–99° C.
Recrystallization solvent: ethyl acetate

Example 64

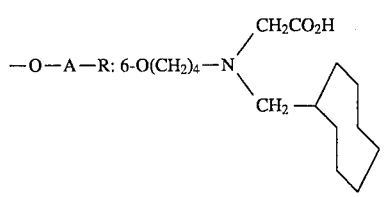
—O—A—R: 6-O(CH₂)₄—

W: oxygen atom
Crystal form: white powder Free form
Melting point: 154–155° C.

TABLE 36

Example 65

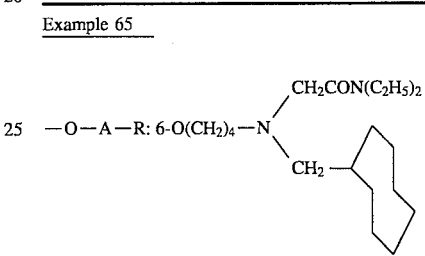
—O—A—R: 6-O(CH₂)₄—

W: oxygen atom
Crystal form: white powder     Free form
Melting point: 116–120° C.
Recrystallization solvent: diethyl ether Example 66

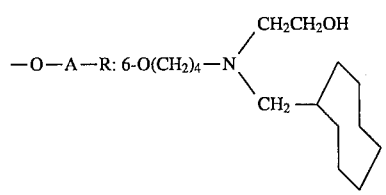
—O—A—R: 6-O(CH₂)₄—

W: oxygen atom
Crystal form: light yellow powder     Free form
Melting point: 95–97° C.
Recrystallization solvent: diethyl ether Example 67

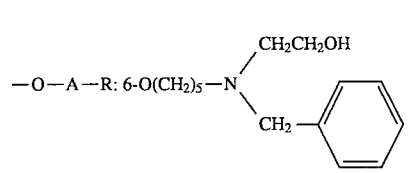
—O—A—R: 6-O(CH₂)₅—

W: oxygen atom
Crystal form: white powder     Free form
Melting point: 168–171° C.
Recrystallization solvent:
methanol - diisopropyl ether Example 68

TABLE 36-continued

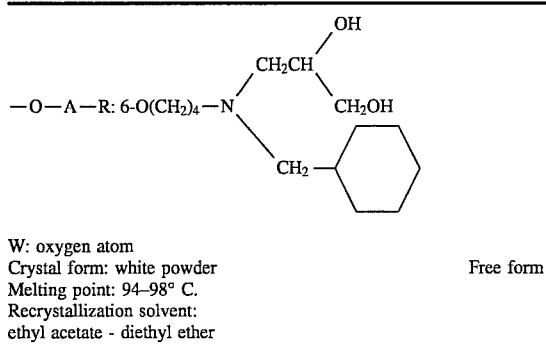

W: oxygen atom
Crystal form: white powder       Free form
Melting point: 94–98° C.
Recrystallization solvent:
ethyl acetate - diethyl ether

TABLE 37

Example 69

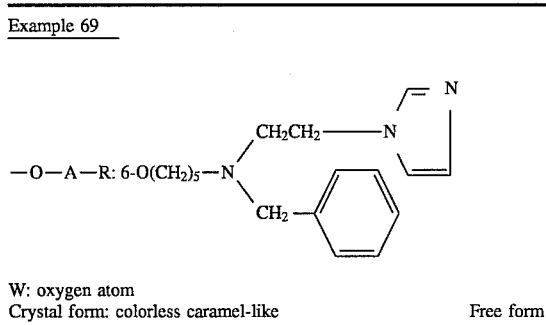

W: oxygen atom
Crystal form: colorless caramel-like       Free form

Example 70

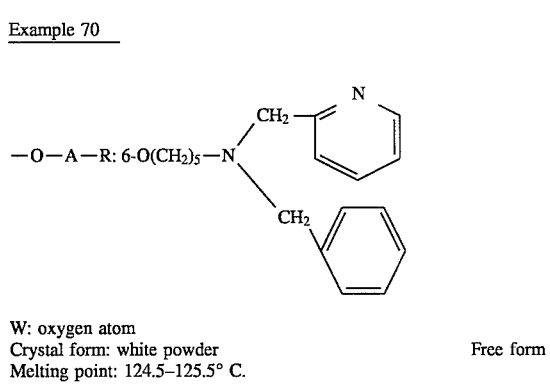

W: oxygen atom
Crystal form: white powder       Free form
Melting point: 124.5–125.5° C.
Recrystallization solvent: ethyl acetate Example 71

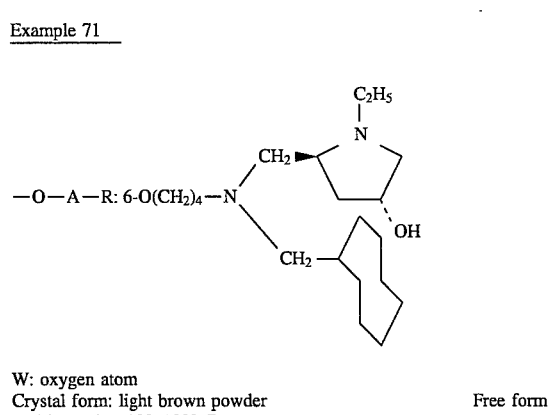

W: oxygen atom
Crystal form: light brown powder       Free form
Melting point: 100–102° C.
Recrystallization solvent: diethyl ether Example 72

TABLE 37-continued

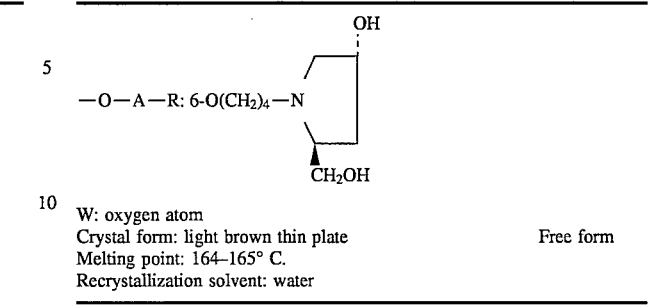

W: oxygen atom
Crystal form: light brown thin plate       Free form
Melting point: 164–165° C.
Recrystallization solvent: water

TABLE 38

Example 73

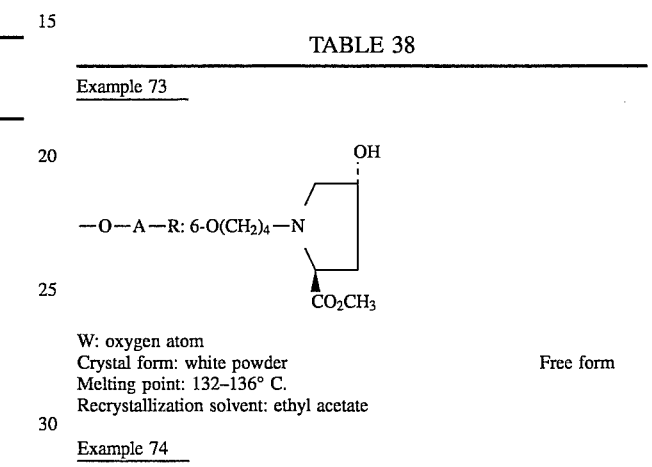

W: oxygen atom
Crystal form: white powder       Free form
Melting point: 132–136° C.
Recrystallization solvent: ethyl acetate Example 74

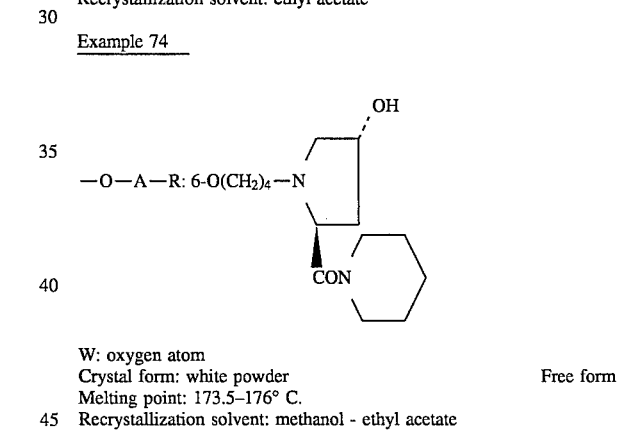

W: oxygen atom
Crystal form: white powder       Free form
Melting point: 173.5–176° C.
Recrystallization solvent: methanol - ethyl acetate Example 75

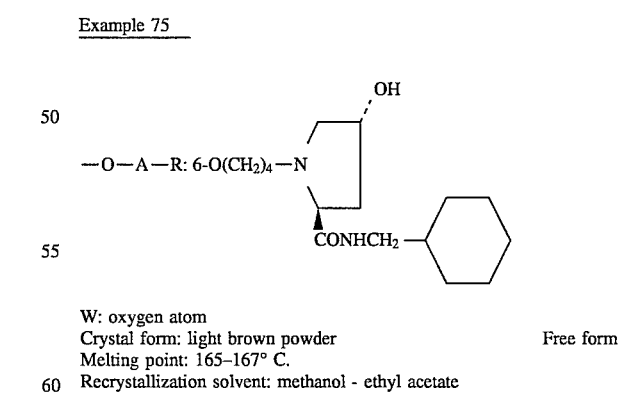

W: oxygen atom
Crystal form: light brown powder       Free form
Melting point: 165–167° C.
Recrystallization solvent: methanol - ethyl acetate Example 76

TABLE 38-continued

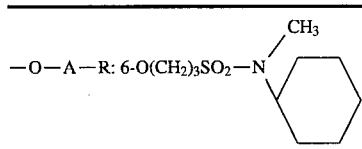

W: oxygen atom
Crystal form: white powder  Free form
Melting point: 157–157.5° C.
Recrystallization solvent: isopropanol

TABLE 39

Example 77

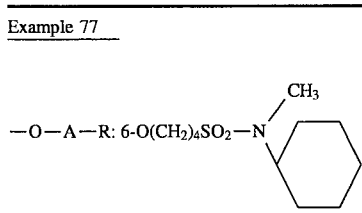

W: oxygen atom
Crystal form: white powder  Free form
Melting point: 179.5° C.
Recrystallization solvent: diethyl ether Example 78

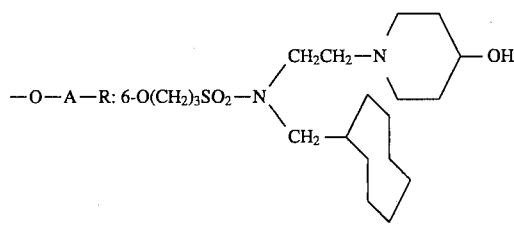

W: oxygen atom
Crystal form: white powder  Free form
Melting point: 181–183° C.
Recrystallization solvent: ethanol Example 79

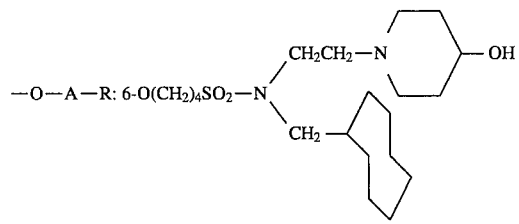

W: oxygen atom
Crystal form: white powder  Free form
Melting point: 171–172° C.
Recrystallization solvent: ethyl acetate-diethyl ether Example 80

TABLE 39-continued

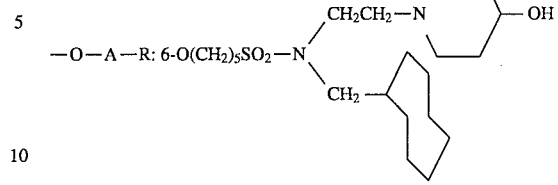

W: oxygen atom
Crystal form: light yellow powder  Free form
Melting point: 145–148° C.
Recrystallization solvent: ethyl acetate

TABLE 40

Example 81

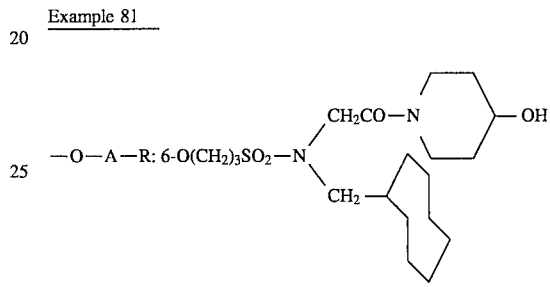

W: oxygen atom
Crystal form: white powder  Free form
Melting point: 163.5–167° C.
Recrystallization solvent: ethyl acetate-diethyl ether Example 82

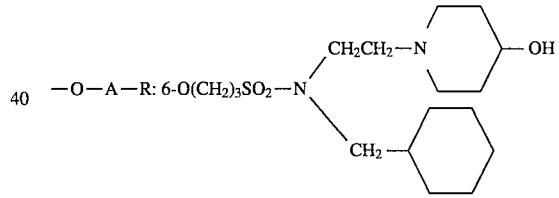

W: oxygen atom
Crystal form: white powder  Free form
Melting point: 200–205° C.

Example 83

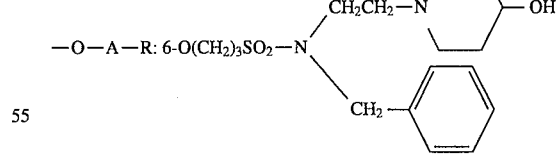

W: oxygen atom
Crystal form: white powder  Free form
Melting point: 189–190.5° C.
Recrystallization solvent: ethanol Example 84

TABLE 40-continued

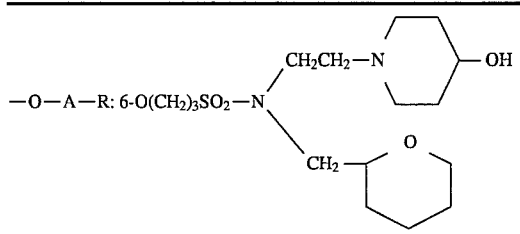

W: oxygen atom
Crystal form: white powder     Free form
Melting point: 172–174.5° C.
Recrystallization solvent: ethyl acetate-diethyl ether

TABLE 41

Example 85

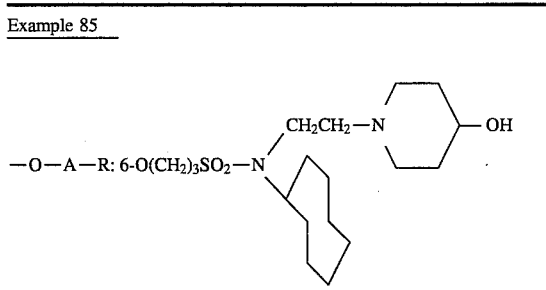

W: oxygen atom
Crystal form: white powder     Free form
Melting point: 182.5–184.5° C.
Recrystallization solvent: methanol - diethyl ether Example 86

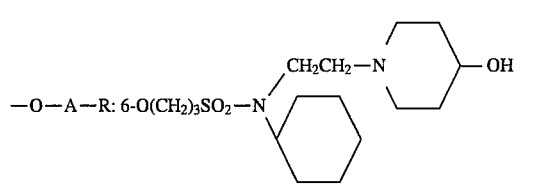

W: oxygen atom
Crystal form: yellow powder     Free form
Melting point: 192–195° C.

Example 87

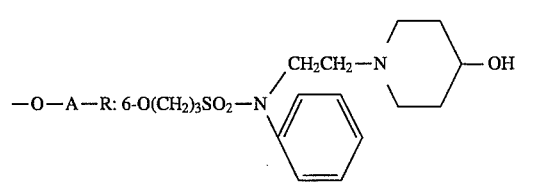

W: sulfur atom
Crystal form: light yellow powder     Free form
Melting point: 164–165.5° C.
Recrystallization solvent: diethyl ether Example 88

TABLE 41-continued

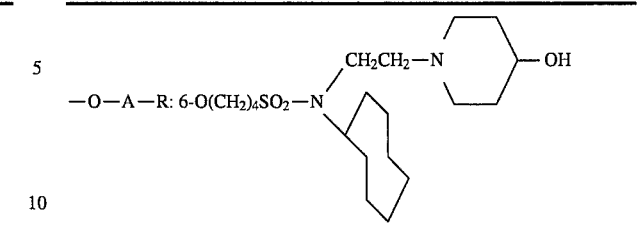

W: oxygen atom
Crystal form: white powder     Free form
Melting point: 161–163° C.

TABLE 42

Example 89

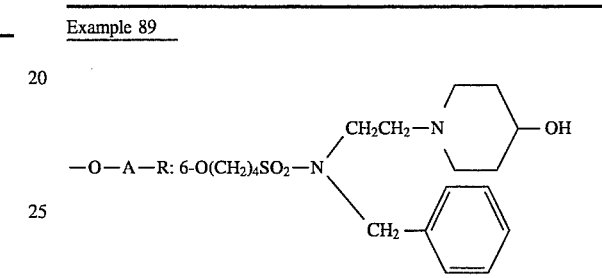

W: oxygen atom
Crystal form: white powder     Free form
Melting point: 165.5–167° C.

Example 90

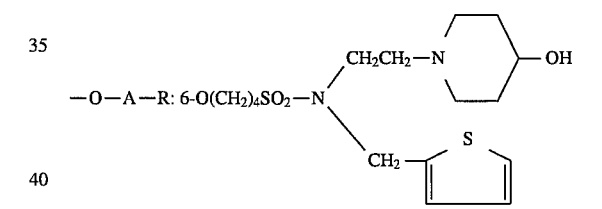

W: oxygen atom
Crystal form: white powder     Free form
Melting point: 129–130.5° C.

Example 91

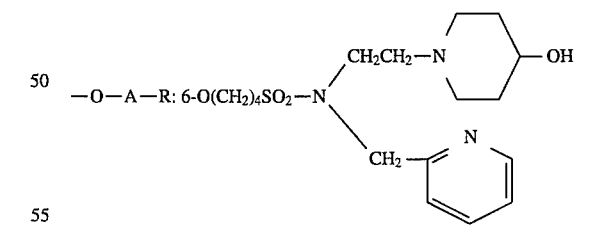

W: oxygen atom
Crystal form: white powder     Free form
Melting point: 98° C.

Example 92

TABLE 42-continued

—O—A—R: 6-O(CH$_2$)$_4$SO$_2$—N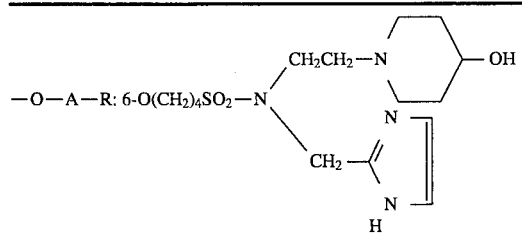

W: oxygen atom
Crystal form: white powder   Free form
Melting point: 180° C. (decomposed)
Recrystallization solvent: ethanol

TABLE 43

Example 93

—O—A—R: 6-O(CH$_2$)$_4$SO$_2$—N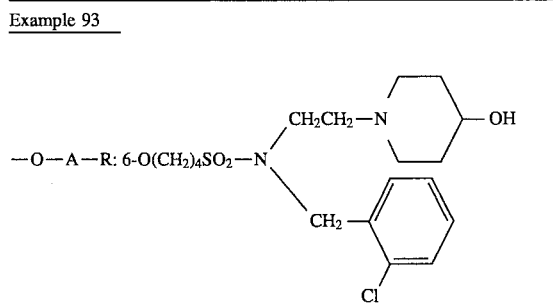

W: oxygen atom
Crystal form: white powder   Free form
Melting point: 147–152° C.

Example 94

—O—A—R: 6-O(CH$_2$)$_4$SO$_2$—N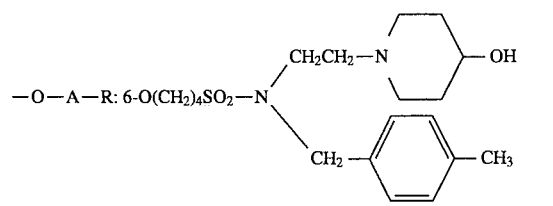

W: oxygen atom
Crystal form: white powder   Free form
Melting point: 164–165° C.

Example 95

—O—A—R: 6-O(CH$_2$)$_4$SO$_2$—N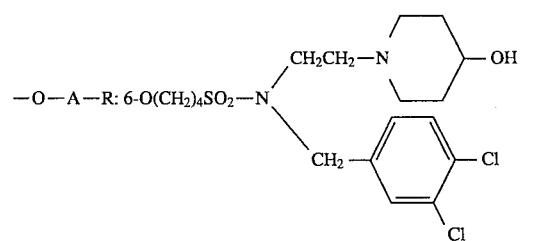

W: oxygen atom
Crystal form: white powder   Free form
Melting point: 169.5–171.5° C.
Recrystallization solvent: methanol Example 96

TABLE 43-continued

—O—A—R: 6-O(CH$_2$)$_4$SO$_2$—N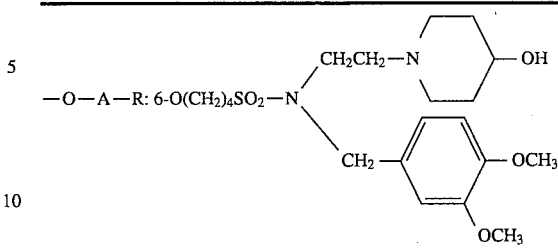

W: oxygen atom
Crystal form: white powder   Free form
Melting point: 140–141.5° C.
Recrystallization solvent: ethyl acetate

TABLE 44

Example 97

—O—A—R: 6-O(CH$_2$)$_3$SO$_2$—N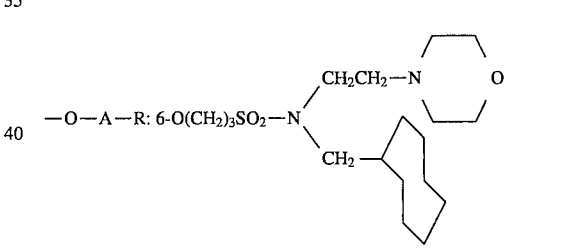

W: oxygen atom
Crystal form: light yellow powder   Free form
Melting point: 154–155° C.
Recrystallization solvent: chloroform - diethyl ether Example 98

—O—A—R: 6-O(CH$_2$)$_3$SO$_2$—N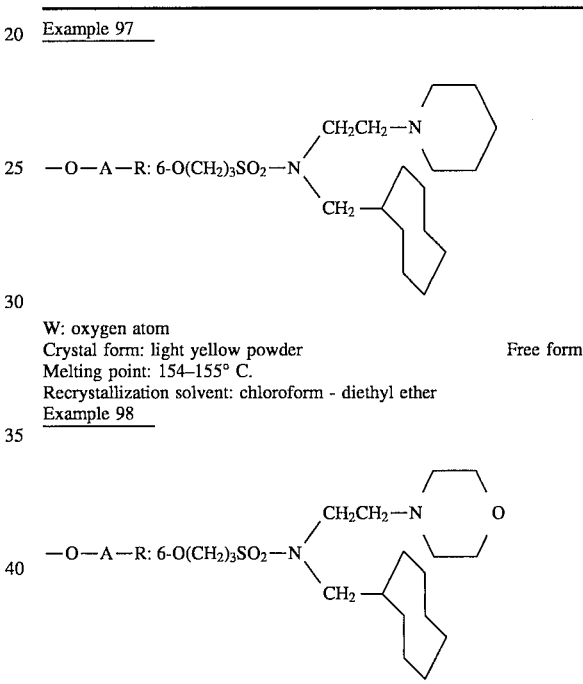

W: oxygen atom
Crystal form: light yellow powder   Free form
Melting point: 168.5–169° C.
Recrystallization solvent: ethanol Example 99

—O—A—R: 6-O(CH$_2$)$_3$SO$_2$—N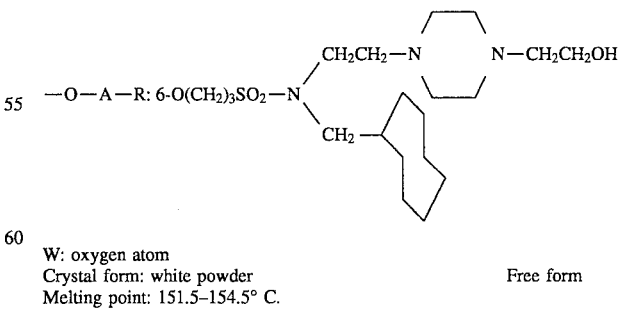

W: oxygen atom
Crystal form: white powder   Free form
Melting point: 151.5–154.5° C.
Recrystallization solvent: diethyl ether Example 100

TABLE 44-continued

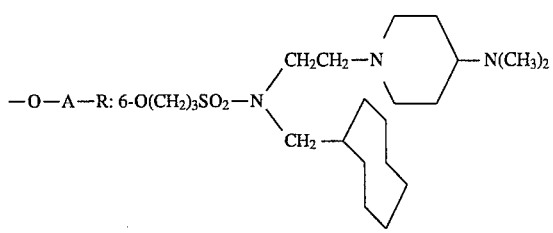

W: oxygen atom
Crystal form: white powder   Free form
Melting point: 129.5–130.5° C.
Recrystallization solvent: ethyl acetate-diethyl ether

TABLE 45

Example 101

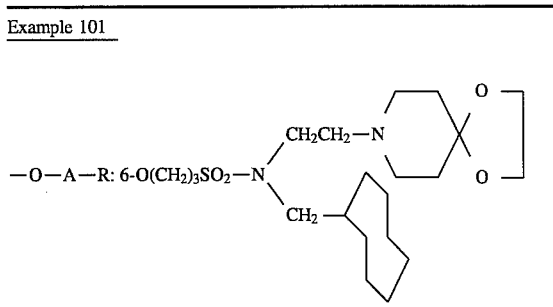

W: oxygen atom
Crystal form: white powder   Free form
Melting point: 154.5–155.5° C.

Example 102

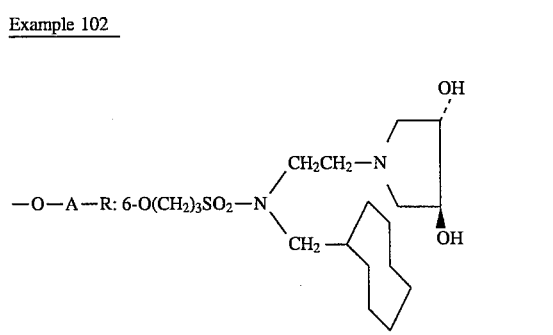

W: oxygen atom
Crystal form: white powder   Free form
Melting point: 107–110° C.

Example 103

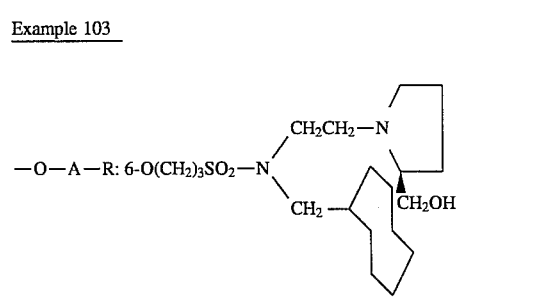

W: oxygen atom
Crystal form: light yellow powder   Free form
Melting point: 129–131° C.

Example 104

TABLE 45-continued

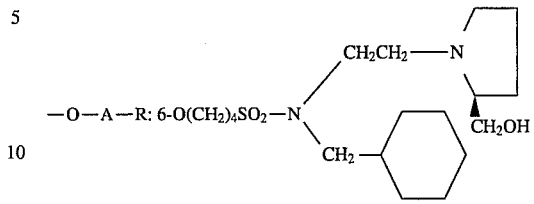

W: oxygen atom
Crystal form: white powder   Free form
Melting point: 163–164.5° C.

TABLE 46

Example 105

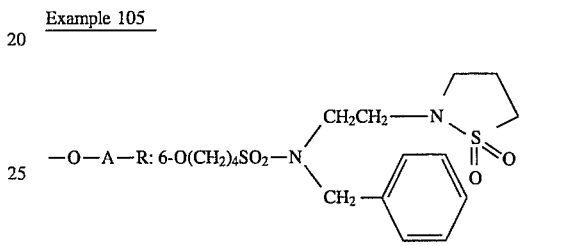

W: oxygen atom
Crystal form: light yellow powder   Free form
Melting point: 156–158.5° C.

Example 106

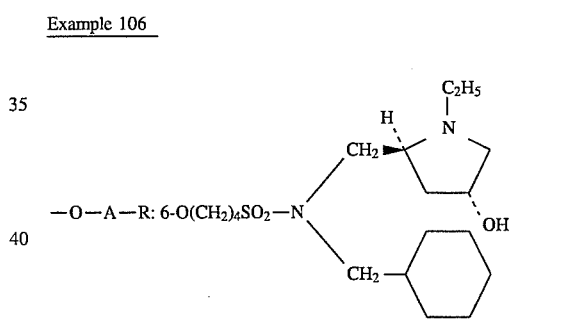

W: oxygen atom
Crystal form: white powder   Free form
Melting point: 141.5–143.5° C.

Example 107

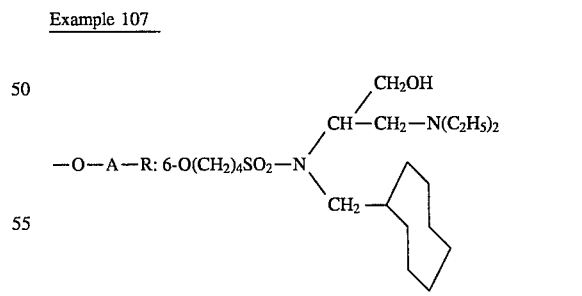

W: oxygen atom
Crystal form: light yellow powder   Free form
Melting point: 138.5–141° C.
Recrystallization solvent: diethyl ether Example 108

TABLE 46-continued

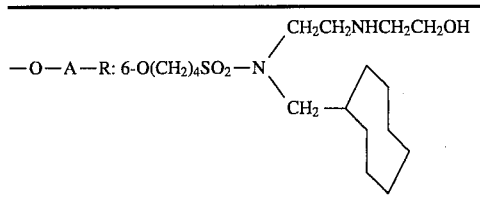

W: oxygen atom
Crystal form: light yellow powder   Free form
Melting point: 133–136° C.

TABLE 47

Example 109

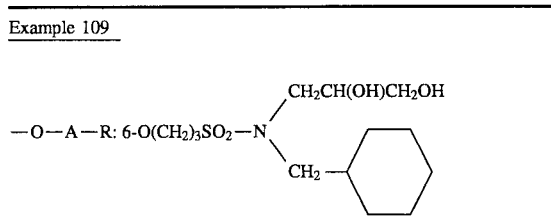

W: oxygen atom
Crystal form: white powder   Free form
Melting point: 181.5–183.5° C.
Recrystallization solvent: water-ethanol Example 110

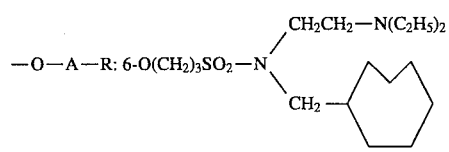

W: oxygen atom
Crystal form: light yellow powder   Free form
Melting point: 133–134° C.
Recrystallization solvent: diethyl ether Example 111

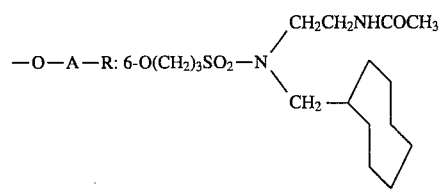

W: oxygen atom
Crystal form: white powder   Free form
Melting point: 180–182.5° C.
Recrystallization solvent: methanol-diethyl ether Example 112

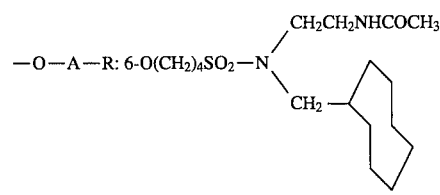

W: oxygen atom
Crystal form: light yellow powder   Free form
Melting point: 109° C.

TABLE 48

Example 113

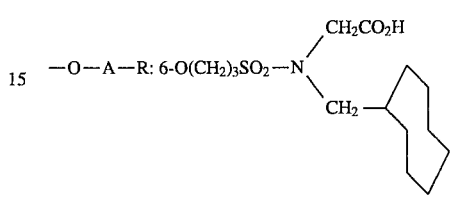

W: oxygen atom
Crystal form: light yellow powder   Free form
Melting point: 141° C. (decomposed)

Example 114

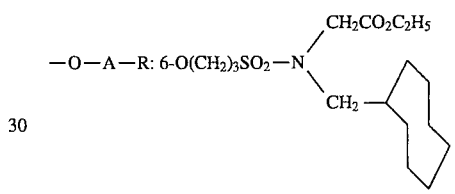

W: oxygen atom
Crystal form: light yellow powder   Free form
Melting point: 128° C.

Example 115

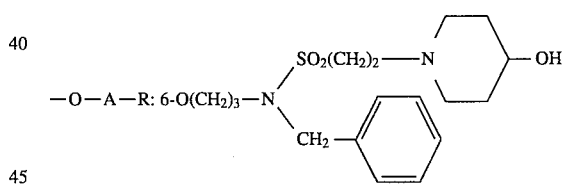

W: oxygen atom
Crystal form: light yellow powder   Free form
Melting point: 135–137° C.
Recrystallization solvent: methanol Example 116

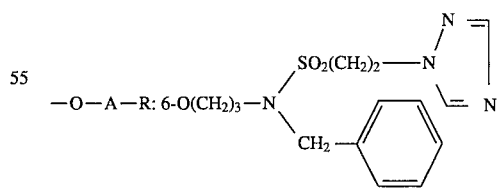

W: oxygen atom
Crystal form: white powder   Free form
Melting point: 156–158° C.
Recrystallization solvent: ethyl acetate

TABLE 49

Example 117

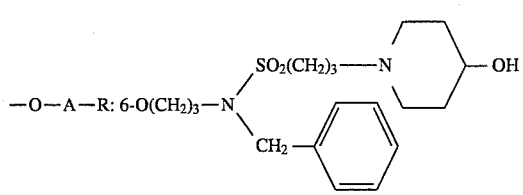

W: oxygen atom
Crystal form: white powder       Free form
Melting point: 143–145° C.
Recrystallization solvent: ethyl acetate

Example 118

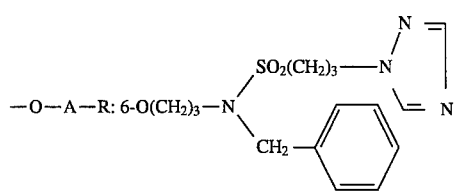

W: oxygen atom
Crystal form: light yellow powder       Free form
Melting point: 130–132° C.
Recrystallization solvent: methanol

Example 119

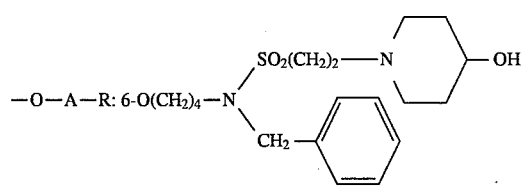

W: oxygen atom
Crystal form: light yellow powder       Free form
Melting point: 158–160° C.
Recrystallization solvent: ethyl acetate

Example 120

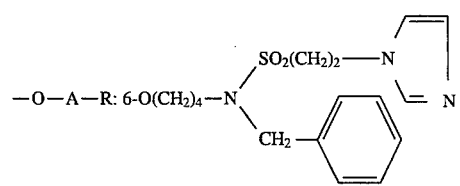

W: oxygen atom
Crystal form: light yellow powder       Free form
Melting point: 154–155° C.
Recrystallization solvent: ethyl acetate

TABLE 50

Example 121

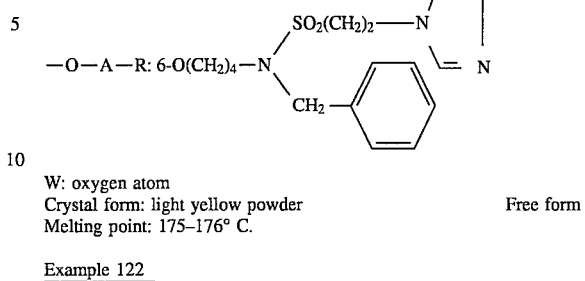

W: oxygen atom
Crystal form: light yellow powder       Free form
Melting point: 175–176° C.

Example 122

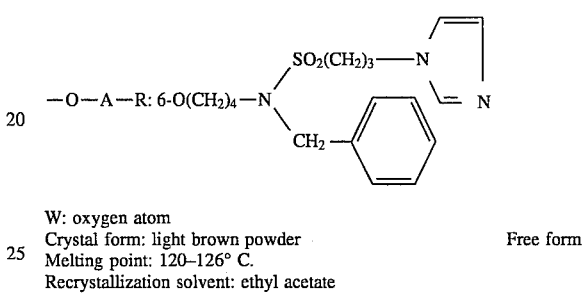

W: oxygen atom
Crystal form: light brown powder       Free form
Melting point: 120–126° C.
Recrystallization solvent: ethyl acetate

Example 123

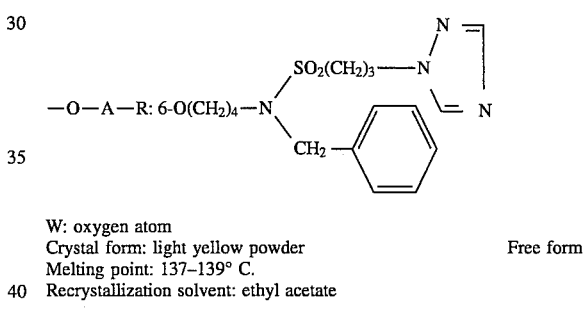

W: oxygen atom
Crystal form: light yellow powder       Free form
Melting point: 137–139° C.
Recrystallization solvent: ethyl acetate

Example 124

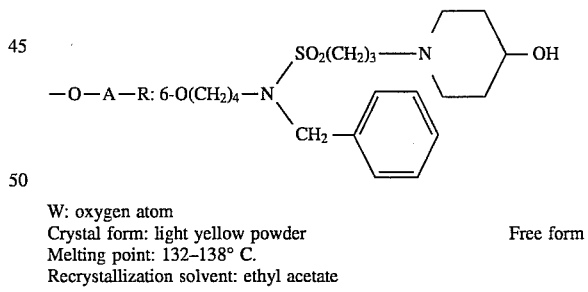

W: oxygen atom
Crystal form: light yellow powder       Free form
Melting point: 132–138° C.
Recrystallization solvent: ethyl acetate

TABLE 51

Example 125

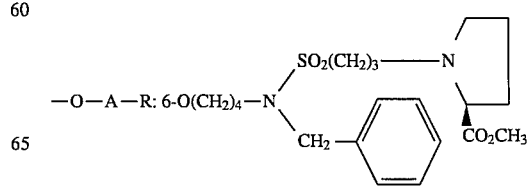

TABLE 51-continued

W: oxygen atom
Crystal form: light brown powder   Free form
Melting point: 127–129° C.
Recrystallization solvent: ethyl acetate Example 126

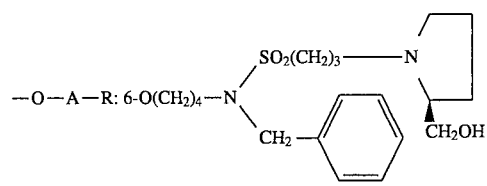

W: oxygen atom
Crystal form: light yellow powder   Free form
Melting point: 84–90° C.
Recrystallization solvent: diethyl ether Example 127

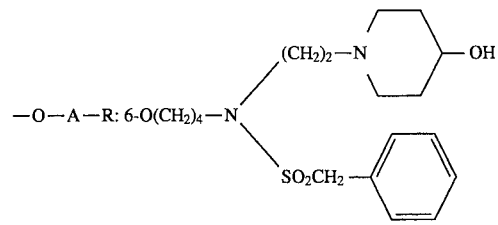

W: oxygen atom
Crystal form: white powder   Free form
Melting point: 206–208° C.
Recrystallization solvent: methanol Example 128

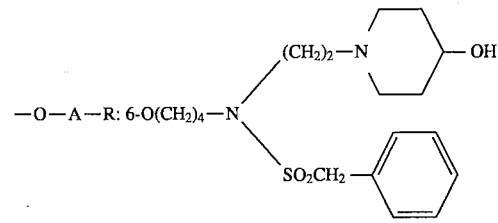

W: oxygen atom
Crystal form: colorless acicular   Free form
Melting point: 105–109° C.
Recrystallization solvent: ethyl acetate

TABLE 52

Example 129

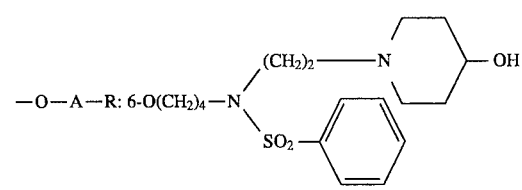

W: oxygen atom
Crystal form: white powder   Free form

TABLE 52-continued

Melting point: 123–125° C.
Recrystallization solvent: methanol

Example 130

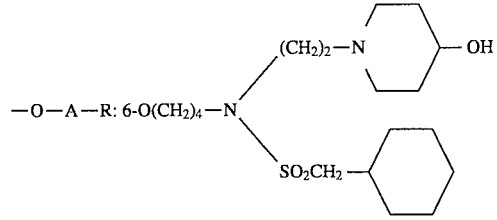

W: oxygen atom
Crystal form: light yellow powder   Free form
Melting point: 179–181° C.
Recrystallization solvent: ethyl acetate Example 131

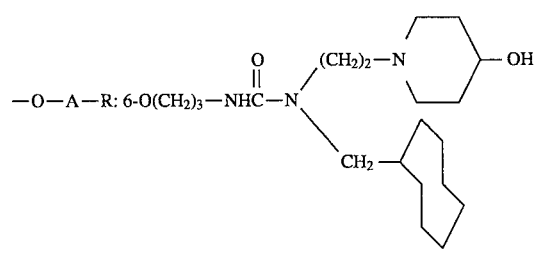

W: oxygen atom
Crystal form: white amorphous   Free form
                                NMR (13)

Example 132

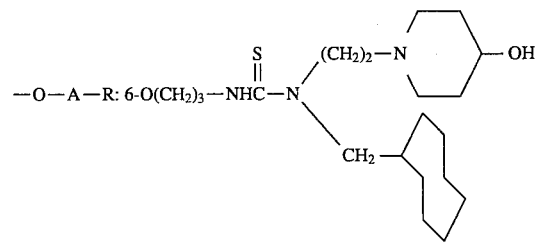

W: oxygen atom
Crystal form: white powder   Free form
Melting point: 138–138.5° C.

TABLE 53

Example 133

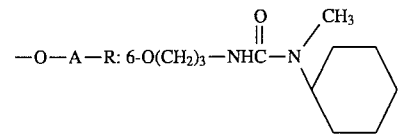

W: oxygen atom
Crystal form: white powder   Free form
Melting point: 156–158.5° C.
Recrystallization solvent: diethyl ether

TABLE 53-continued

Example 134

—O—A—R: 7-O(CH$_2$)$_4$—N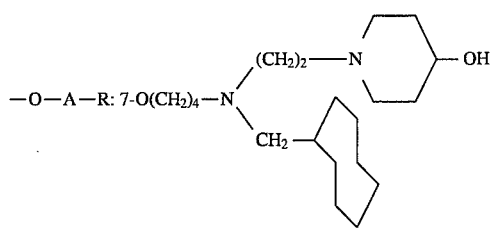

W: oxygen atom
Crystal form: white powder    Free form
Melting point: 138.5–139.5° C.
Recrystallization solvent: ethyl acetate Example 135

—O—A—R: 6-O(CH$_2$)$_3$—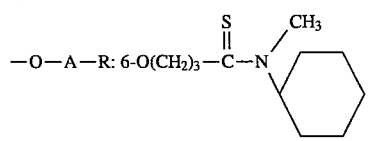

W: oxygen atom
Crystal form: yellow powder    Free form
Melting point: 170–172° C.

Example 136

—O—A—R: 6-O(CH$_2$)$_4$—N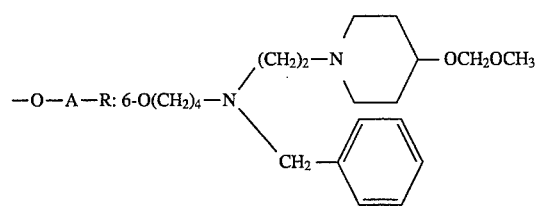

W: oxygen atom
Crystal form: light yellow oil    Free form
NMR (14)

TABLE 54

Example 137

—O—A—R: 6-O(CH$_2$)$_4$—N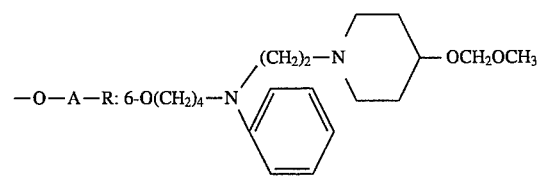

W: oxygen atom
Crystal form: light yellow oil    Free form
NMR (15)

Example 138

—O—A—R: 6-O(CH$_2$)$_3$SO$_2$—N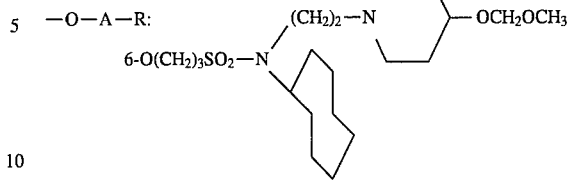

W: oxygen atom
Crystal form: light yellow oil    Free form
NMR (16)

Example 139

—O—A—R: 6-O(CH$_2$)$_3$—NHCN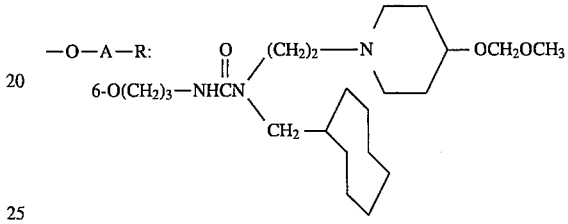

W: oxygen atom
Crystal form: brown oil    Free form
NMR (17)

Example 140

—O—A—R: 6-O(CH$_2$)$_4$—NH(CH$_2$)$_2$—N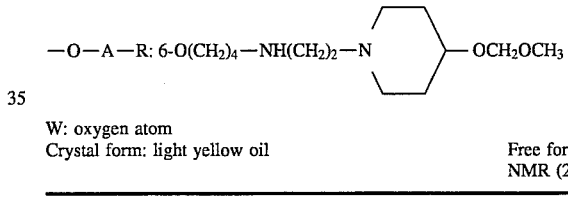—OCH$_2$OCH$_3$

W: oxygen atom
Crystal form: light yellow oil    Free form
NMR (20)

TABLE 55

Example 141

—O—A—R: 6-O(CH$_2$)$_4$—N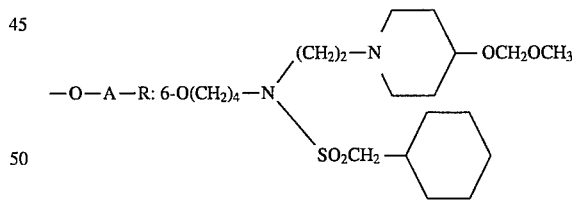

W: oxygen atom
Crystal form: light yellow oil    Free form
NMR (21)

Example 142

—O—A—R: 6-O(CH$_2$)$_4$—N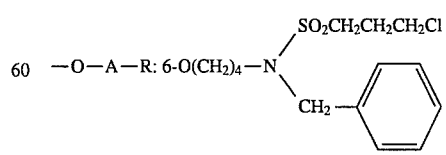

W: oxygen atom
Crystal form: white powder    Free form
NMR (22)

TABLE 55-continued

Example 143

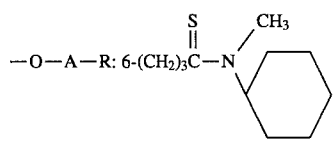

W: oxygen atom
Crystal form: yellow powder
Melting point: 167–170° C.

Free form

Example 144

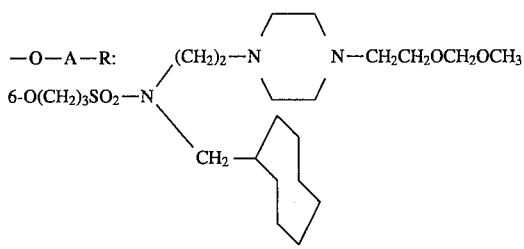

W: oxygen atom
Crystal form: light yellow oil

Free form
NMR (18)

TABLE 56

Example 145

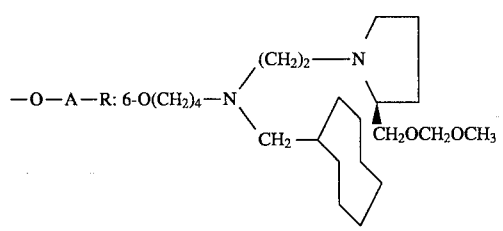

W: oxygen atom
Crystal form: colorless oil

Free form
NMR (19)

(1) $^1$H-NMR (CDCl$_3$) δ; 1.2–2.0 (21H, m), 2.15–2.25 (2H, m), 2.7–2.9 (2H, m), 3.1–3.3 (4H, m), 3.3–3.5 (2H, m), 3.6–3.7 (1H, m), 3.9–4.1 (2H, m), 6.71 (1H, d, J=9.5 Hz), 6.9–7.4 (3H, m), 7.74 (1H, d, J=9.5 Hz).

(2) $^1$H-NMR (CDCl$_3$) δ; 1.4–1.9 (10H, m), 2.1–2.3 (2H, m), 2.45–2.55 (4H, m), 2.6–2.7 (2H, m), 2.7–2.8 (2H, m), 3.54 (2H, s), 3.65–3.75 (2H, m), 3.86 (6H, s), 3.97 (2H, t, J=6.5 Hz), 6.70 (1H, d, J=9.5 Hz), 6.75–6.85 (H, m), 6.91 (H, m), 6.97 (1H, d, J=2.5 Hz), 7.13 (1H, dd, J=2.5 Hz, 9.0 Hz), 7.29 (1H, d, J=9.0 Hz), 7.73 (1H, d, J=9.5 Hz).

(3) $^1$H-NMR (CDCl$_3$) δ; 1.35–1.7 (6H, m), 1.7–2.0 (4H, m), 2.05–2.25 (2H, m), 2.4–2.65 (4H, m), 2.65–2.85 (4H, m), 3.6–3.8 (3H, m), 3.97 (2H, t, J=6 Hz), 6.72 (1H, d, J=9.5 Hz), 6.97 (1H, d, J=2.5 Hz), 7.05–7.2 (2H, m), 7.37 (1H, d, J=9 Hz), 7.38–7.58 (1H, m), 7.63 (1H, dt, J=7.5 Hz, 1.5 Hz), 7.75 (1H, d, J=9.5 Hz), 8.41–8.61 (1H, m).

(4) $^1$H-NMR (CD$_3$OD) δ; 1.40–1.95 (10H, m), 2.25 (2H, brt, J=8.5 Hz), 2.40–2.90 (8H, m), 3.50–3.70 (1H, m), 3.85 (2H, s), 4.03 (2H, t, J=6.5 Hz), 6.60 (1H, d, J=9.5 Hz), 6.94 (2H, brs), 7.15–7.35 (4H, m), 7.92 (1H, d, J=9.5 Hz).

(5) $^1$H-NMR (CDCl$_3$) δ; 1.15–2.00 (25H, m), 2.20 (2H, brd, J=6.5 Hz), 2.45–2.60 (2H, m), 2.85 (2H, brs), 3.05–3.50 (4H, m), 4.01 (2H, t, J=6.5 Hz), 6.71 (1H, d, J=9.5 Hz), 7.00 (1H, brs), 7.10–7.40 (3H, m), 7.76 (1H, d, J=9.5 Hz).

(6) $^1$H-NMR (CD$_3$OD) δ; 1.15–1.90 (23H, m), 2.01 (2H, brt, J=12 Hz), 2.10–2.35 (2H, m), 2.29 (6H, s), 2.35–2.60 (6H, m), 3.01 (2H, brd, J=12 Hz), 4.06 (2H, t, J=6 Hz), 6.61 (1H, d, J=9.5 Hz), 7.15–7.35 (3H, m), 7.92 (1H, d, J=9.5 Hz).

(7) $^1$H-NMR (CD$_3$OD) δ; 0.90–1.10 (2H, m), 1.15–2.15 (19H, m), 2.60–3.75 (13H, m), 4.07 (2H, J=6 Hz), 6.62 (1H, d, J=9.5 Hz), 7.15–7.35 (3H, m), 7.94 (1H, d, J=9.5 Hz).

(8) $^1$H-NMR (CD$_3$OD) δ; 1.45–2.10 (10H, m), 2.25–2.50 (2H, m), 2.61 (1H, brs), 2.75–3.30 (5H, m), 3.98 (3H, s), 3.03 (3H, s), 3.77 (1H, brs), 4.06 (2H, brs), 4.38 (1H, brd, J=12 Hz), 6.51 (1H, d, J=9.5 Hz), 7.16 (2H, brs), 7.29 (1H, brs), 7.40–7.60 (5H, m), 7.91 (1H, d, J=9.5 Hz).

(9) $^1$H-NMR (CDCl$_3$) δ; 1.40–2.05 (8H, m), 2.15–2.70 (5H, m), 2.90–3.20 (2H, m), 3.35–3.80 (6H, m), 3.97 (2H, t, J=6.5 Hz), 6.70 (1H, d, J=9.5 Hz), 6.98 (1H, d, J=2.5 Hz), 7.10–7.60 (6H, m), 7.74 (2H, d, J=9.5 Hz).

(10) $^1$H-NMR (CD$_3$OD) δ; 1.4–1.9 (6H, m), 2.3–2.7 (16H, m), 3.55–3.75 (4H, m), 4.01 (2H, t, J=6.5 Hz), 6.01 (1H, d, J=9.5 Hz), 7.15–7.45 (8H, m), 7.91 (1H, d, J=9.5 Hz).

(11) $^1$H-NMR (CD$_3$OD) δ; 1.10–1.95 (19H, m), 2.24 (2H, d, J=7 Hz), 2.57 (2H, t, J=7 Hz), 2.70 (2H, t, J=6 Hz), 2.90–3.10 (4H, m), 3.74 (2H, t, J=5.5 Hz), 4.07 (2H, t, J=6 Hz), 6.62 (1H, d, J=9.5 Hz), 7.15–7.35 (3H, m), 7.92 (1H, d, J=9.5 Hz).

(12) $^1$H-NMR (CD$_3$OD) δ; 1.30–1.75 (6H, m), 2.46 (2H, t, J=6 Hz), 2.77 (2H, t, J=6 Hz), 3.60 (2H, s), 3.96 (2H, t, J=6 Hz), 4.05 (2H, t, J=6 Hz), 6.61 (1H, d, J=9.5 Hz), 6.91 (1H, s), 7.05 (1H, s), 7.10–7.35 (8H, m), 7.60 (1H, s), 7.91 (1H, d, J=9.5 Hz).

(13) $^1$H-NMR (CDCl$_3$) δ; 1.2–1.9 (19H, m), 1.95–2.1 (2H, m), 2.15–2.25 (2H, m), 2.49 (2H, t), 2.7–2.85 (2H, m), 3.1 (2H, d, J=7.5 Hz), 3.27 (2H, t), 3.3–3.45 (2H, m), 3.65–3.8 (1H, m), 4.07 (2H, t, J=6 Hz), 6.7 (1H, d, J=9.5 Hz), 7.00 (1H, d, J=2.5 Hz), 7.15 (1H, dd, J=2.5 Hz, 9 Hz), 7.3 (1H, d, J=9 Hz), 7.73 (1H, d, J=9.5 Hz).

(14) $^1$H-NMR (CDCl$_3$) δ; 1.5–1.9 (8H, m), 2.12 (2H, m), 2.5 (4H, m), 2.6 (2H, m), 2.7 (2H, m), 3.36 (3H, m), 3.6 (1H, m), 3.60 (2H, s), 3.95 (2H, t, J=6 Hz), 4.67 (2H, s), 6.71 (H, d, J=9.5 Hz), 6.93 (1H, d, J=2.5 Hz), 7.12 (1H, dd, 2.5 Hz, 9 Hz), 7.2–7.3 (6H, m).

(15) $^1$H-NMR (CDCl$_3$) δ; 1.7–2.0 (8H, m), 2.3 (2H, m), 2.5 (2H, m), 2.8 (2H, m), 3.37 (3H, m), 3.4 (2H, m), 3.5 (2H, m), 3.6 (1H, m), 4.02 (2H, t, J=6 Hz), 4.68 (2H, s), 6.63–6.73 (4H, m), 6.97 (1H, d, J=2.5 Hz), 7.12–7.23 (3H, m), 7.33 (1H, d, J=9 Hz), 7.74 (1H, d, J=9.5 Hz).

(16) $^1$H-NMR (CDCl$_3$) δ; 7.75 (1H, d, J=9.5 Hz), 7.35 (1H, d, J=9 Hz), 7.15 (1H, dd, J=9 Hz, 2.6 Hz), 7.01 (1H, d, J=2.6 Hz), 6.73 (1H, d, J=9.5 Hz), 4.68 (2H, s), 4.15 (2H, t, J=5.8 Hz), 3.75–3.95 (1H, m), 3.58–3.69 (1H, m), 3.37 (3H, s), 3.22–3.35 (4H, m), 2.75–2.90 (2H, m), 2.55–2.68 (2H, m), 2.18–2.40 (4H, m), 1.40–2.05 (18H, m).

(17) $^1$H-NMR (CDCl$_3$) δ; 7.73 (1H, d, J=9.5 Hz), 7.40 (1H, br), 7.29 (1H, d, J=11.4 Hz), 7.15 (1H, dd, J=11.4 Hz, 2.5 Hz), 7.01 (1H, d, J=2.5 Hz), 6.70 (1H, d, J=9.5 Hz), 4.65 (2H, s), 4.06 (2H, t, J=6.2 Hz), 3.15–3.65 (8H, m), 3.10 (2H, d, J=7.5 Hz), 2.65–2.90 (2H, m), 2.35–2.60 (2H, m), 2.10–2.35 (2H, m), 1.97–2.10 (2H, t, J=5.6 Hz), 1.10–1.97 (19H, m).

(18) $^1$H-NMR (CDCl$_3$) δ; 1.15–1.85 (15H, m), 2.2–2.4 (2H, m), 2.45–2.8 (4H, m), 2.85–3.1 (4H, m), 3.15–3.4 (10H, m), 4.05–4.2 (4H, m), 4.55–4.7 (4H, m), 6.72 (1H, d, J=9.5 Hz), 7.0 (1H, d, J=2.5 Hz) 7.15 (1H, dd, J=2.5 Hz, 9.0 Hz), 7.32 (1H, d, J=9 Hz), 7.74 (1H, d, J=9.5 Hz).

(19) ¹H-NMR (CDCl₃) δ; 1.10–2.00 (23H, m), 2.10–2.65 (8H, m), 2.80–3.25 (2H, m), 3.36 (3H, s), 3.45–3.65 (2H, m), 3.95–4.10 (2H, m), 4.63 (2H, s), 6.70 (1H, d, J=9.5 Hz), 6.99 (1H, brs), 7.15 (1H, brd, J=9 Hz), 7.31 (1H, d, J=9 Hz), 7.74 (1H, d, J=9.5 Hz).

(20) ¹H-NMR (CDCl₃) δ; 1.5–1.7 (2H, m), 1.75–1.9 (4H, m), 2.15–2.3 (2H, m), 2.6–2.7 (2H, m), 2.7–2.8 (2H, m), 2.85–2.95 (4H, m), 3.45 (3H, s), 3.5–3.65 (1H, m), 3.95–4.05 (2H, m), 4.65 (2H, s), 6.64 (1H, d, J=9.5 Hz), 6.91 (1H, d, J=2.5 Hz), 7.05 (1H, dd, J=2.5 Hz, 9.0 Hz), 7.39 (1H, d, J=9.0 Hz), 7.70 (1H, d, J=9.5 Hz), 8.00 (1H, br).

(21) ¹H-NMR (CDCl₃) δ; 1.0–2.0 (19H, m), 2.1–2.3 (2H, m), 2.4–2.6 (2H, m), 2.7–2.9 (2H, m), 3.2–3.4 (4H, m), 3.36 (3H, s), 3.5–3.65 (1H, m), 3.95–4.05 (2H, m), 4.67 (2H, s), 6.71 (1H, d, J=9.5 Hz), 7.13 (1H, dd, J=2.5 Hz, 9.0 Hz), 7.34 (1H, d, J=9.0 Hz), 7.75 (1H, d, J=9.5 Hz).

(22) ¹H-NMR (CDCl₃) δ; 1.6–1.7 (4H, m), 2.25–2.35 (2H, m), 3.11 (2H, t, J=7.5 Hz), 3.25–3.35 (2H, m), 3.67 (2H, t, J=6.0 Hz), 3.9–4.0 (2H, m), 4.44 (2H, s), 6.71 (2H, d, J=9.5 Hz), 6.92 (1H, d, J=2.5 Hz), 7.09 (1H, d, J=2.5 Hz, 9.0 Hz), 7.3–7.4 (6H, m), 7.73 (1H, d, J=9.5 Hz).

Example 146

Using appropriate starting materials, the compounds of Examples 4, 14–75, 115–130, 137, 140–142 and 145 were obtained in the same manners as in Examples 1 and 8.

Example 147

Using appropriate starting materials, the compounds of Examples 14–18, 20–26, 28–42, 48–52, 54–55, 71–75, 78–96, 99, 102–104, 106, 115, 117, 119, 124, 126–132 and 134 were obtained in the same manner as in Example 2.

Example 148

Using appropriate starting materials, the compound of Example 113 was obtained in the same manner as in Example 3.

Example 149

Using appropriate starting materials, the compounds of Examples 76–92, 94–114 and 144 were obtained in the same manner as in Example 5.

Example 150

Using appropriate starting materials, the compounds of Examples 14–71, 76–141 and 143–145 were obtained in the same manners as in Examples 6 and 9.

Examples 151

Using appropriate starting materials, the compounds of Examples 115–122 and 124–126 were obtained in the same manner as in Example 7.

Example 152

Using appropriate starting materials, the compound of Example 132 was obtained in the same manner as in Example 10.

Example 153

Using appropriate starting materials, the compounds of Examples 131 and 133 were obtained in the same manner as in Example 11.

Pharmacological Test I

The platelets aggregation inhibitory activity of each test compound was measured by the method of Born et al. [J. Physiol., London, 162, 67 (1962)], using Platelets Aggregation Tracer manufactured by Nikoh Bioscience Co., Ltd.

9 volumes of a blood collected from man was mixed with 1 volume of a 3.8% aqueous sodium citrate solution. Part of the mixture was subjected to centrifugation at 1,100 rpm for 10 minutes to obtain a platelet rich plasma (PRP). The remainder of the mixture was also subjected to centrifugation at 3,000 rpm for 10 minutes to obtain a platelet poor plasma (PPP).

The number of platelets in the PRP was measured using Coulter Counter manufactured by Coulter Electronics Inc. Then, the PRP was diluted with the PPP so that the number of platelets in the dilution became 300,000, whereby a PRP solution was prepared.

200 μl of this PRP solution and 2 ml of a solution containing a test compound at a given concentration were placed in an aggregation measurement cell and heated at 37° C. for 1 minute. Thereto was added 20 μl of adenosine diphosphate (ADP manufactured by Sigma Co.) or a collagen suspension (Collagen Reagent manufactured by Horm, Hormon-Chemie, Gmbh) to induce aggregation of platelets. The resulting mixture in the cell was measured for change of transmittance, after which a platelets aggregation curve was prepared. Incidentaly, the concentration of ADP or collagen was selected so that the final Concentration became 7.5 μM or 20 μg/ml.

Using the platelets aggregation curve, there was calculated a maximum aggregation rate (MAR) of platelets using the followoing formula:

$$MAR=[(b-a)/(c-a)]\times 100$$

wherein a represents a transmittance of the PRP obtained in the same manner; c represents a transmittance of the PPP obtained in the same manner; and b represents a transmittance at the maximum change, of the PRP solution containng the test compound and the aggregation inducer.

A MAR was also calculated as above, for the control containing no test compound.

Using the above two MARs, there were calculated platelets aggregation inhibitions (%) of each test compound at various concentrations using the following formula.

Inhibition=[1-(MAR of PRP solution containing test compound)/ (MAR of PRP solution containing no test compound)]×100

Using the above obtained platelets aggregation inhibitions (%) of each test compound at various concentrations, there was calculated a concentration ($IC_{50}$) of each test compound for 50% platelets aggregation inhibition.

The $IC_{50}$ values obtained for some of the compounds obtained in the Examples, each used as a test compound are shown in Table 57 and Table 58.

TABLE 57

| Test compound | $IC_{50}$ (μM) ADP | Collagen |
| --- | --- | --- |
| Example 15 | 10 | 3.6 |
| Example 16 | 6.3 | 7.4 |
| Example 19 | 6.1 | 5.3 |
| Example 20 | 2 | 1.2 |
| Example 21 | 4.2 | 3.1 |
| Example 23 | 8 | 9.5 |
| Example 24 | 14 | 14 |
| Example 26 | 15 | 14 |

TABLE 57-continued

| Test compound | IC$_{50}$ (µM) ADP | Collagen |
|---|---|---|
| Example 27 | 6.7 | 7.7 |
| Example 29 | 12 | 6.3 |
| Example 30 | 3.7 | 2 |
| Example 32 | 4.8 | 6.1 |
| Example 33 | 5.6 | 9.1 |
| Example 35 | 11 | 11 |
| Example 36 | 11 | 20 |
| Example 40 | 13 | 10 |
| Example 41 | 8.7 | 11 |
| Example 42 | 20 | 13 |
| Example 45 | 22 | 25 |
| Example 46 | 20 | 20 |
| Example 47 | 25 | 29 |
| Example 49 | 6.9 | 22 |
| Example 53 | 11 | 13 |
| Example 55 | 3.7 | 2.6 |
| Example 56 | 14 | 7.7 |
| Example 57 | 18 | 17 |
| Example 58 | 3.8 | 4.8 |
| Example 60 | 15 | 5.3 |
| Example 61 | 4.9 | 6.3 |
| Example 62 | 18 | 17 |
| Example 64 | 9 | 10 |
| Example 65 | 11 | 14 |
| Example 67 | 4.5 | 2.9 |
| Example 68 | 15 | 7.1 |
| Example 69 | 15 | 9.5 |
| Example 70 | 40 | 22 |
| Example 71 | 18 | 7.4 |
| Example 73 | 25 | 6.9 |
| Example 74 | 17 | 20 |
| Example 75 | 9.1 | 13 |
| Example 77 | 2.1 | 4.9 |
| Example 78 | 1.4 | 0.38 |
| Example 79 | 1.3 | 2.5 |
| Example 80 | 13 | 15 |
| Example 81 | 6.1 | 11 |
| Example 82 | 4.5 | 3.8 |
| Example 83 | 11 | 4.3 |
| Example 84 | 9.5 | 9.1 |

TABLE 58

| Test compound | IC$_{50}$ (µM) ADP | Collagen |
|---|---|---|
| Example 85 | 2.1 | 0.57 |
| Example 86 | 8 | 12 |
| Example 87 | 4.7 | — |
| Example 88 | 2.8 | 1.4 |
| Example 89 | 7.7 | 3.8 |
| Example 90 | 5.3 | 5.4 |
| Example 93 | 1.2 | 2.6 |
| Example 94 | 1.4 | 2.3 |
| Example 95 | 10 | 7.1 |
| Example 96 | 8.7 | 6.5 |
| Example 97 | 14 | 18 |
| Example 98 | 9.1 | 12 |
| Example 99 | 2.9 | 3.5 |
| Example 100 | 13 | 6.5 |
| Example 101 | 2.9 | 3.2 |
| Example 102 | 9.5 | 15 |
| Example 103 | 2.6 | 3.2 |
| Example 104 | 3.5 | 2.3 |
| Example 105 | 2.2 | 1.1 |
| Example 106 | 1.4 | 0.9 |
| Example 107 | 3.4 | 3.2 |
| Example 108 | 2.9 | 2 |
| Example 109 | 4.9 | 6.3 |
| Example 110 | 4.7 | 8.3 |
| Example 111 | 2.2 | 2.9 |
| Example 112 | 0.83 | 0.69 |

TABLE 58-continued

| Test compound | IC$_{50}$ (µM) ADP | Collagen |
|---|---|---|
| Example 114 | 6.5 | 4 |
| Example 119 | 20 | 20 |
| Example 122 | 22 | 29 |
| Example 123 | 17 | 9.5 |
| Example 126 | 10 | 15 |
| Example 128 | 25 | 20 |
| Example 130 | 14 | 13 |
| Example 131 | 2.4 | 1.3 |
| Example 132 | 2.4 | 1.8 |
| Example 133 | 2.9 | — |
| Example 135 | 22 | — |
| Example 143 | 3.8 | 2.3 |

Pharmacological Test II

The heart rate-increasing activity and blood pressure hypotensive activity of each test compound were measured by the following method, using mongrel dogs each weighing 10–20 kg. That is, said dogs were anesthesized by intravenous injection of pentobarbital sodium, then fixed at the back, and tested under artificial respiration. The blood pressures of the dogs were measured by a blood pressure measuring transducer (P23×L manufactured by Gould Statham Instruments, Inc.) via cannula inserted into the femoral artery. The heart rates of the dogs were measured using the pulse wave of the blood pressure of each dog, via a tachometer. The signals of these testng apparatuses were recorded on a thermal pen-type recorder (Recti-Horize 8K manufactured by Nippon Denki-San-ei Sha).

Some of the compounds obtained in the above Examples were used as test compounds. They were dissolved in N, N'-dimethylformamide, and each solution was administered to test dogs via a cannula inerted into the femoral artery of each dog, in such an amount (amount of test compound) of 300 µg/kg. Then, the heart rate of each dog was measured according to the above method and a maximum change in heart rate was calculated.

The results are shown in Table 59.

TABLE 59

| Test compound | Maximum change in heart rate (beats/minute) dose: 300 mg/kg |
|---|---|
| Example 15 | 1 |
| Example 16 | 1 |
| Example 19 | 24 |
| Example 23 | −2 |
| Example 27 | 7 |
| Example 28 | 0 |
| Example 61 | 17 |
| Example 62 | 2 |
| Example 68 | 30 |
| Example 83 | 9 |
| Example 85 | 13 |
| Example 109 | 16 |

Pharmacological Test III

A blood was collected from a healthy man with normal platelets function by addition of 0.1% disodium ethylenediaminetetraacetate (EDTA.4Na) and immediately subjected to separation of a platelet rich plasma (PRP). The PRP was washed twice with a Tyrode's buffer solution (50mM TRIS, 0.1% EDTA, Ca (-), Mg (-), 0.14% BSA added, pH=7.4), and suspended in the buffer solution so that the number of platelets in the resulting suspension became 300, 000/ml, to obtain a platelets suspension (EDTA-WP). 4 mg of Type I manufactured by Sigma Co., derived from a bovine skin was dissolved in 0.25 ml of acetic acid (83.5 mM); 8 ml of distilled water was added thereto; an ultrasonic wave was applied to the mixture at 4° C. for 2 minutes; 5 ml of the supernatant liquid was separated as a collagen solution. Each test compound was dissolved in dimethylformamide (DMF) so as to give a concentration of at least $2 \times 10^{-12}$ M when possible, to prepare a test compound solution. The change in turbidity of platelets suspension was recorded as a change in transmitted light emitted from a glass cell containing the suspension, using a platelets aggregation tracer manufactured by Nikoh Bioscience K.K., generally used in the test of platelets aggregation function, whereby the adherence of platelets was measured. Incidentally, in recoridng the change in transmitted light, the sensitivity of the recorder was 5 times as high as that used generally. 200 μl of the EDTA-WP was placed in a glass cell exclusively used for the above platelets aggregation tester. Further, 1 μl of the test compound solution was added. The mixture was incubated at room temperature for 5 minutes. Then, the cell was set in the platelets aggregation tracer and was allowed to stand for 1 minute until the temperature became 37° C. Thereafter, about 20 μl (50 μg/ml) of the collagen solution was added, and the adherence of platelets were measured.

The inhibitions (%) of collagen-induced platelets adhesion by each test compound at various concentrations were calculated using the following formula.

Inhibition (%)=[1-(platelets adherence when test compound added)/ (platelets adherence when no test compound added)]× 100

The results are shown in Table 60.

TABLE 60

| Test compound | Dose (μM) | Inhibition (%) of collagen-induced platelets adherence |
| --- | --- | --- |
| Example 16 | 10 | 48 |
| Example 20 | 10 | 49 |
| Example 28 | 10 | 48 |
| Example 75 | 300 | 57 |
| Example 85 | 3 | 50 |
| Example 86 | 10 | 47 |
| Example 119 | 10 | 40 |
| Example 123 | 10 | 39 |
| Example 130 | 10 | 43 |
| Example 134 | 10 | 45 |
| Example 53 | 30 | 35 |
| Example 76 | 30 | 35 |
| Example 62 | 100 | 54 |
| Example 61 | 30 | 35 |
| Example 27 | 30 | 40 |
| Example 64 | 30 | 31 |
| Example 73 | 100 | 36 |
| Example 121 | 30 | 38 |

Pharmacological Test IV

The cyclic AMP phosphodiesterase inhibitory activity of the present compound was measured in accordance with the method described in Biochimica et Biophysica Acta Vol. 429, pp. 485–497 (1976) and Biochemical Medicine Vol. 10, pp. 301–311 (1974).

That is, the PRP sample of man used in Pharmacological Test I was subjected to further centrifugation at 3,000 rpm for 10 minutes. To the resulting platelets was added 10 ml of a solution (pH=74) obtained by adding 1 mM of $MgCl_2$ to a TRIS-HCl buffer solution (50 mM). The mixture was subjected to homogenization to grind the platelets in the mixture; then, freezing and thawing were conducted twice, followed by an ultrasonic wave treatment and ultracentrifugation in this order; the resulting supernatant liquid was used as a crude enzyme solution.

The crude enzyme solution was poured into a DEAE-cellulose column buffered with a TRIS-HCl buffer solution (pH=6.0, 50 mM), and washing and elution was conducted with 30 ml of the same buffer solution. Then, elution was conducted with a sodium acetate-TRIS-HCl buffer solution by a linear gradient method at a flow rate of 0.5 ml/minute to obtain fractions each of 5 ml (total eluate amount=about 300 ml). Thus, there was obtained a fraction having a weak activity of 2 nM/ml/min or less at a high cyclic AMP substrate concentration of 100 μM and a strong activity of 100 pM/ml/min or more at a low cyclic AMP substrate concentration of 0.4 μM, and the fraction was used as a cyclic AMP phosphodiesterase solution.

0.1 ml of one of aqueous solutions containing each test compound at various concentrations was mixed with a TRIS-HCl buffer solution (pH=8.0, 40 mM, contains 50 μg of a bovine serum albumin and 4 mM of $MgCl_2$) cntaining 0.4 μM of cyclic AMP (tritium cyclic AMP), to prepare 0.2 ml of a substrate solution.

To the substrate solution was added 0.2 ml of the cyclic AMP phosphodiesterase solution. The mixture was subjected to a reaction at 30° C. for 20 minutes to convert the tritium cyclic AMP to tritium 5'-AMP. The reaction mixture was immersed in boiling water to terminate the reaction, and then cooled in ice water. Thereto was added 0.05 ml of a snake venom (1 mg/ml), and the mixture was subjected to a reaction at 30° C. for 10 minutes to convert the tritium 5'-AMP to tritium adenosine. The reaction mixture was passed through a cation exchange resin to allow the resin to adsorb the tritium adenosine. The resulting resin was washed with distilled water, and elution was conducted with 1.5 ml of a 3N ammonia water. The eluate was measured for radioactivity of tritium adenosine by an ordinary method using a liquid scintillation counter, to determine a phosphodiesterase activity.

Thus, there were determined the phosphodiesterase activities (Vs) of each test compound at various concentrations. Using the Vs and a Vc (the activity of a control, i.e. a water containing no test compound), there was calculated a phosphodiesterase inhibition (%) using the following formula.

Phosphodiesterase inhibition (%)=[(Vc-Vs)/Vc]×100

Thus, there were calculated the phosphodiesterase inhibitions (%) of each test compound at various concentrations. Using these values, there was determined a 50% phosphodiesterase inhibition concentration ($IC_{50}$) of each test compound.

In Table 61 are shown the $IC_{50}$ values of some of the compounds obtained in the Examples, each used as a test compound.

TABLE 61

| Test compound | $IC_{50}$ (μM) |
| --- | --- |
| Example | |
| 28 | 0.48 |
| 79 | Less than 0.1 |
| 85 | Less than 0.1 |
| 89 | Less than 0.1 |
| 134 | 0.49 |
| 93 | Less than 0.1 |
| 143 | 1.44 |

TABLE 61-continued

| Test compound | IC$_{50}$ (μM) |
|---|---|
| 70 | Less than 0.1 |

Preparation Example 1 (Preparation of tablets)

There were prepared, according to the following recipe, 1,000 tablets for oral administration each containing 5 mg of 6-[4-{N-cyclooctylmethyl-N-[2-(4-hydroxy-1piperidinyl)ethyl]amino}butoxy] carbostyril.

| Component | Amount (g) |
|---|---|
| 6-[4-{N-cyclooctylmethyl-N-[2-(4-hydroxy-1-piperidinyl)ethyl]amino}butoxy]carbostyril | 5 |
| Lactose (Japanese Pharmacopoeia grade) | 50 |
| Corn starch (Japanese Pharmacopoeia grade) | 25 |
| Crystalline cellulose (Japanese Pharmacopoeia grade) | 25 |
| Methyl cellulose (Japanese Pharmacopoeia grade) | 1.5 |
| Magnesium stearate (Japanese Pharmacopoeia grade) | 1 |

That is, there were thoroughly mixed 6-[4-{N-cyclooctylmethyl-N-[2-(4-hydroxy-1-piperidinyl)ethyl]amino}butoxy]carbostyril, lactose, corn starch and crystalline cellulose. The mixture was granulated with a 5% aqueous methyl cellulose solution, and the granules were passed through a 200-mesh sieve and dried carefully. The dried granules were passed through a 200-mesh sieve and mixed with magnesium stearate. The mixture was subjected to press molding to obtain tablets.

Preparation Example 2 (Preparation of capsules)

There were prepared, according to the following recipe, 1,000 two-piece hard gelatin capsules for oral administration each containing 10 mg of 6-[3-{N-benzyl-N-[2-(4-hydroxy-1-piperidinyl)ethyl] aminosulfonyl}propoxy]-carbostyril.

| Component | Amount (g) |
|---|---|
| 6-[3-{N-benzyl-N-[2-(4-hydroxy-1-piperidinyl)ethyl]aminosulfonyl}propoxy]-carbostyril | 10 |
| Lactose (Japanese Pharmacopoeia grade) | 80 |
| Starch (Japanese Pharmacopoeia grade) | 30 |
| Talc (Japanese Pharmacopoeia grade) | 5 |
| Magnesium stearate (Japanese Pharmacopoeia grade) | 1 |

That is, the above components were finely ground and thoroughly stirred so as to give a uniform mixture. The mixture was filled into gelatin capsules for oral administration, each having a desired dimension.

Preparation Example 3 (Preparation of injection)

A sterile aqueous solution suitable for parenteral administration was prepared according to the following recipe.

| Component | Amount (g) |
|---|---|
| 6-[4-{N-cyclohexylmethyl-N-(2,3-dihydroxypropyl)amino}butoxy]carbostyril | 1 |
| Polyethylene glycol (Japanese Pharmacopoeia grade) (molecular weight: 4,000) | 0.3 |
| Sodium chloride (Japanese Pharmacopoeia grade) | 0.9 |
| Polyoxyethylene sorbitan monooleate (Japanese Pharmacopoeia grade) | 0.4 |
| Sodium metabisulfite | 0.1 |
| Methylparaben (Japanese Pharmacopoeia grade) | 0.18 |
| Propylparaben (Japanese Pharmacopoeia grade) | 0.02 |
| Distilled water for injection | 100 ml |

That is, the parabens, sodium metabisulfite and sodium chloride were dissolved in distilled water of about half of the above volume, at 80° C. with stirring. The resulting solution was cooled to 40° C. Therein were dissolved 6-[4-{N-cyclohexylmethyl-N-(2,3-dihydroxypropyl)amino}butoxy] carbostyril, polyethylene glycol and polyoxyethylene sorbitan monooleate in this order. To the resulting solution was added distilled water for injection to make a final volume. The solution was filtered for sterilization through an appropriate filter paper to prepare an injection.

I claim:

1. A carbostyril derivative or salt thereof of the formula (1A)

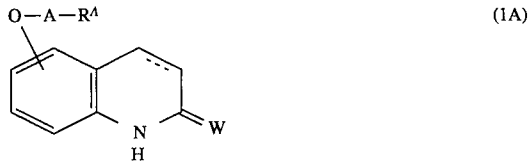

(1A)

wherein A is a lower alkylene group;

$R^A$ is a group

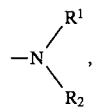

a group

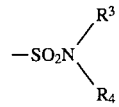

or a group

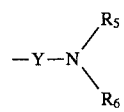

wherein $R_1$ is a group

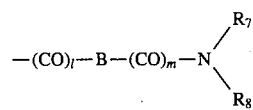

(wherein l and m independently are 0 or 1, B is a lower alkylene group, and each of $R^7$ and $R^8$, which may be the same or different, is a hydrogen atom, a lower alkyl group which may have a hydroxyl group, or a lower alkanoyl group or R⁷ and R⁸ may form a five- or six-membered saturated heterocyclic ring together with the nitrogen atom to which they bond and further with or without a nitrogen, oxygen or sulfur atom between R⁷ and R⁸, said heterocyclic ring may have from 1–3 substituents selected from the group consisting of a hydroxyl group, a lower alkyl group which may have a lower alkoxy-lower alkoxy group or a hydroxyl group, a lower alkyl group-substituted or unsubstituted amino group, a lower alkoxy-lower alkoxy group, an oxo group and a lower alkyl group-substituted or unsubstituted aminocarbonyl group or said heterocyclic ring may also have a lower alkylenedioxy group as a substituent); or R¹ is a lower alkoxycarbonyl group-substituted lower alkyl group; a carboxy group-substituted lower alkyl group; a lower alkyl group having, as a substituent, a lower alkyl group-substituted or unsubstituted aminocarbonyl group; a hydroxyl group-containing lower alkyl group; an imidazolyl-substituted lower alkyl group; a pyridyl-substituted lower alkyl group; a pyrrolidinyl-lower alkyl group which may have, as substituents on the pyrrolidine ring, from 1–3 groups selected from the group consisting of a lower alkyl group, a lower alkoxy-lower alkoxy group and a hydroxyl group; or a group —SO₂—D—R⁹ (wherein D is a lower alkylene group and R⁹ is a five- or six-membered saturated or unsaturated heterocyclic ring residue having from 1–3 halogen atoms or nitrogen atoms, said heterocyclic ring may have, as a substituent, a hydroxyl group, a lower alkoxy-lower alkoxy group, a lower alkoxy-carbonyl group, or a lower alkyl group which may have a lower alkoxy-lower alkoxy group or a hydroxyl group);

R² is a hydrogen atom; a cycloalkyl-lower alkyl group; a cycloalkyl group; a phenyl group; a phenyl-lower alkyl group which may have, as substituents on the phenyl ring, from 1–3 groups selected from the group consisting of a halogen atom, a lower alkyl group, a cyano group, a carboxy group and a lower alkoxy group; a pyridyl-substituted lower alkyl group; a thienyl-substituted lower alkyl group; a cycloalkylcarbonyl group; a benzoyl group; a tetrahydropyranyl-substituted lower alkyl group; a phenyl-lower alkylsulfonyl group; a phenylsulfonyl group; or a cycloalkyl-lower alkylsulfonyl group;

R¹ and R² may form a pyrrolidinyl group together with the nitrogen atom to which they bond, said pyrrolidinyl group having from 1–2 substituents selected from the group consisting of a hydroxyl group a lower alkoxy-lower alkoxy group, a lower alkyl group having a lower alkoxy-lower alkoxy group or a hydroxyl group, a lower alkoxycarbonyl group, a piperidinylcarbonyl group and a cycloalkyl-lower alkyl group-substituted or unsubstituted aminocarbonyl group;

R³ is a hydrogen atom; a lower alkyl group which may have a hydroxyl group; a carboxy-substituted lower alkyl group; a lower alkoxycarbonyl group-substituted lower alkyl group; a group

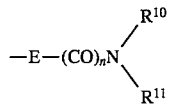

(wherein E is a lower alkylene group which may have a hydroxyl group, n is 0 or 1, and each of R¹⁰ and R¹¹, which may be the same or different, is a hydrogen atom; a lower alkyl group which may have a hydroxyl group; or a lower alkanoyl group, or R¹⁰ and R¹¹ may form a five- or six-membered saturated heterocyclic ring together with the nitrogen atom to which they bond and further with or without a nitrogen, oxygen or sulfur atom present between R¹⁰ and R¹¹, said heterocyclic ring may have from 1–3 substituents selected from the group consisting of a hydroxyl group, an oxo group, a lower alkoxy-lower alkoxy group, a lower alkyl group which may have a lower alkoxy-lower alkoxy group or a hydroxyl group, and a lower alkyl-substituted or unsubstituted amino group or said heterocyclic ring may also have a lower alkylenedioxy group as a substituent); or R₃ is a pyrrolidinyl-lower alkyl group which may have, as substituents on the pyrrolidine ring, from 1–3 groups selected from the group consisting of a lower alkyl group, a lower alkoxy-lower alkoxy group and a hydroxyl group;

R⁴ is a hydrogen atom; a cycloalkyl group; a cycloalkyl-lower alkyl group; a phenyl-lower alkyl group which may have, as substituents on the phenyl ring, from 1–3 groups selected from the group consisting of a halogen atom, a lower alkyl group and a lower alkoxy group; a phenyl group; a thienyl-substituted lower alkyl group; a pyridyl-substituted lower alkyl group; an imidazolyl-substituted lower alkyl group; or a tetra-hydropyranyl-substituted lower alkyl group;

Y is a group

a group

or a group

each of R⁵ and R⁶, which may be the same or different, is a hydrogen atom; a lower alkyl group; a cycloalkyl group; a cycloalkyl-lower alkyl group; or a piperidinyl-lower alkyl group which may have, as a substituent on the piperidinyl ring, a lower alkoxy-lower alkoxy group or a hydroxyl group; and W is an oxygen atom or a sulfur atom, the carbon-to-carbon bond between the 3- and 4-positions of the carbostyril skeleton being a single bond or a double bond;

provided that when W is an oxygen atom and R¹ is a hydroxyl group-containing lower alkyl group, R² is not any of a hydrogen atom, a cycloalkyl group and a phenyl-lower alkyl group which may have, as substituents on the phenyl ring, from 1–3 groups selected from the group consisting of a lower alkoxy group and a halogen atom, and when R¹ and R² form a pyrrolidinyl group, the pyrrolidinyl group is not a pyrrolidinyl group substituted with a hydroxyl group or with a hydroxyl group-containing lower alkyl group.

2. The carbostyril derivative or its salt according to claim 1, wherein W is an oxygen atom.

3. The carbostyril derivative or its salt according to claim 1, wherein W is a sulfur atom.

4. The carbostyril derivative or its salt according to claim 2, Wherein $R^A$ is a group

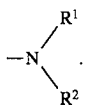

5. The carbostyril derivative or its salt according to claim 2, wherein $R^A$ is a group

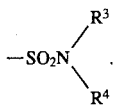

6. The carbostyril derivative or its salt according to claim 2, wherein $R^A$ is a group

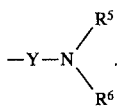

7. The carbostyril derivative or its salt according to claim 4, wherein $R^1$ is a group

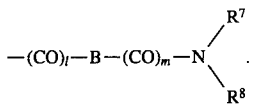

8. The carbostyril derivative or its salt according to claim 4 wherein $R^1$ is a group $-SO_2-D-R^9$.

9. The carbostyril derivative or its salt according to claim 4, wherein $R^1$ and $R^2$ form a pyrrolidinyl group together with the nitrogen atom to which they bond and said pyrrolidinyl group has 1–2 substituents selected from the group consisting of a hydroxyl group, a lower alkoxy-lower alkoxy group, a lower alkyl group having a lower alkoxy-lower alkoxy group or a hydroxyl group, a lower alkoxycarbonyl group, a piperidinylcarbonyl group and a cycloalkyl-lower alkyl group-substituted or unsubstituted aminocarbonyl group.

10. The carbostyril derivative or its salt according to claim 4, wherein $R^1$ is a lower alkoxycarbonyl group-substituted lower alkyl group, a carboxy group-substituted lower alkyl group, a lower alkyl group having, as a substituent, a lower alkyl group-substituted or unsubstituted aminocarbonyl group; a hydroxyl group-containing lower alkyl group; an imidazolyl-substituted lower alkyl group; a pyridinyl-substituted lower alkyl group, or a pyrrolidinyl-lower alkyl group which may have, as substituent(s) on the pyrrolidine ring, 1–3 groups selected from the group consisting of a lower alkyl group, a lower alkoxy-lower alkoxy group and a hydroxyl group.

11. The carbostyril derivative or its salt according to claim 7, wherein $R^2$ is a phenyl-lower alkyl group which may have, as substituents on the phenyl ring, 1–3 groups selected from the group consisting of a halogen atom, a lower alkyl group, a cyano group, a carboxy group and a lower alkoxy group.

12. The carbostyril derivative or its salt according to claim 7, wherein $R^2$ is a hydrogen atom, a cycloalkyl-lower alkyl group, a cycloalkyl group, a phenyl group, a pyridyl-substituted lower alkyl group, a thienyl-substituted lower alkyl group, a cycloalkylcarbonyl group, a benzoyl group, a tetrahydropyranyl-substituted lower alkyl group, a phenyl-lower alkylsulfonyl group, a phenylsulfonyl group or a cycloalkyl-lower alkylsulfonyl group.

13. The carbostyril derivative or its salt according to claim 8, wherein $R^2$ is a phenyl-lower alkyl group which may have, as substituents on the phenyl ring, 1–3 groups selected from the group consisting of a halogen atom, a lower alkyl group, a cyano group, a carboxy group and a lower alkoxy group.

14. The carbostyril derivative or its salt according to claim 8, wherein $R^2$ is a hydrogen atom, a cycloalkyl-lower alkyl group, a cycloalkyl group, a phenyl group, a pyridyl-substituted lower alkyl group, a thienyl-substituted lower alkyl group, a cycloalkylcarbonyl group, a benzoyl group, a tetrahydropyranyl-substituted lower alkyl group, a phenyl-lower alkylsulfonyl group, a phenylsulfonyl group or a cycloalkyl-lower alkylsulfonyl group.

15. The carbostyril derivative or its salt according to claim 9, wherein $R^2$ is a phenyl-lower alkyl group which may have, as substituent(s) on the phenyl ring, 1–3 groups selected from the group consisting of a halogen atom, a lower alkyl group, a cyano group, a carboxy group and a lower alkoxy group.

16. The carbostyril derivative or its salt according to claim 9, wherein $R^2$ is a hydrogen atom, a cycloalkyl-lower alkyl group, a cycloalkyl group, a phenyl group, a pyridyl-substituted lower alkyl group, a thienyl-substituted lower alkyl group, a cycloalkylcarbonyl group, a benzoyl group, a tetrahydropyranyl-substituted lower alkyl group, a phenyl-lower alkylsulfonyl group, a phenylsulfonyl group or a cycloalkyl-lower alkylsulfonyl group.

17. The carbostyril derivative or its salt according to claim 10, wherein $R^2$ is a phenyl-lower alkyl group which may have, as substituents on the phenyl ring, 1–3 groups selected from the group consisting of a halogen atom, a lower alkyl group, a cyano group, a carboxy group and a lower alkoxy group.

18. The carbostyril derivative or its salt according to claim 10, wherein $R^2$ is a a hydrogen atom, a cycloalkyl-lower alkyl group, a cycloalkyl group, a phenyl group, a pyridyl-substituted lower alkyl group, a thienyl-substituted lower alkyl group, a cycloalkylcarbonyl group, a benzoyl group, a tetrahydropyranyl-substituted lower alkyl group, a phenyl-lower alkylsulfonyl group, a phenylsulfonyl group or a cycloalkyl-lower alkylsulfonyl group.

19. The carbostyril derivative or its salt according to claim 11, wherein l is 0; $R^7$ and $R^8$ may form a five- or six-membered saturated heterocyclic ring, together with the nitrogen atom to which they bond and further with or without a nitrogen, oxygen or sulfur atom which may be present between $R^7$ and $R^8$; said heterocyclic ring may have 1–3 substituents selected from the group consisting of a hydroxyl group, a lower alkyl group which may have a lower alkoxy-lower alkoxy group or a hydroxyl group, a lower alkyl group-substituted or unsubstituted amino group, a lower alkoxy-lower alkoxy group, an oxo group and a lower alkyl group-substituted or unsubstituted aminocarbonyl group; and said heterocylic ring may also have a lower alkylenedioxy group as a substituent.

20. The carbostyril derivative or its salt according to claim 11, wherein l is 0 and each of $R^7$ and $R^8$, which may be the same or different, is a hydrogen atom, a lower alkyl group which may have a hydroxyl group, or a lower alkanoyl group.

21. The carbostyril derivative or its salt according to claim 12, wherein l is 0; $R^7$ and $R^8$ may form a five- or six-membered saturated heterocyclic ring, together with the nitrogen atom to which they bond and further with or without a nitrogen, oxygen or sulfur atom which may be present between $R^7$ and $R^8$; said heterocyclic ring may have 1–3 substituents selected from the group consisting of a hydroxyl group, a lower alkyl group which may have a lower alkoxy-lower alkoxy group or a hydroxyl group, a lower alkyl group-substituted or unsubstituted amino group, a lower alkoxy-lower alkoxy group, an oxo group and a lower alkyl group-substituted or unsubstituted aminocarbonyl group; and said heterocylic ring may also have a lower alkylenedioxy group as a substituent.

22. The carbostyril derivative or its salt according to claim 12, wherein l is 0 and each of $R^7$ and $R^8$, which may be the same or different, is a hydrogen atom, a lower alkyl group which may have a hydroxyl group, or a lower alkanoyl group.

23. The carbostyril derivative or its salt according to claim 11 or 12, wherein l is 1.

24. The carbostyril derivative or its salt according to any of claims 13 to 22, wherein the carbon-to-carbon bond between the 3- and 4-positions of the carbostyril skeleton is a single bond.

25. The carbostyril derivative or its salt according to any of claims 13 to 22, wherein the carbon-to-carbon bond between the 3- and 4-positions of the carbostyril skeleton is a double bond.

26. The carbostyril derivative or its salt according to claim 19 or 21, wherein the heterocyclic ring is pyrrolidinyl, piperidinyl, piperazinyl, morpholinyl, thiomorpholinyl, isothiazolidinyl or 3,4, 5, 6-tetrahydro-1,2-thiazinyl.

27. The carbostyril derivative or its salt according to claim 5, wherein $R^3$ is a group

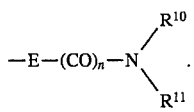

28. The carbostyril derivative or its salt according to claim 5, wherein $R^3$ is a hydrogen atom, a lower alkyl group which may have a hydroxyl group, a carboxy-substituted lower alkyl group, a lower alkoxycarbonyl group-substituted lower alkyl group, or a pyrrolidinyl-lower alkyl group which may have, as substituent(s) on the pyrrolidine ring, 1–3 groups selected from the group consisting of a lower alkyl group, a lower alkoxy-lower alkoxy group and a hydroxyl group.

29. The carbostyril derivative or its salt according to claim 27, wherein $R^{10}$ and $R^{11}$ may form a five- or six-membered saturated heterocyclic ring, together with the nitrogen atom to which they bond and further with or without a nitrogen, oxygen or sulfur atom which may be present between $R^{10}$ and $R^{11}$; said heterocyclic ring may have 1–3 substituents selected from the group consisting of a hydroxyl group, an oxo group, a lower alkoxy-lower alkoxy group, a lower alkyl group which may have a lower alkoxy-lower alkoxy group or a hydroxyl group, and a lower alkyl-substituted or unsubstituted amino group; and said heterocylic ring may also have a lower alkylenedioxy group as a substituent.

30. The carbostyril derivative or its salt according to claim 27, wherein each of $R^{10}$ and $R^{11}$, which may be the same or different, is a hydrogen atom, a lower alkyl group which many have a hydroxyl group, or a lower alkanoyl group.

31. The carbostyril derivative or its salt according to claim 27 or 28, wherein $R^4$ is a cycloalkyl group, a cycloalkyl-lower alkyl group, a phenyl-lower alkyl group which may have, as substituent(s) on the phenyl ring, 1–3 groups selected from the group consisting of a halogen atom, a lower alkyl group and a lower alkoxy group, or a thienyl-substituted lower alkyl group.

32. The carbostyril derivative or its salt according to claim 27 or 28, wherein $R^4$ is a hydrogen atom, a phenyl group, a pyridyl-substituted lower alkyl group, an imidazolyl-substituted lower alkyl group or a tetrahydropyranyl-substituted lower alkyl group.

33. The carbostyril derivative or its salt according to claim 29, wherein the heterocyclic ring is pyrrolidinyl, piperidinyl, piperazinyl, morpholinyl, thiomorpholinyl, isothiazolidinyl or 3,4,5,6-tetrahydro-1,2-thiazinyl.

34. The carbostyril derivative or its salt according to any of claims 28, 29 and 30, wherein the carbon-to-carbon bond between the 3- and 4-positions of the carbostyril skeleton is a single bond.

35. The carbostyril derivative or its salt according to any of claims 28, 29 and 30, wherein the carbon-to-carbon bond between the 3- and 4-positions of the carbostyril skeleton is a double bond.

36. The carbostyril derivative or its salt according to claim 6, wherein Y is a group

37. The carbostyril derivative or its salt according to claim 6, wherein Y is a group

or a group

38. The carbostyril derivative or its salt according to claim 36 or 37, wherein the carbon-to-carbon bond between the 3- and 4-positions of the carbostyril skeleton is a single bond.

39. The carbostyril derivative or its salt according to claim 36 or 37, wherein the carbon-to-carbon bond between the 3- and 4-positions of the carbostyril skeleton is a double bond.

40. 6-[4-{N-[2-(4-hydroxy-1-piperidinyl)ethyl]-N-benzylamino}butoxy]carbostyril.

41. 6-{4-[N-(4-hydroxy-1-piperidinyl)carbonylmethyl]-N-benzylamino]butoxy}carbostyril.

42. 6-[5-{N-[2-(4-hydroxy-1-piperidinyl)ethyl]-N-(2-chlorobenzyl)amino}pentyloxy] carbostyril.

43. 6-[3-{N-[2-(4-hydroxy-1-piperidinyl)ethyl]-N-cyclooctylamino}sulfonylpropoxy]carbostyril.

44. 6-[4-{N-[2-(4-hydroxy-1-piperidinyl)ethyl-N-[(2-thienyl)methyl]amino} sulfonylbutoxy]carbostyril.

45. 7-[4-{N-[2-(4-hydroxy-1-piperidinyl)ethyl]-N-cyclooctylmethylamino} sulfonylbutoxy]carbostyril.

46. 6-[4-{N-[2-(4-hydroxy-1-piperidinyl)ethyl]-N-(2-chlorobenzyl)amino} sulfonylbutoxy]carbostyril.

47. 6-[3-{N-[2-(4-hydroxy-1-piperidinyl)ethyl]-N-cyclooctylmethylamino} carbonylaminopropoxy]carbostyril.

48. A platelets aggregation inhibitory agent containing, as an active ingredient, a carbostyril derivative or salt thereof of claim 1.

49. A phosphodiesterase inhibitory agent containing, as an active ingredient, a carbostyril derivative or salt thereof of claim 1.

50. A platelets adhesion inhibitory agent containing, as an active ingredient, a carbostyril derivative or salt thereof of claim 1.

51. A method for platelets aggregation inhibition, which uses, as an active ingredient, a carbostyril derivative or salt thereof of formula (1)

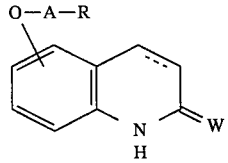 (1)

wherein A is a lower alkylene group;

R is a group

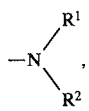

a group

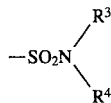

or a group

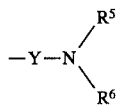

wherein $R^1$ is a group

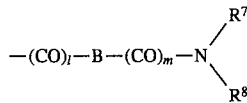

(wherein l and m independently are 0 or 1, B is a lower alkylene group and each of $R^7$ and $R^8$, which may be the same or different, is a hydrogen atom, a lower alkyl group which may have a hydroxyl group, or a lower alkanoyl group or $R^7$ and $R^8$ may form a five- or six-membered saturated heterocyclic ring together with the nitrogen atom to which they bond and further with or without a nitrogen, oxygen or sulfur atom between $R^7$ and $R^8$, said heterocyclic ring may have from 1–3 substituents selected from the group consisting of a hydroxyl group, a lower alkyl group which may have a lower alkoxy-lower alkoxy group or a hydroxyl group, a lower alkyl group-substituted or unsubstituted amino group, a lower alkoxy-lower alkoxy group, an oxo group and a lower alkyl group-substituted or unsubstituted aminocarbonyl group or said heterocyclic ring may also have a lower alkylenedioxy group as a substituent); or $R^1$ is a lower alkoxycarbonyl group-substituted lower alkyl group; a carboxy group-substituted lower alkyl group; a lower alkyl group having, as a substituent, a lower alkyl group-substituted or unsubstituted aminocarbonyl group; a hydroxyl group-containing lower alkyl group; an imidazolyl-substituted lower alkyl group; a pyridyl-substituted lower alkyl group; a pyrrolidinyl-lower alkyl group which may have, as substituents on the pyrrolidine ring, from 1–3 groups selected from the group consisting of a lower alkyl group, a lower alkoxy-lower alkoxy group and a hydroxyl group; or a group —$SO_2$—D—$R^9$ (wherein D is a lower alkylene group, and $R^9$ is a five- or six-membered saturated or unsaturated heterocyclic ring residue having from 1–3 halogen atoms or nitrogen atoms, said heterocyclic ring may have, as a substituent, a hydroxyl group, a lower alkoxy-lower alkoxy group, a lower alkoxycarbonyl group, or a lower alkyl group which may have a lower alkoxy-lower alkoxy group or a hydroxyl group);

$R^2$ is a hydrogen atom; a cycloalkyl-lower alkyl group; a cycloalkyl group; a phenyl group; a phenyl-lower alkyl group which may have, as substituents on the phenyl ring, from 1–3 groups selected from the group consisting of a halogen atom, a lower alkyl group, a cyano group, a carboxy group and a lower alkoxy group; a pyridyl-substituted lower alkyl group; a thienyl-substituted lower alkyl group; a cycloalkylcarbonyl group; a benzoyl group; a tetrahydropyranyl-substituted lower alkyl group; a phenyl-lower alkylsulfonyl group; a phenylsulfonyl group; or a cycloalkyl-lower alkylsulfonyl group;

$R^1$ and $R^2$ may form a pyrrolidinyl group together with the nitrogen atom to which they bond, said pyrrolidinyl group having from 1–2 substituents selected from the group consisting of a hydroxyl group, a lower alkoxy-lower alkoxy group, a lower alkyl group which may have a lower alkoxy-lower alkoxy group or a hydroxyl group, a lower alkoxycarbonyl group, a piperidinylcarbonyl group and a cycloalkyl-lower alkyl group-substituted or unsubstituted aminocarbonyl group;

$R^3$ is a hydrogen atom; a lower alkyl group which may have a hydroxyl group; a carboxy-substituted lower alkyl group; a lower alkoxycarbonyl group-substituted lower alkyl group; a group

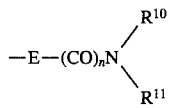

(wherein E is a lower alkylene group which may have a hydroxyl group, n is 0 or 1, and each of $R^{10}$ and $R^{11}$, which may be the same or different is a hydrogen atom; a lower alkyl group which may have a hydroxyl group; or a lower alkanoyl group, or $R^{10}$ and $R^{11}$ may form a five- or six-membered saturated heterocyclic ring, together with the nitrogen atom to which they bond and further with or without a nitrogen, oxygen or sulfur atom present between $R^{10}$ and $R^{11}$, said heterocyclic ring may have from 1–3 substituents selected from the group consisting of a hydroxyl group, an oxo group, a lower alkoxy-lower alkoxy group, a lower alkyl group which may have a lower alkoxy-lower alkoxy group or a hydroxyl group, and a lower alkyl-substituted or unsubstituted amino group, or said heterocyclic ring may also have a lower alkylenedioxy group as a substituent); or $R^3$ is a pyrrolidinyl-lower alkyl group which may have, as substituents on the pyrrolidine ring, from 1–3 groups selected from the group consisting of a lower alkyl group, a lower alkoxy-lower alkoxy group and a hydroxyl group;

$R^4$ is a hydrogen atom; a cycloalkyl group; a cycloalkyl-lower alkyl group; a phenyl-lower alkyl group which may have, as substituents on the phenyl ring, from 1–3 groups selected from the group consisting of a halogen atom, a lower alkyl group and a lower alkoxy group; a phenyl group; a thienyl-substituted lower alkyl group; a pyridyl-substituted lower alkyl group; an imidazolyl-substituted lower alkyl group; or a tetra-hydropyranyl substituted lower alkyl group;

Y is a group

a group

or a group

each of $R^5$ and $R^6$, which may be the same or different, is a hydrogen atom; a lower alkyl group; a cycloalkyl group; a cycloalkyl-lower alkyl group; or a piperidinyl-lower alkyl group which may have, as a substituent on the piperidinyl ring, a lower alkoxy-lower alkoxy group or a hydroxyl group; and W is an oxygen atom or a sulfur atom, the carbon-to-carbon bond between the 3- and 4-positions of the carbostyril skeleton being a single bond or a double bond.

52. A process for producing a carbostyril compound of claim 1 comprising reacting a compound (4) represented by general formula (4)

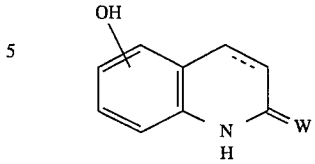

wherein W and the carbon-to-carbon bond between the 3- and 4-positions of the carbostyril skeleton have the same definitions as defined in claim 1 with a compound (5) represented by general formula (5)

wherein X represents a halogen atom, a lower alkanesulfonyloxy group, an arylsulfonyloxy group or an aralkylsulfonyloxy group and A and $R^A$ have the same definitions as defined in claim 61 in an appropriate solvent in the presence of a basic compound used as a dehalogenating agent.

\* \* \* \* \*

UNITED STATES PATENT AND TRADEMARK OFFICE
CERTIFICATE OF CORRECTION

PATENT NO. : 5,506,239
DATED : April 9, 1996
INVENTOR(S) : Seiji Sato et al.

It is certified that error appears in the above-indentified patent and that said Letters Patent is hereby corrected as shown below:

Claim 52, column 106, line 5, "(4)" is missing beside formula.

Claim 53, column 106, line 10, "(3)" should read -- 3- --.

Signed and Sealed this

Sixth Day of August, 1996

Attest:

BRUCE LEHMAN

Attesting Officer    Commissioner of Patents and Trademarks